United States Patent
Huang

(10) Patent No.: US 11,219,401 B2
(45) Date of Patent: Jan. 11, 2022

(54) METHOD, MODULE AND SYSTEM FOR ANALYSIS OF PHYSIOLOGICAL SIGNAL

(71) Applicant: Adaptive, Intelligent and Dynamic Brain Corporation (AidBrain), Taoyuan (TW)

(72) Inventor: Norden E. Huang, Bethesda, MD (US)

(73) Assignee: Adaptive, Intelligent and Dynamic Brain Corporation (AidBrain), Taoyuan (TW)

(*) Notice: Subject to any disclaimer, the term of this patent is extended or adjusted under 35 U.S.C. 154(b) by 327 days.

(21) Appl. No.: 16/214,168

(22) Filed: Dec. 10, 2018

(65) Prior Publication Data

US 2019/0175041 A1 Jun. 13, 2019

Related U.S. Application Data

(60) Provisional application No. 62/596,912, filed on Dec. 11, 2017.

(51) Int. Cl.

| | |
|---|---|
| *A61B 5/374* | (2021.01) |
| *A61B 5/339* | (2021.01) |
| *A61B 5/389* | (2021.01) |
| *A61B 5/245* | (2021.01) |
| *A61B 5/00* | (2006.01) |
| *A61B 5/021* | (2006.01) |

(52) U.S. Cl.
CPC ............ *A61B 5/374* (2021.01); *A61B 5/0006* (2013.01); *A61B 5/021* (2013.01); *A61B 5/339* (2021.01); *A61B 5/389* (2021.01); *A61B 5/72* (2013.01); *A61B 5/7253* (2013.01); *A61B 5/743* (2013.01); *A61B 5/245* (2021.01); *A61B 5/4088* (2013.01)

(58) Field of Classification Search
CPC ....... A61B 5/0006; A61B 5/245; A61B 5/339; A61B 5/374; A61B 5/72; A61B 5/7253; A61B 5/743; G16H 10/00–65; G16H 15/00; G16H 40/63; G16H 50/00–80
See application file for complete search history.

(56) References Cited

U.S. PATENT DOCUMENTS

| | | |
|---|---|---|
| 2010/0240999 A1 | 9/2010 | Droitcour et al. |
| 2015/0193376 A1 | 7/2015 | Yeh et al. |
| 2016/0224757 A1 | 8/2016 | Melkonyan |
| 2017/0079538 A1 | 3/2017 | Liang et al. |
| 2017/0200089 A1 | 7/2017 | Huang |
| 2017/0224238 A1 | 8/2017 | Arunachalam et al. |
| 2018/0146876 A1* | 5/2018 | Brown ............ A61B 5/316 |

* cited by examiner

*Primary Examiner* — Thaddeus B Cox
(74) *Attorney, Agent, or Firm* — ScienBiziP, P.C.

(57) ABSTRACT

The present disclosure provides a non-transitory computer program product embodied in a computer-readable medium and, when executed by one or more analysis modules, providing a visual output for presenting physiological signals of a cardiovascular system. The non-transitory computer program product comprises a first axis representing, subsets of intrinsic mode functions (IMF); a second axis representing a function of signal strength in a time interval; and a plurality of visual elements, each of the visual elements being defined by the first axis and the second axis, and each of the visual elements comprising a plurality of analyzed data units collected over the time interval. Wherein each of the analyzed data units comprises a first coordinate, a second coordinate, and a probability density value generated from an intrinsic probability density function of one of the subsets of IMFs.

6 Claims, 54 Drawing Sheets

METHOD, MODULE AND SYSTEM FOR ANALYSIS OF PHYSIOLOGICAL SIGNAL

CROSS-REFERENCE TO RELATED APPLICATION

The present disclosure claims the benefit of U.S. provisional patent application No. 62/596,912, filed on Dec. 11, 2017, the entirety of which is incorporated herein by reference.

FIELD

The present disclosure is generally related to the method, module and system for analysis of physiological signal. More particularly, the present disclosure is directed to a method, module and system for analysis of electrical activities of the brain.

BACKGROUND OF THE INVENTION

The brain function is dynamic and relevant to brain structures and electrical activities of the bran. Structural deficiencies of the brain could be detected by various conventional medical imaging techniques such as computed tomography (CT) scan, magnetic resonance imaging (MRI), positron emission tomography (PET), and single-photo emission computed tomography (SPET). However, the conventional medical imaging techniques could not capture the dynamic nature of the brain functions. Furthermore, many mental or psychiatric conditions have no discernable structural changes in the brain, these conditions may include: depression, insomnia, mild cognitive impairment, the initial stage of Alzheimer's disease, ADHD, and different depths of anesthesia.

Electroencephalography (EEG), magnetoencephalography (MEG), and electrocorticography (ECoG) can be used to measure the electrical activities of the brain, these methods provide real-time information of the brain function that are important in diagnosis, prognosis, staging, or clinical evaluation on certain neurological diseases. While ECoG requires a craniotomy and is an invasive procedure, EEG and MEG are non-invasive and in-expensive approaches to monitor the electrical activities of the brain. However, given the non-invasive nature of EEG and MEG, they can be interfered or disturbed by various anatomical structures of the head or the brain, such as conductivity variations of the scalp (skull compacta and skull spongiosa), cerebral spinal fluid (CSF), gray matter, and white matter. On other hand, ECoG is less disturbed and interfered by the anatomical structures of the head, because ECoG places detection modules directly on an exposed surface of the brain to measure the electrical activities.

Additionally, the non-stationary and non-linear nature of electrical activities of the brain are significant obstacles for signal processing. Conventional approaches for signal processing and analysis of EEG, MEG, or ECoG signals have failed to provide an effective solution to the obstacles. A conventional approach for signal processing can be Fourier transformation. Fourier transformation are often used to interpret linear and stationary wave signals, such as spectrum analysis; however, due to its mathematical nature, Fourier transformation is unable to provide meaningful visualization results from non-stationary and non-linear wave signals.

Another conventional approach for signal analysis is the probability distribution function. The probability distribution function is another tool for study non-deterministic phenomena. Nevertheless, the signals described by conventional probability distribution function need to be stationary and with large amplitude variations. Conventional probability distribution function is unable to provide insights from non-stationary and non-linear wave signals.

The Holo-Hilbert spectral analysis (HOSA) is a tool for visualizing non-stationary and non-linear waves. The mathematics behind HOSA has been summarized in Huang et al (Huang, N. E., Hu, K., Yang, A. C., Chang, H. C., Jia, D., Liang, W. K., Yeh, J. R., Kao, C. L., Juan, C. H., Peng, C. K. and Meijer, J. H. (2016). On Holo-Hilbert spectral analysis: a full informational spectral representation for nonlinear and non-stationary data. *Phil. Trans. R. Soc. A*, 374(2065)). HOSA adopts some of the mathematical methodologies of Hilbert-Huang transformation when analyzing non-stationary and non-linear waves. However, the application of HOSA on analysis of brain signals has never been explored and exploited.

Due to the lack of adequate signal processing and analysis tools, data associated with electrical activities of the brain often needs to be analyzed by trained professionals, in addition to available algorithms or software embedded instruments. For instance, EEG data could be massive in terms of their quantity and complexity, because EEG signals are generated from several EEG leads on the head and can be disturbed or interfered by anatomical structures on the head.

Given the non-linear and non-stationary nature, and the inherent complexity and quantity of electrical activities of the brain, there is a need for an efficient and intuitive mean for analysis and visualization of EEG and MEG. Specifically, a novel probability distribution function and a multi-scale entropy generated by HOSA are proposed in the present disclosure to reveal the subtlety and nuance of the variations in brain electrical activities.

SUMMARY OF THE INVENTION

It is an object of the present disclosure to provide HOSA-based methods and systems for analysis of electrical activities of the brain.

It is an object of the present disclosure to provide one or more visual outputs of electroencephalography (EEG), magnetoencephalography, and electrocorticography (ECoG).

It is also an object of the present disclosure to provide one or more visual outputs of abnormal EEG, MEG, and ECoG signals.

It is also an object of the present disclosure to provide one or more visual outputs to compare electrical activities of the brain in different groups of subjects, different subjects, or different time intervals of the same subjects.

It is also an object of the present disclosure to provide applications of HOSA in diagnosis of neurological disorders.

An embodiment of the present disclosure provides a non-transitory computer program product embodied in a computer-readable medium and, when executed by one or more analysis modules, providing a visual output for presenting physiological signals of a cardiovascular system. The non-transitory computer program product comprises a first axis representing subsets of intrinsic mode functions (IMF); a second axis representing a function of signal strength in a time interval; and a plurality of visual elements, each of the visual elements being defined by the first axis and the second axis, and each of the visual elements comprising a plurality of analyzed data units collected over the time interval. Wherein each of the analyzed data units comprises a first coordinate, a second coordinate, and a probability density value generated from an intrinsic probability density function of one of the subsets of IMFs, the first coordinate is one of the subsets of IMFs, and the second coordinate is an argument of the function of signal strength.

In a preferred embodiment of the present disclosure, the second axis is a standard deviation or a z-value of the signal strength in the time interval.

In a preferred embodiment of the present disclosure, the probability density value is generated from a subset of primary IMFs or secondary IMFs, each of the primary IMFs is generated from an empirical mode decomposition (EMD) of plurality of electrical activity signals, and each of the secondary IMFs is generated from an EMD of the primary IMF.

In a preferred embodiment of the present disclosure, the electrical signals of the brain are electroencephalography (EEG) signals, magnetoencephalography (MEG) signals, and electrocorticography (ECoG) signals.

Another embodiment of the present disclosure provides a system for analyzing electrical activities of at least one brain. The system comprises a detection module for detecting the electrical activities of the brain; a transmission module for receiving electrical activity signals from the detection module and transmitting the electrical activity signals to the analysis module; an analysis module for generating a plurality of analyzed data sets from the electrical activity signals, each of the analyzed data sets comprising a plurality of analyzed data units; and a visual output module for rendering a visual output space according to the analyzed data sets generated by the analysis module, and displaying a visual output. Wherein the visual output comprises a first axis representing subsets of IMFs, a second axis representing a function of signal strength in a time interval, and a plurality of visual elements defined by the first axis and the second axis, and each of the visual elements comprises a plurality of analyzed data units collected over the time interval, and each of the analyzed data units comprises a first coordinate, a second coordinate, and a probability density value generated by an intrinsic probability density function of one of the subsets of IMFs. The first coordinate is one of the subsets of IMFs, and the second coordinate is an argument of the function of signal strength.

Another embodiment of the present disclosure provides a non-transitory computer program product embodied in a computer-readable medium, and when executed by one or more analysis modules, providing a visual output for presenting electrical activities of at least one brain. The non-transitory computer program product comprises a first axis representing a function of signal strength in a time interval; a second axis representing a function of a time scale of an intrinsic probability density function; and a plurality of visual elements, each of the visual elements being defined by the first axis and the second axis, and each of the visual elements comprising a plurality of analyzed data units collected over the time interval. Wherein each of the analyzed data units comprises a first coordinate, a second coordinate, and a probability density value generated from the intrinsic probability density function of a subsets of IMFs. The first coordinate is an argument of the function of signal strength, and the second coordinate is an argument of the function of the time scale.

In a preferred embodiment, the second axis is an instantaneous frequency of the intrinsic probability density function.

In a preferred embodiment, the first axis is a standard deviation or a z-value of the signal strength in the time interval.

In a preferred embodiment, the probability density function is indicated by different colors, grayscales, dot densities, contour lines, or screentones.

Another embodiment of the present disclosure provides a system for analyzing electrical activities of at least one brain. The system comprises a detection module for detecting the electrical activities of the brain; a transmission module for receiving electrical activity signals from the detection module and transmitting the electrical activity signals to the analysis module; and analysis module for generating a plurality of analyzed data sets from the electrical activity signals, each of the analyzed data sets comprising a plurality of analyzed data units; and a visual output module for rendering a visual output space according to the analyzed data sets generated by the analysis module, and displaying a visual output. Wherein the visual output comprises a first axis representing a function of signal strength in a time interval, a second axis representing a function of a time scale of an intrinsic probability density function, and a plurality of visual elements defined by the first axis and the second axis, and each of the visual elements comprises a plurality of analyzed data units collected over the time interval, and each of the analyzed data units comprises a first coordinate, a second coordinate, and a probability density value generated by the intrinsic probability density function of a subset of IMFs. The first coordinate is an argument of the function of signal strength, and the second coordinate is an argument of the function of the time scale.

Another embodiment of the present disclosure provides a non-transitory computer program product embodied in a computer-readable medium and, when executed by one or more analysis module, providing a visual output for presenting electrical activities of at least one brain. The non-transitory computer program product comprises a boundary defining an anatomical graph of the brain; and one or more detection units in the boundary, and each of the detection units has a probability density value generated from an intrinsic probability density function of a subset of IMFs.

In a preferred embodiment, the visual output comprises a plurality of intermediate areas within the boundary and between the detection units, and each of the intermediate area has a modeled probability density value.

In a preferred embodiment, the visual output comprises a first axis representing a time interval, a second axis representing instantaneous frequency of the IMFs, and a plurality of visual elements defined by the boundary, a first coordinate of the first axis, and a second coordinate of the second axis.

Another embodiment of the present disclosure provides a system for analyzing electrical activities of at least one brain. The system comprises a detection module for detecting the electrical activities of the brain; a transmission module for receiving electrical activity signals from the detection modules and transmitting the electrical activity signals to the analysis module; an analysis module for generating a probability density function from the electrical activity signals; and a visual output module for rendering a visual output space according to the analyzed data sets generated by the analysis module, and displaying a visual output. Wherein the visual output comprises a boundary defining an anatomical graph of the brain, and one or more detection units in the boundary, and each of the detection unit has a probability density value generated from the intrinsic probability density function of a subset of IMFs.

Another embodiment of the present disclosure provides a non-transitory computer program product embodied in a computer-readable medium, and when executed by one or more analysis modules, providing a visual output for presenting electrical activities of at least one brain. The non-transitory computer program product comprises a first axis representing a scale of intrinsic multiscale entropy (iMSE); a second axis representing cumulative IMFs; and a plurality of visual elements, each of the visual elements being defined by the first axis and the second axis, and each of the visual elements comprising an analyzed data unit collected over a time interval. Wherein each of the analyzed data units comprises a first coordinate of the first axis, a second coordinate of the second axis, and an iMSE value generated from the IMFs.

In a preferred embodiment, the IMFs are a set of primary IMFs or a set of secondary IMFs, each of the primary IMFs is generated from an EMD of a plurality of electrical activity signals, and each of the secondary IMFs is generated from an EMD of the primary IMF.

In a preferred embodiment, each of the visual element further comprises a boundary defining an anatomical graph of the brain, and one or more detection units in the boundary, and each of the detection unit is assigned with the iMSE value.

In a preferred embodiment, each of the visual element further comprises a plurality of intermediate areas within the boundary and between the detection units, and each of the intermediate areas has a modeled iMSE value.

Another embodiment of the present disclosure provides a system for analyzing electrical activities of at least one brain. The system comprises a detection module for detecting the electrical activities of the brain; a transmission module for receiving electrical activity signals from the detection module and transmitting the electrical activity signals to the analysis module; an analysis module for generating a plurality of analyzed data sets from the electrical activity signals, each of the analyzed data sets comprising a plurality of analyzed data units; and a visual output module for rendering a visual output space according to the analyzed data sets generated by the analysis module, and displaying a visual output. Wherein the visual output comprises a first axis representing a scale of iMSE, a second axis representing cumulative IMFs, and a plurality of visual elements defined by the first axis and the second axis, and each of the visual elements being defined by the first axis and the second axis, and each of the visual elements comprising an analyzed data unit collected over a time interval, and each of the analyzed data units comprises a first coordinate of the first axis, a second coordinate of the second axis, and an iMSE value generated from the IMFs.

In a preferred embodiment, the iMSE values is indicated by different colors, grayscales, dot densities, contour lines, or screentones.

BRIEF DESCRIPTION OF THE DRAWINGS

Implementations of the present disclosure will now be described, by way of examples only, with reference to the attached figures.

DETAILED DESCRIPTION

Figure 1:
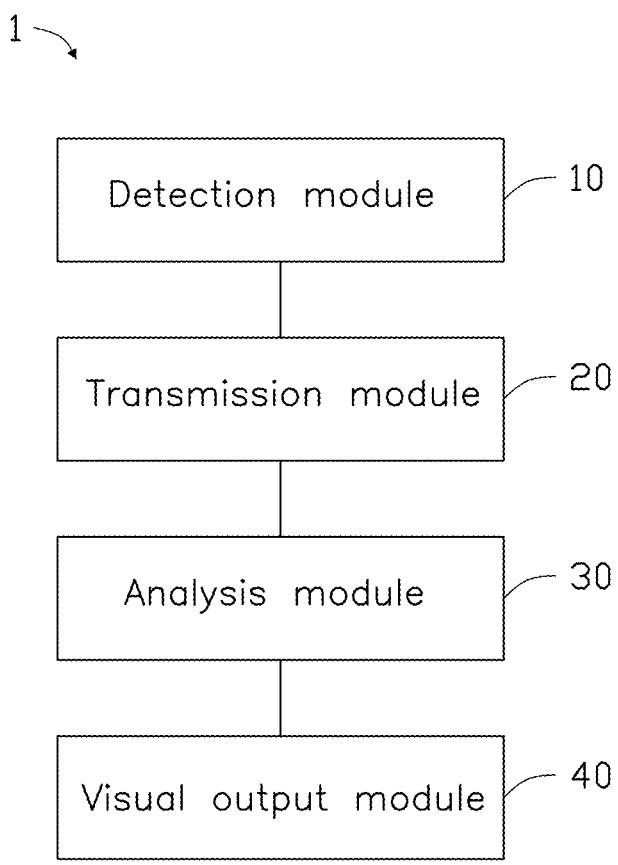
FIG. 1 is a schematic diagram of a system for analyzing electrical activities of the brain in accordance with an embodiment of the present disclosure.

It will be noted at the beginning that for simplicity and clarity of illustration, where appropriate, reference numerals have been repeated among the different figures to indicate corresponding or analogous elements. In addition, numerous specific details are set forth in order to provide a thorough understanding of the embodiments described herein. However, it will be understood by those of ordinary skill in the art that the embodiments described herein can be practiced without these specific details. In other instances, methods, procedures and components have not been described in detail so as not to obscure the related relevant feature being described. The drawings are not necessarily to scale and the proportions of certain parts may be exaggerated to better illustrate details and features. The description is not to be considered as limiting the scope of the embodiments described herein.

Several definitions that apply throughout this disclosure will now be presented.

The term "coupled" is defined as connected, whether directly or indirectly through intervening components, and is not necessarily limited to physical connections. The connection can be such that the objects are permanently connected or reliably connected. The term "comprising," when utilized, means "including, but not necessarily limited to"; it specifically indicates open-ended inclusion or membership in the so-described combination, group, series and the like.

Referring to FIG. 1, a system for analyzing electrical activities of the brain in accordance with an embodiment of the present disclosure is provided. The system 1 comprises a detection module 10, a transmission module 20, an analysis module 30 and a visual output module 40. The system 1 is configured to detect electrical activities of the brain, to analyze signals and to display graphical information of the analyzed results. The electrical activities of the brain may be represented by electroencephalography (EEG), magnetoencephalography (MEG), or electrocorticography (ECoG) signals. The system 1 may further comprise other electrical components or modules for better performance or user experience. For example, the system 1 may comprise an amplifier module or filter module to enhance signal to noise ratio by gaining signal strength within certain bandwidth and minimizing noise from environmental interference or baseline wandering. For example, the system 1 may comprise an analog-to-digital converter (ADC) for signal digitization. For example, the system 1 may further comprise a storage module for storing the digital signals or storing the analyzed data. In one example, the detection module 10 may further comprise a data acquisition module. The data acquisition module is capable of executing the functions of the amplifier module, ADC and the storage module. Furthermore, the system 1 may comprise a user input module for use to control the system 1, such as a keyboard, a mouse, a touch screen, or a voice control device.

The detection module 10 is configured to receive electrical activities of the brain and to convert the electrical activities into electrical signals. The detection module may be a transducer or a plurality of transducers converting the electrical activities of the brain into electrical signals. The brain electrical activities are the dynamic changes during the polarization and repolarization processes in neurotransmissions. When a transducer is applied on a region of the head, the transducer is able to detect the summation of the far field effects. The transducer may be a biopotential electrode to detect the electrical potentials or a magnetoelectric transducer to detect the magnetic fields. A ground electrode may be paired with the biopotential electrodes for measuring electrical potential differences and additionally a reference electrode may be presented for noise reduction. The detection module 10 may be applied on the surface of scalp to detect EEG or on the surface of the cortical brain to detect ECoG. In one example, the detection module 10 comprising an array of transducers may be arranged as a 10-20 system or other higher resolution systems. The biopotential electrodes could be wet (with saline water or conducting gels) or dry electrodes.

The detection module 10 may further comprise a data acquisition module. The data acquisition module may instruct a sampling rate to determine the time interval of the adjacent data points. The detected signal may be acquired and stored by a data acquisition module in the form of electrical potential (preferably measured by voltage) with corresponding temporal sequences.

The transmission module 20 is configured to receive the electrical signals from the detection module 10 and deliver the signals to the analysis module 30. The transmission module 20 may be wired or wireless. The wired transmission module 20 may include an electrical conductive material delivering the detected signal directly to the analysis module 30 or to the storage module for processing by the analysis module 30 thereafter. The detected signal may be stored in a mobile device, a wearable device or transmitted wirelessly to a data processing station through RF transmitters, Bluetooth, Wi-Fi or the internet. The mobile device can be a smartphone, a tablet computer, or a laptop. The wearable device can be a processor-embedded wristband, a processor-embedded headband, a processor-embedded cloth, or a smartwatch. The modules of the system 1 may be electrically coupled within a compact device or may be located discretely and coupled together by wired or wireless communication network.

The analysis module 30 is configured to process the signal by a series of action. The analysis module 30 may be a single microprocessor, such as a general purpose central processing unit, an application specific instruction set processor, a graphic processing unit, a field-programmable gate array, a complex programmable logic device or a digital signal processor. The analysis module 30 may execute a non-transitory computer program product embodied in the computer-readable medium. The analysis module 30 may comprise multiple microprocessors or processing units to execute the computer program product embodied in the computer-readable medium, in order to perform different functional blocks of the entire analysis process.

The visual output module 40 is configured to display the graphical results of the information generated by the analysis module 30. The visual output module 40 may be a projector, a monitor, or a printer for projecting the analysis results. In the embodiments, the analysis result is a visual output with graphic representations, and can be displayed by the visual output module 40 on a color monitor, be printed out on a paper or an electronic file, or be displayed on a grayscale monitor.

Figure 2:
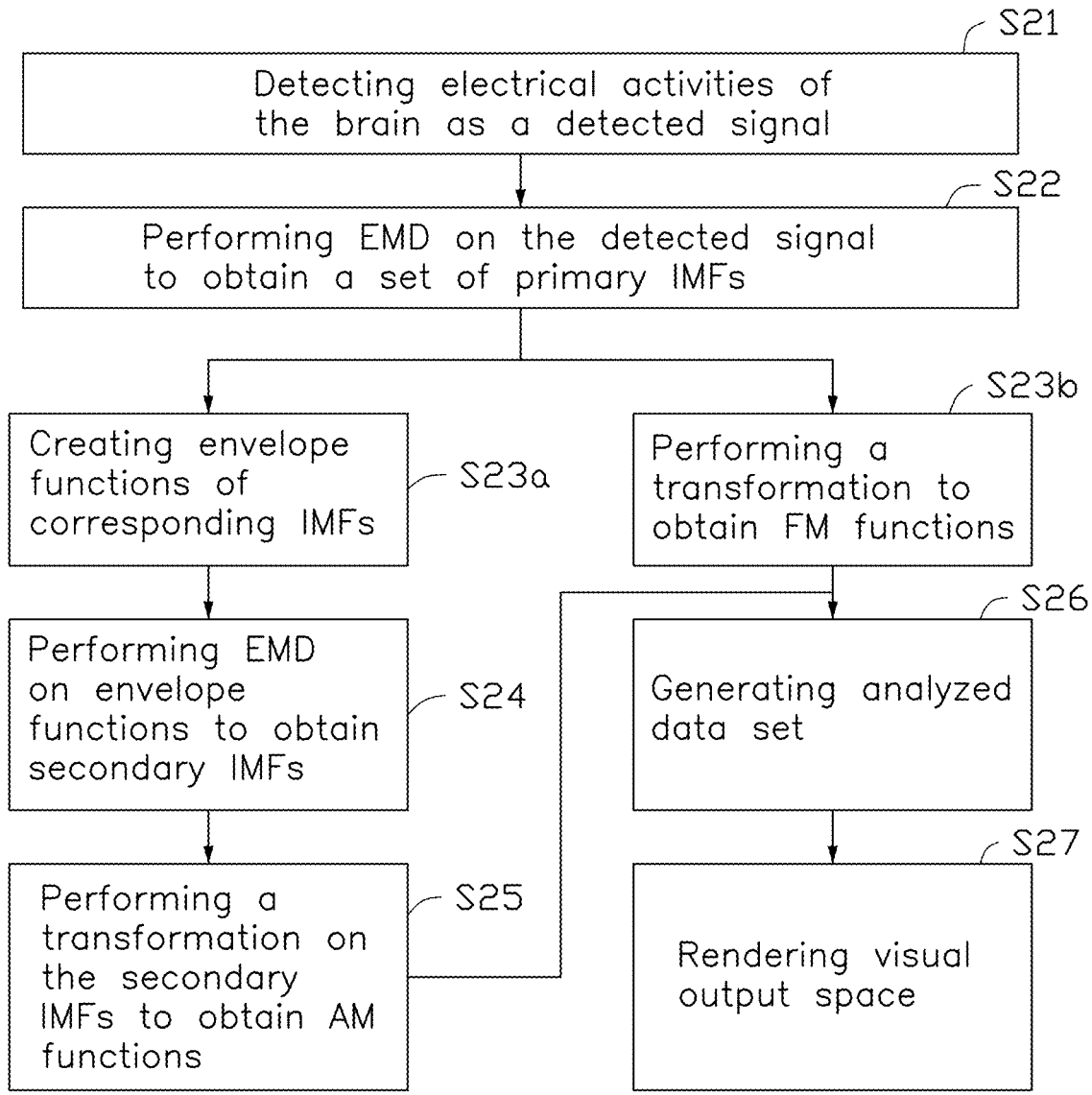
FIG. 2 is a flow diagram of a method for analyzing electrical activities of the brain in accordance with an embodiment of the present disclosure.

Referring to FIG. 2, a method for analyzing electrical activities of the brain in accordance with an embodiment of the present disclosure is provided. The method for analyzing the electrical activities of the brain may include the steps as mentioned below. The method comprises: detecting the electrical activities of the brain as a detected signal S21, performing empirical mode decomposition (EMD) on the detected signal to obtain a set of primary intrinsic mode functions (IMFs) S22, creating envelope functions of the corresponding of IMF S23a, performing EMD on the envelope functions to obtain sets of secondary IMF S24, performing a transformation on the plurality of primary IMFs to obtain the frequency modulation (FM) functions S23b, performing a transformation on the plurality of secondary IMFs to generate the AM function S25, generating data set according to the FM function and the AM function S26, generating a visual output space S27. The EMD in S22 can be complete ensemble empirical mode decomposition (CEEMD), ensemble empirical mode decomposition (EEMD), masking EMD, enhanced EMD, multivariate empirical mode decomposition (MEMD), noise-assisted multivariate empirical mode decomposition (NA-MEMD). The transformation in S23b and S25 can be Hilbert transform, Direct quadrature, inverse trigonometric function, or generalized zero-crossing. Detecting the electrical activities of the brain as a detected signal S21 is performed at the detection module 10. The analysis module 30 generates the analyzed data set from the detected signal and the analyzed data set may be stored in the computer-readable medium in the analysis module 30 for a scheduled display on the visual output module 40 thereafter. The analyzed data set comprises a plurality of analyzed data units.

The processes S22, S23a, S23b, and S25 are further elaborated in FIGS. 3A to 3F, in accordance with an embodiment of the present disclosure. The detected signals are consequently transformed or decomposed into primary IMFs, secondary IMFs, envelope functions, AM functions, and FM functions.

Figure 3A:
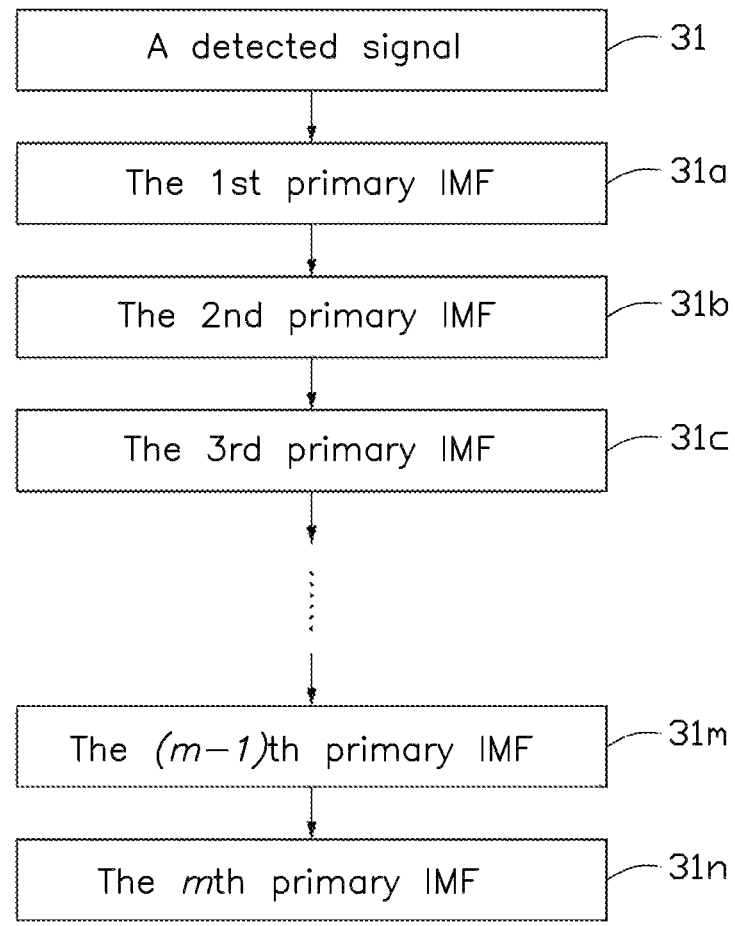
FIG. 3A is a flow diagram of transforming electrical activity signals into a set of primary intrinsic mode functions (IMFs) in accordance with an embodiment of the present disclosure.

Referring to FIG. 3A, a plurality of EMDs for detected signals are provided in accordance with an embodiment of the present disclosure. The detected signal is transformed into a set of primary IMFs by EMDs. The plurality of EMDs in FIG. 3A correspond to S22 of FIG. 2. The EMD is a process comprising a series of sifting process to decompose a signal into a set of IMFs. For example, a plurality of primary intrinsic functions is generated from the detected signal by EMD. A sifting process generates an intrinsic function from the detected signals. For example, a first sifting process generates a first primary IMF 31a from the detected signal 31; a second sifting process generates a second primary IMF 31b from the first primary IMF 31a; a third sifting process generates a third primary IMF 31c from the second primary IMF 31b; a mth sifting process generates a mth primary IMF 31n from the (m−1)th primary IMF 31m. The number of sifting processes is determined by stopping criteria. The stopping criteria may depend on the signal attenuation or the variation of the mth primary IMF 31n.

Furthermore, EMD may comprise masking procedure or noise (even pairs of positive and negative values of the same noise) addition procedure with variable magnitude adapted for each sifting step to solve mode mixing problems. EMD may be achieved by ensemble techniques.

Figure 3B:
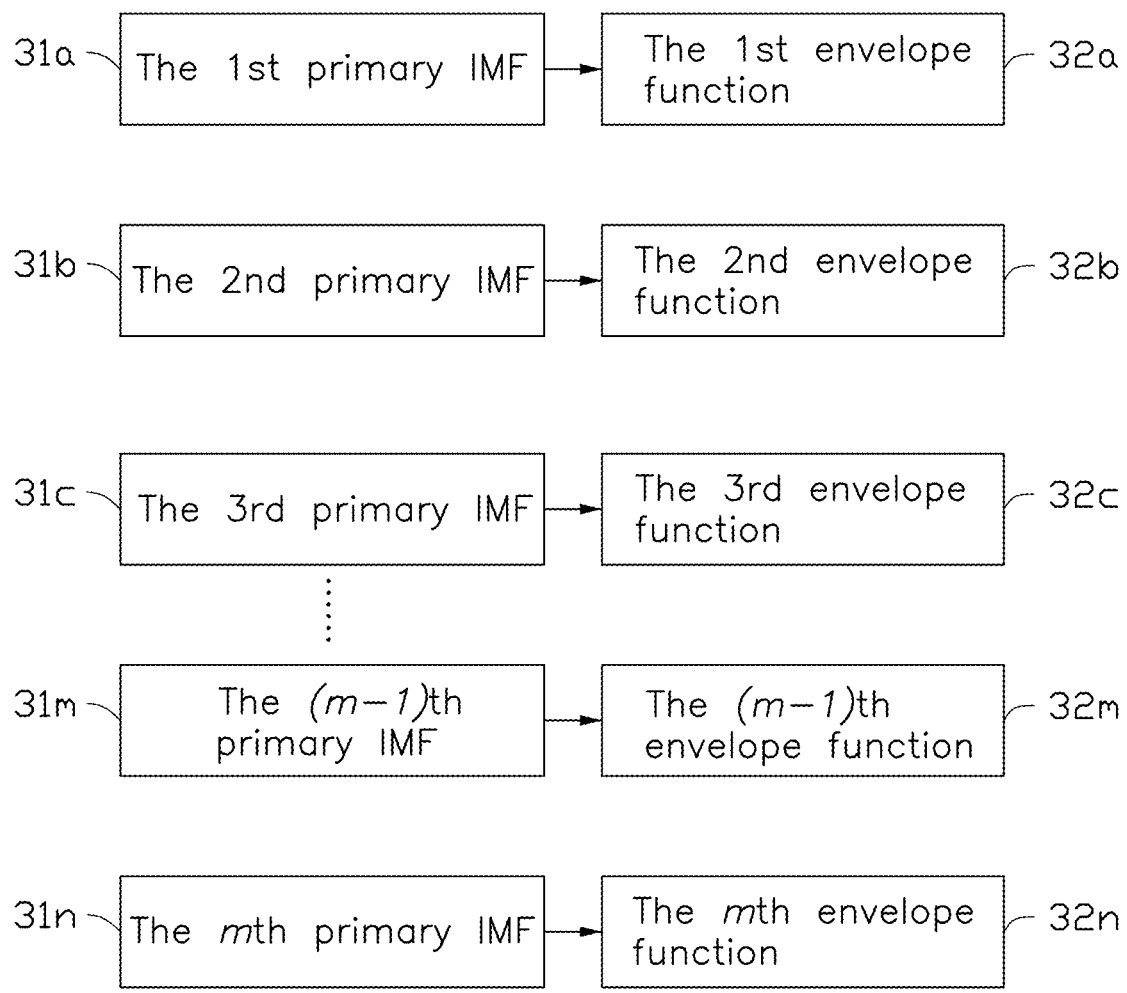
FIG. 3B is a flow diagram of an interpolation process in accordance with an embodiment of the present disclosure.

Referring to FIG. 3B, a plurality of interpolation processes is provided in accordance with an embodiment of the present disclosure. The interpolation processes in FIG. 3B correspond to S23a in FIG. 2. An envelope function is the interpolation function generated by an interpolation process from detected signals. The envelope function connects local extrema of the detected signals. Preferably, the envelope connects local maxima of the absolute-valued function of the detected signals. The interpolation process may be achieved via linear interpolation, polynomial interpolation, trigonometric interpolation or spline interpolation, preferably cubic spline interpolation. The envelope functions in FIG. 3B are generated from IMFs in FIG. 3A by the interpolation processes. A first envelope function 32a may be generated from the first primary IMF 31a; a second envelope function 32b may be generated from the second primary IMF 31b; a third enveloped function 32c may be generated from the third primary IMF 31c; a (m−1)th envelope function 32m may be generated from the (m−1)th primary IMF 31m; a mth envelope function 32n may be generated from the nth primary IMF 31n.

Figure 3C:
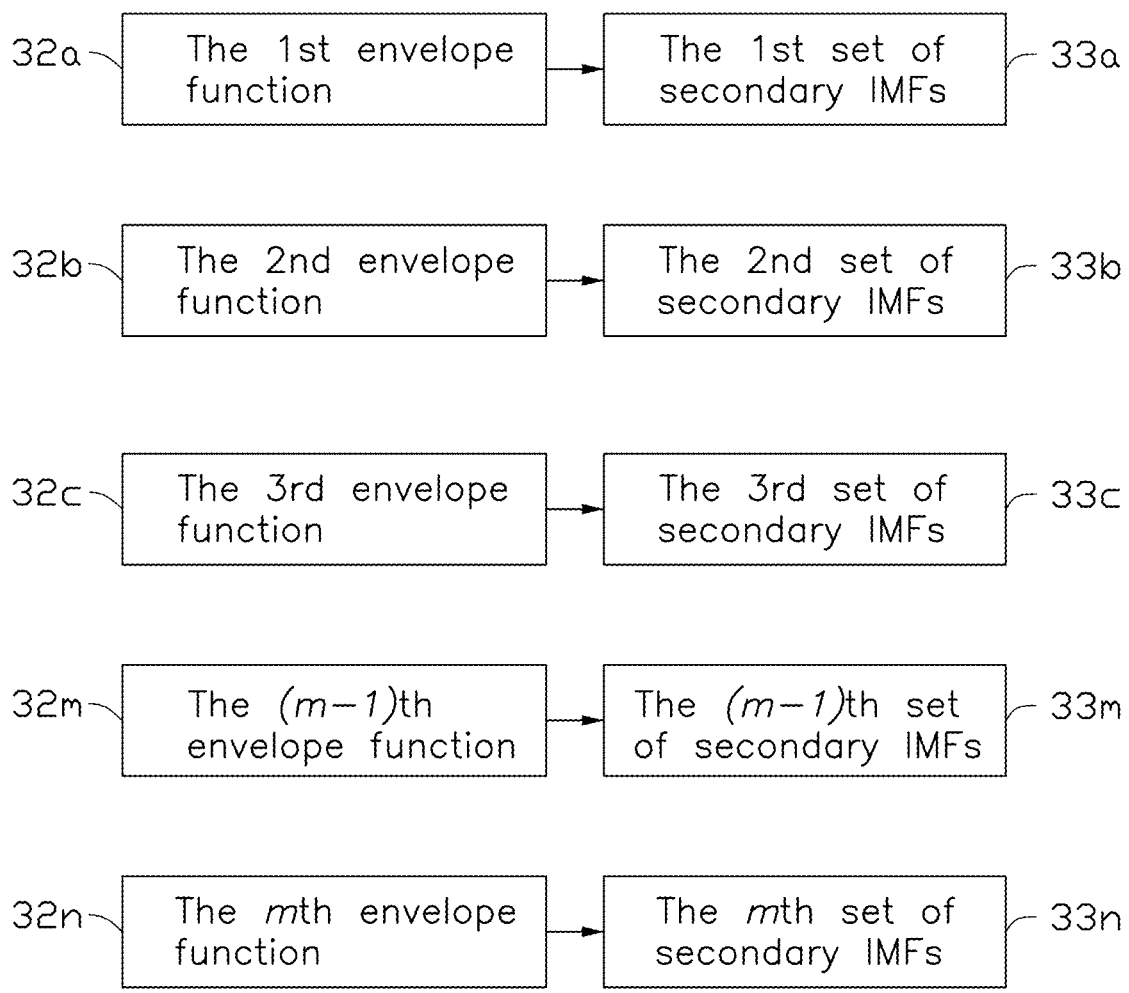
FIG. 3C is a flow diagram of empirical mode decomposition (EMD) in accordance with an embodiment of the present disclosure.

Referring to FIG. 3C, a plurality of EMDs is provided in accordance with an embodiment of the present disclosure. The plurality of sets of secondary intrinsic functions is generated from the envelope functions by EMD. The EMDs in FIG. 3C correspond to S24 in FIG. 2. The first set of secondary IMFs 33a is generated from the first envelope function 32a; the second set of secondary IMFs 33b is generated from the second envelope function 32b; the third set of secondary IMFs 33c is generated from the third envelope function 32c; the (m−1)th set of the plurality of secondary IMFs 33m is generated from the (m−1)th envelope function 32m; the mth set of the plurality of secondary IMFs 33n is generated from the mth envelope function 32n.

Figure 3D:
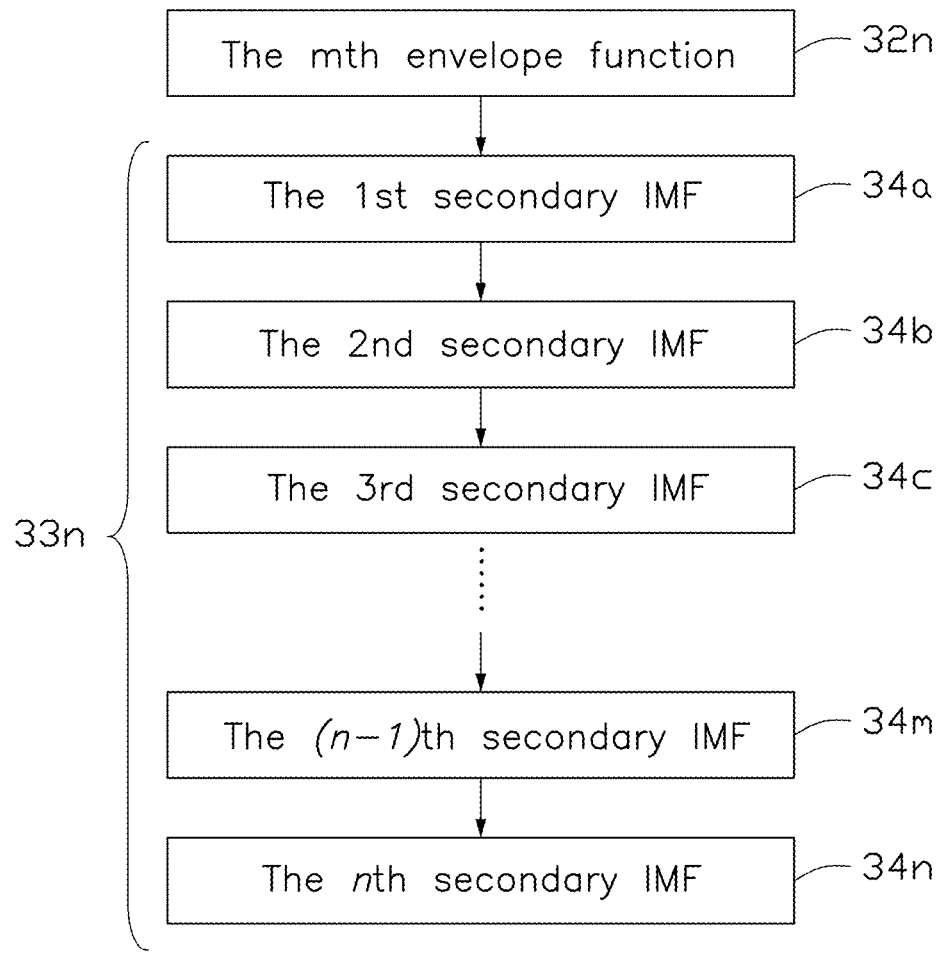
FIG. 3D is a flow diagram of secondary IMFs generated from envelope functions in accordance with an embodiment of the present disclosure.

Referring to FIG. 3D, a plurality of sets of secondary IMFs are provided in accordance with an embodiment of the present disclosure. The mth envelope function 32n, the mth set of secondary IMFs 33n, and the secondary IMFs included in the mth set of secondary IMFs 33n are illustrated in FIG. 3D. The mth envelope function 32n in FIG. 3B comprises a first secondary IMF 34a of the mth set of secondary IMFs 33n, a second secondary IMF 34b of the mth set of secondary IMFs 33n, a third secondary IMF 34c of the mth set of secondary IMFs 33n, a (n−1)th secondary IMF 34m of the mth set of secondary IMFs 33n, and a nth secondary IMF 34n of the mth set of secondary IMFs 33n. Therefore, there are IMFs in a number of m (number of the plurality of sets of secondary IMF) multiplying n (number of individual secondary IMFs in a set of secondary IMF in FIG. 3D.

Figure 3E:
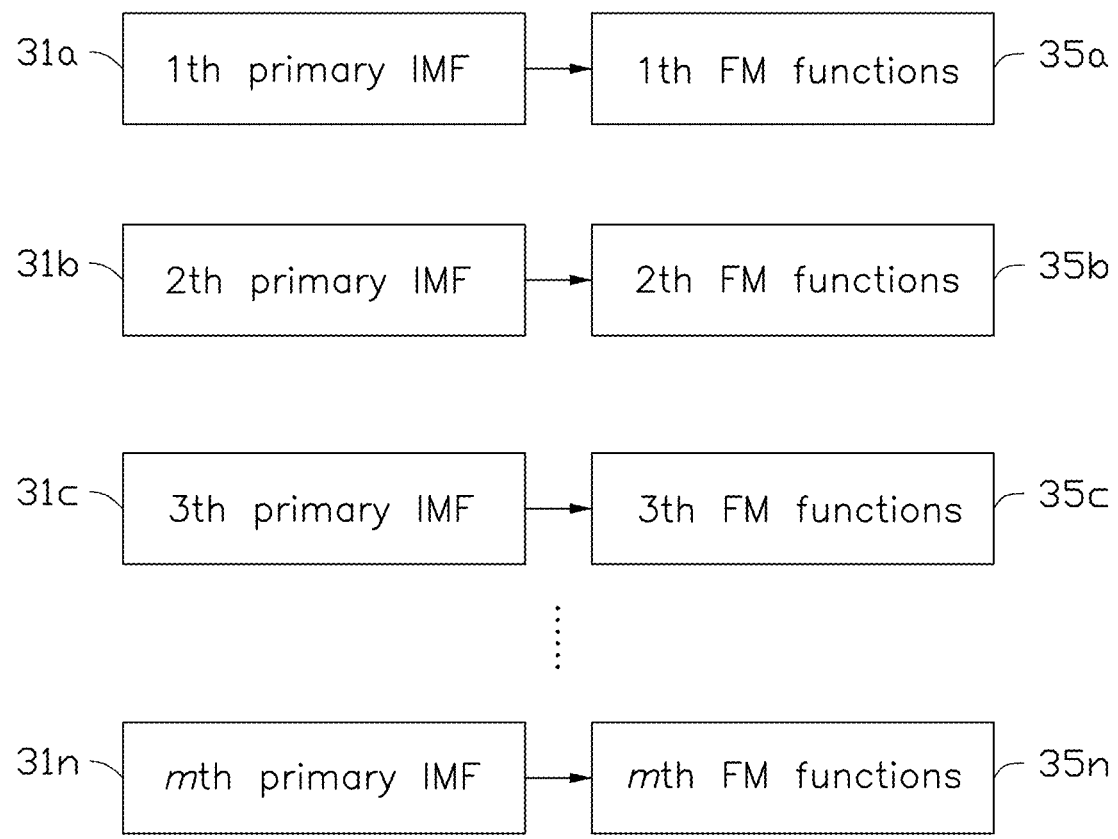
FIG. 3E is a flow diagram of transforming primary IMFs into frequency modulation (FM) functions in accordance with an embodiment of the present disclosure.
Figure 3F:
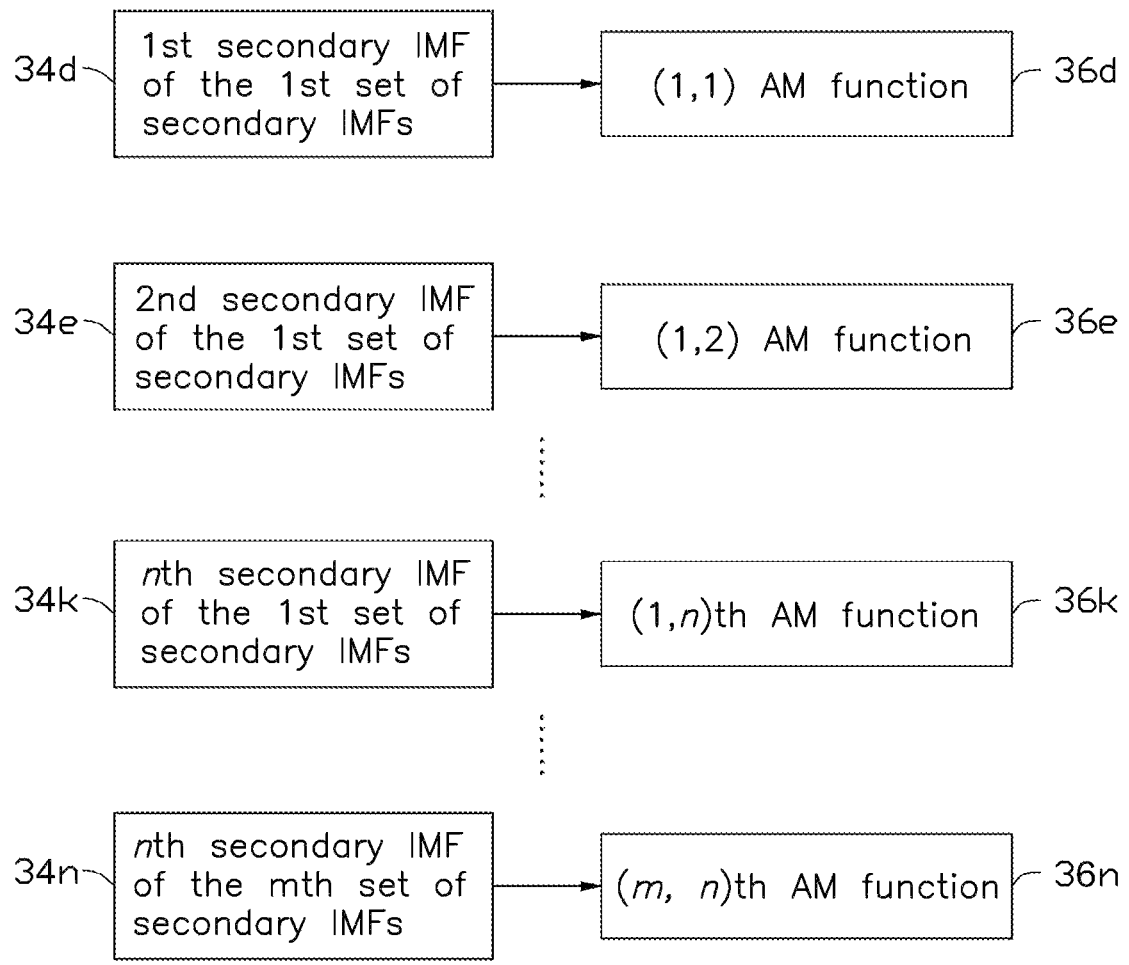
FIG. 3F is a flow diagram of transforming secondary IMFs into amplitude modulation (AM) functions in accordance with embodiments of the present disclosure.

Referring to FIG. 3E and FIG. 3F, a series of transformation processes is provided in accordance with an embodiment of the present disclosure. The transformation process is to convert a function from real domain to complex domain. The transformation process comprises at least a transformation and a complex pair function formation. The transformation process may be a Hilbert transform, a direct-quadrature-zero transform, an inverse trigonometric function transform, or a generalized zero-crossing transform. The complex pair function formation is to combine the function as the real part of the complex pair function and the transformed function as the imaginary part of the complex pair function.

In FIG. 3E, the FM functions are the complex pair functions generated from the plurality of primary IMFs by a proper transformation process. The transformation processes in FIG. 3E correspond to S23b in FIG. 2. The first primary IMF 31a is transformed into a first FM function 35a by the transformation process; the second primary IMF 31b is transformed into a second FM function 35b by the transformation process; the third primary IMF 31c is transformed into a third FM function 35c by the transformation process; and the mth primary IMF 31n is transformed into a mth FM function 35n by the transformation process.

In FIG. 3F, the AM functions are the complex pair functions generated from the secondary IMFs by a series of transformation processes. The transformation processes in FIG. 3F correspond to S25 in FIG. 2. The first secondary IMF 34d of the first set of secondary IMFs may be transformed into a (1,1) AM function 36d by the transformation process; the second secondary IMF 34e of the first set of secondary IMFs is transformed into a (1,2) AM function 36e by the transformation process . . . and the nth secondary IMF 34k of the first set of the secondary IMFs is transformed into a (1, n) AM function 36k by the transformation process. Furthermore, the nth secondary IMF 34n of the mth set of secondary IMFs may be transformed into a (m, n)th AM function 36n by the transformation process.

Figure 4:
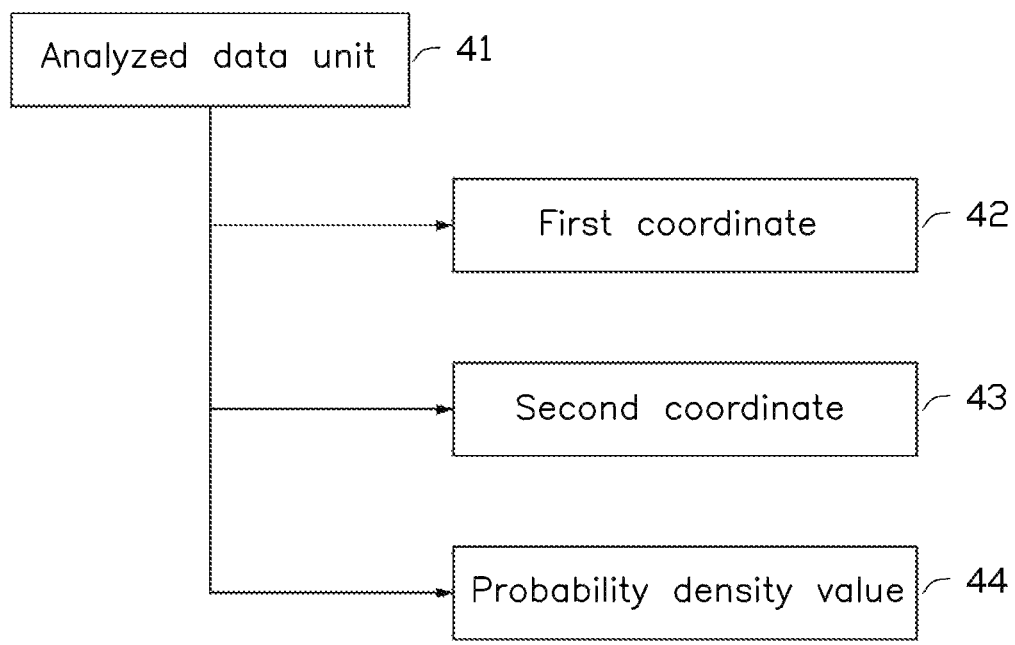
FIG. 4 is a schematic diagram of an analyzed data unit in accordance with an embodiment of the present disclosure.

Referring to FIG. 4, elements of an analyzed data unit is provided in accordance with an embodiment of the present disclosure. In FIG. 4, the analyzed data unit 41 comprises a probability density value 44, a first coordinate 42 and a second coordinate 43. The probability density function (PDF) is a probability density function of one subset of the IMFs. The probability density value 44 is the probability at a specific signal strength value or at a specific instantaneous frequency. In one example, the first coordinate 42 indicates the order number of one subset of the IMFs and the second coordinate 43 indicates the signal strength value. In another example, the first coordinate 42 indicates the instantaneous frequency and the second coordinate 43 indicates the z-value. The subset of IMFs may comprise one IMF component or the combination of at least two different IMF components. The signal strength value may indicate signal amplitude measured by electrical potential (voltage) or electrical current (ampere) or may indicate signal energy measured by energy strength per unit time interval (watt). In some examples, the instantaneous frequency or the specific signal strength value may be centralized by mean and normalized by standard deviation.

The visual output space comprising a first axis, a second axis and a plurality of visual elements. Each visual elements may include one or more analyzed data units within a certain range formed by the subsets of IMFs and the probability density value. The visual output module renders visual output space according to the analyzed data set. It is contemplated that a smoothing process may be applied to the visual output space for those visual elements with sparse data units.

A smoothing process may be applied to the visual output space for the visual elements. The smoothing process may be Butterworth filter, exponential smoothing, Kalman filter, Kernel smoother, Laplacian smoothing, moving average or other image smoothing techniques.

Following the methods, principles and transformation processes illustrated in FIG. 2, FIGS. 3A-3F, and FIG. 4, a plurality of embodiments are demonstrated in FIGS. 6A-6F, FIGS. 8A-8B, FIGS. 14A-14D, FIGS. 15A-15D, FIGS. 16A-16E, and FIGS. 17A-17D.

Figure 5:
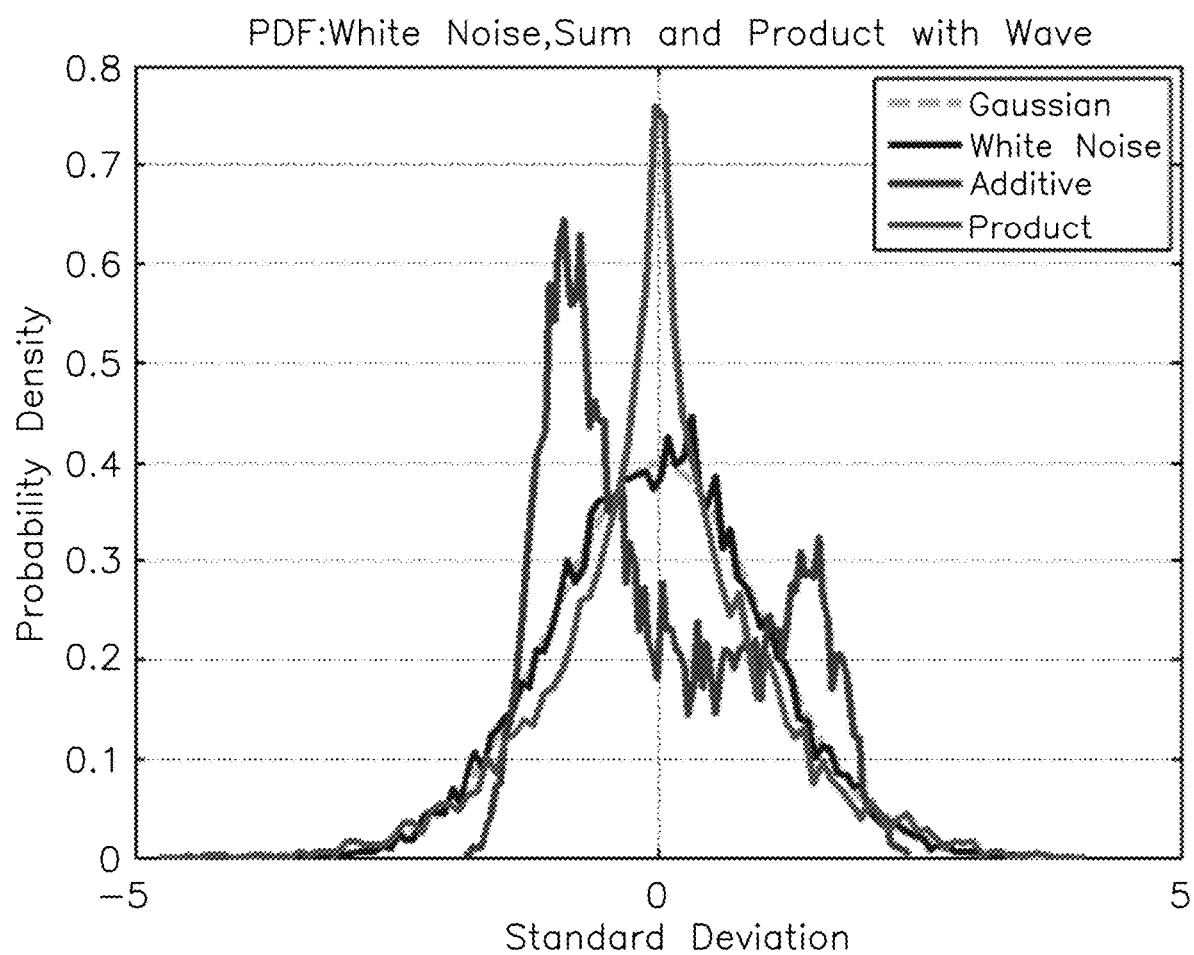
FIG. 5 is a conventional probability density function of white noise, Gaussian noise, the sum of the white noise and Gaussian noise, and the product of the white noise and Gaussian noise.

As shown in FIG. 5, a conventional probability density function of white noise, Gaussian noise and the sum of the white noise and Gaussian noise, and the product of white noise and Gaussian noise is provided. The white noise and Gaussian noise are generated from simulation data. The calibration used in FIG. 5 is demonstrated by using a white noise of 10,000 sample with a unity standard deviation value. A deterministic Stokes type wave is exemplified with the model: $y(t)=5*\cos[2*\pi*t/100+0.5*\sin(2*\pi*t/100)]$. FIG. 5 illustrates conventional PDFs for the white noise, the additive sum and the multiplicative products with the deterministic wave. Large amplitude of the deterministic Stoke type wave has overwhelmed the white noise to make the PDF of the sum bimodal, and the product super-Gaussian.

FIGS. 6A-6F and FIGS. 8A-8B are visual outputs of the iPDF, in accordance with one or more embodiments of the present disclosure. Each of the visual outputs in FIGS. 6A-6F and FIGS. 8A-8B comprise a first axis and a second axis. The first axis indicates the order numbers 1-11 of one subset of the IMFs, and each order number indicates an IMF component within a time interval. The second axis indicates signal strength values normalized by standard deviation. Each of the IMF component comprises a plurality of analyzed data units, and each of the analyzed data units comprises a probability density value, a first coordinate indicating the IMF component, and a second coordinate indicating the standard deviation. The grayscale on each of the analyzed data units represents the probability density value, with darker gray being probability density value of +0.1 or probability density value of −0.1, white being probability density value of 0, and intermediate grays between each of the above grays being intermediate probability density values.

Additionally, the probability density value in the visual outputs of iPDF may be represented by different colors, a grayscale, dot density, or screentone. In one embodiment, the dot density may be higher for a larger probability density value, and lower density for a smaller probability density value. In another embodiment, different colors may be used to indicate the probability density value: red color indicates probability density value of +0.1, blue color indicates probability density value of −0.1, white color indicates probability density value of 0, and intermediate colors between each of the above color indicate intermediate probability density values. In still another embodiment, the screentone with more grids may represent larger probability density value, and the screentone with more dots may represent smaller probability density value. Conversely, the different colors, grayscale, dot density, or screentone can have different meanings for various levels of the probability density value.

Figure 6A:
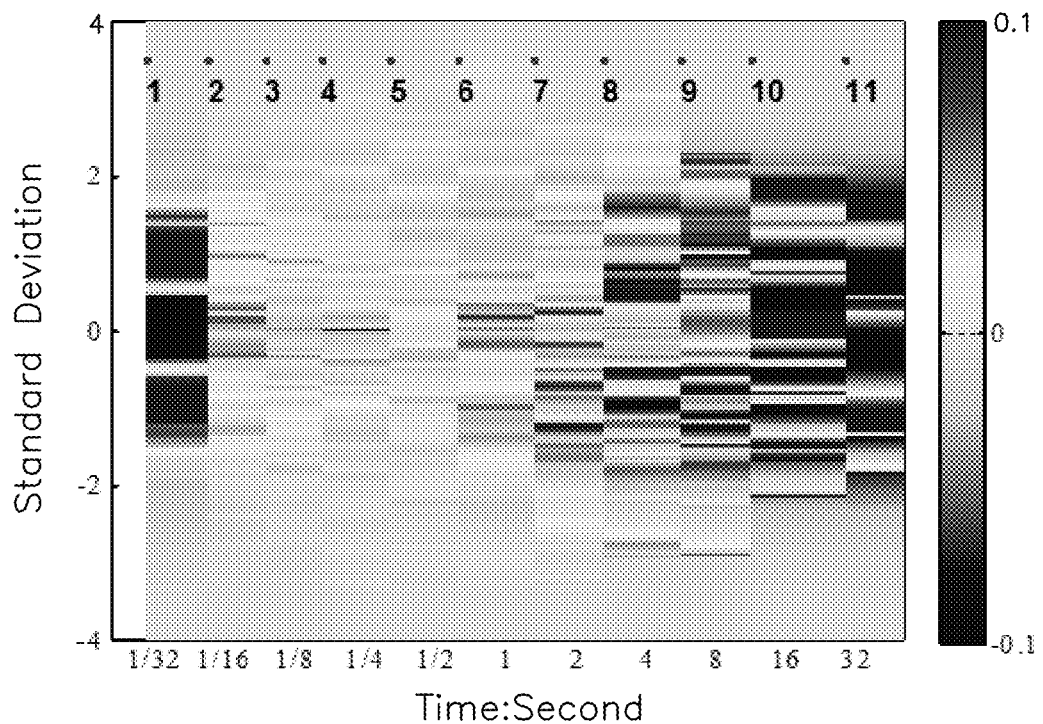
FIGS. 6A-6F are visual outputs of intrinsic probability density functions (iPDF) of the white noise, Gaussian noise, the sum of the white noise and Gaussian noise, and the product of the white noise and Gaussian noise, in accordance with embodiments of the present disclosure.

Referring to FIG. 6A, a visual output of the iPDF of the Gaussian white noise is presented with IMF components, in accordance with an embodiment of the present disclosure. Each column is an IMF component, and each of the IMF component should have similar Fourier spectrum, but some of their iPDF could deviate drastically from the Gaussian because of the limited size of the sample, which make the last few IMFs lacks the sufficient degree of freedom. Of particular interest is the first IMF from the white noise, which represents the highest frequency waves near the Nyquist limit. Thus, each sample point is either a maximum or a minimum that makes the PDF of the first IMF decidedly bimodal.

Figure 6B:
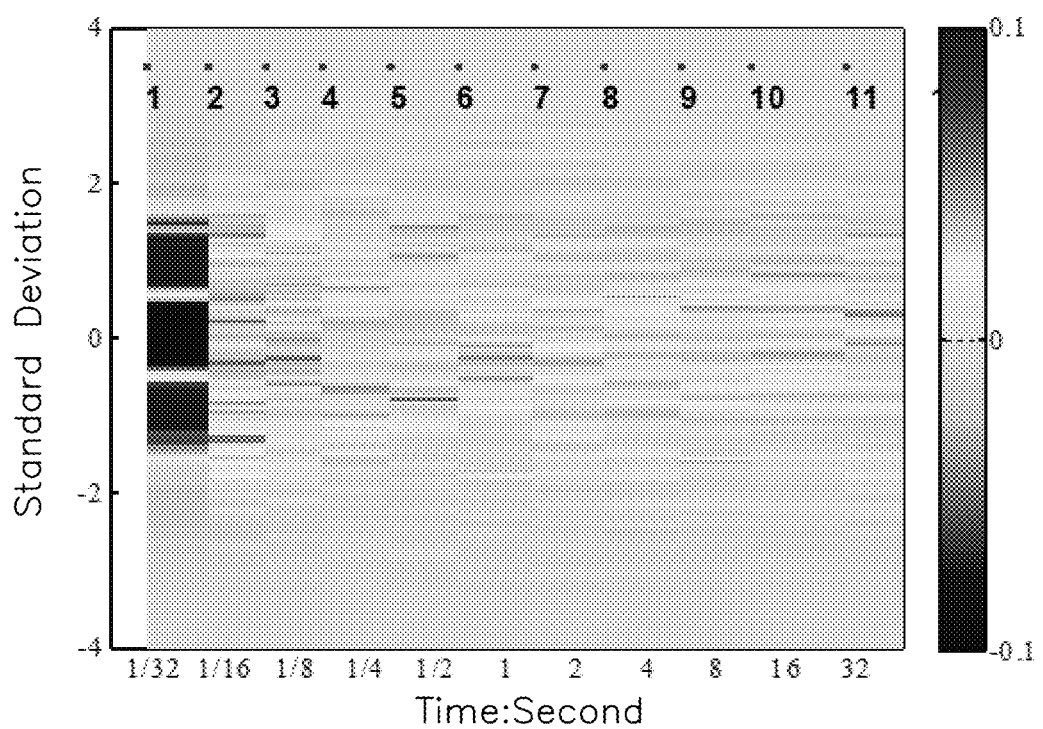

Referring to FIG. 6B, a visual output of the iPDF of partial sum of the white noise is presented with IMF components, in accordance with an embodiment of the present disclosure. Each subset of IMF comprises the sum of a plurality of IMFs. In FIG. 6B, the distributions plotted as a function of the time scale is uniformly Gaussian, except the first IMF is bimodal. The minor deviation shown here is the fluctuation due to the size of the sampling. Larger sample would produce smoother results as dedicated by the probability law. In FIG. 6B, the results indeed confirm the expectation for a white noise data, except the first IMF component.

Figure 6C:
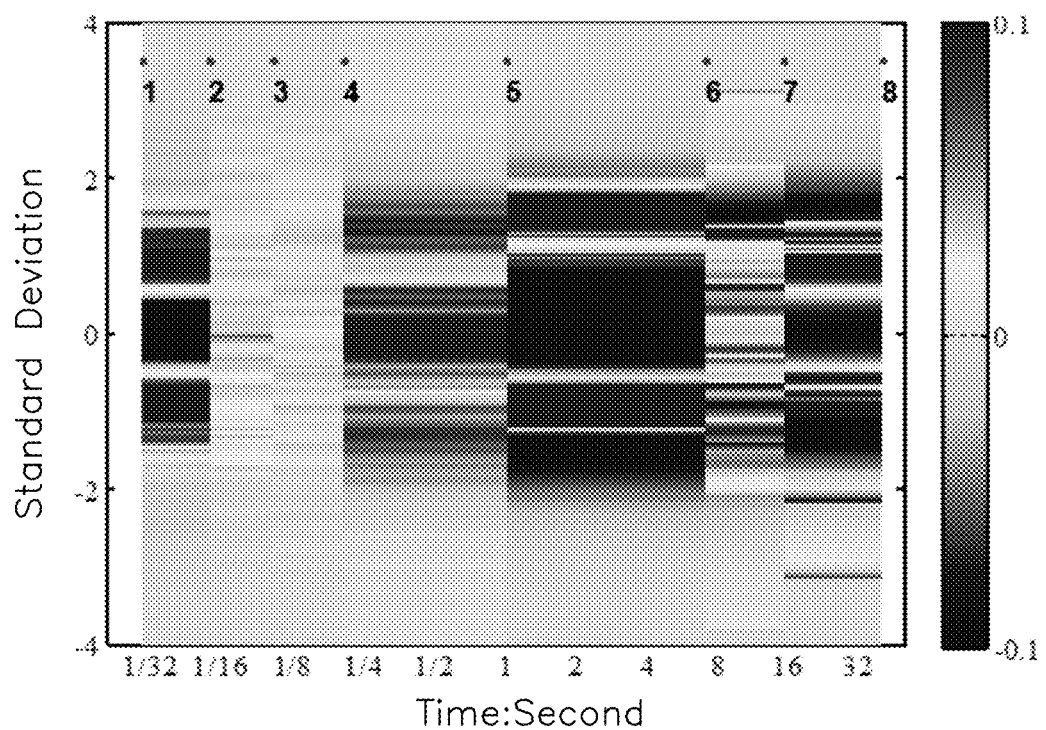

Referring to FIG. 6C, a visual output of the iPDF of the sum of the white noise and the deterministic Stokes type wave is presented with IMF components, in accordance with an embodiment of the present disclosure. The deterministic wave signal has a bimodal distribution. Other components in FIG. 6C are still near Gaussian, except that EMD leakage had caused some fluctuations.

Figure 6D:
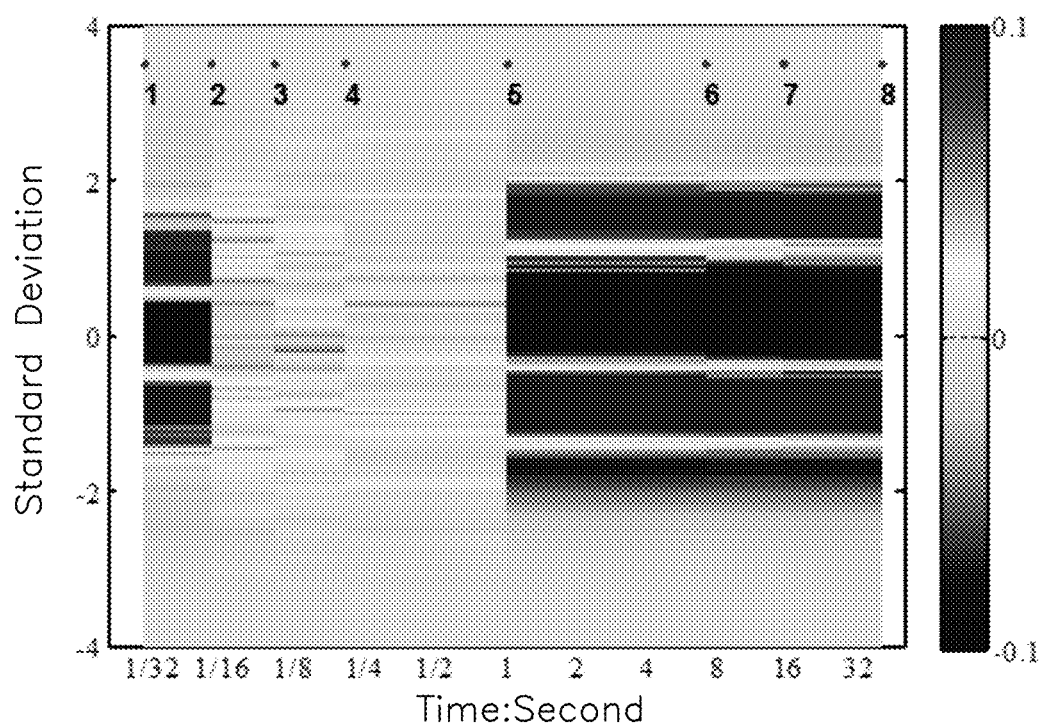

Referring to FIG. 6D, a visual output of the iPDF of the partial sum of the white noise and the deterministic Stokes type wave is presented with IMF components, in accordance with an embodiment of the present disclosure. In FIG. 6D, the distribution for the first IMF is still bimodal; the next three partial sums are nearly Gaussian as expected. The distribution changes abruptly at the fifth partial sum, when the deterministic Stokes type wave comes into the sum. As its magnitude is overwhelming, all the partial sums thereafter are all identically bimodal.

Figure 6E:
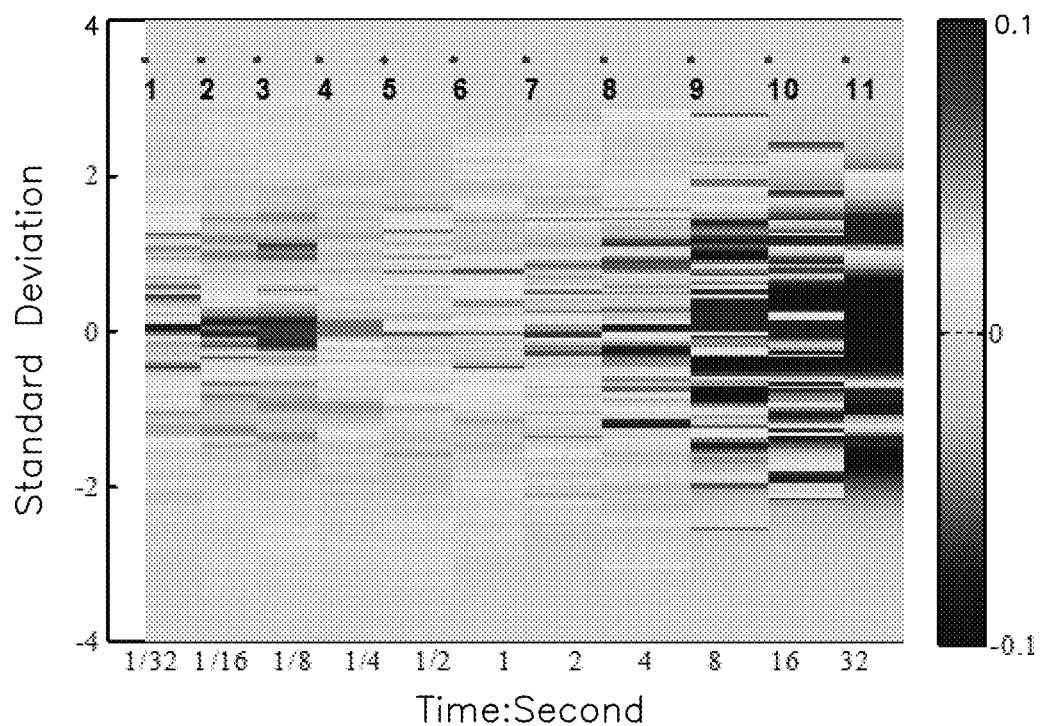

Referring to FIG. 6E, a visual output of the iPDF of the product of the white noise and the deterministic Stokes type wave is presented with IMF components, in accordance with an embodiment of the present disclosure. The iPDF is similar to the iPDF of white noise as shown in FIG. 6A except that the PDF of the first IMF is no longer bimodal. The modulation of a deterministic Stokes type wave has modified the range of the amplitude of the three point waves and render them nearly Gaussian distributed. The modulation effect on all the other IMFs is to make the next three IMFs slightly super-Gaussian.

Figure 6F:
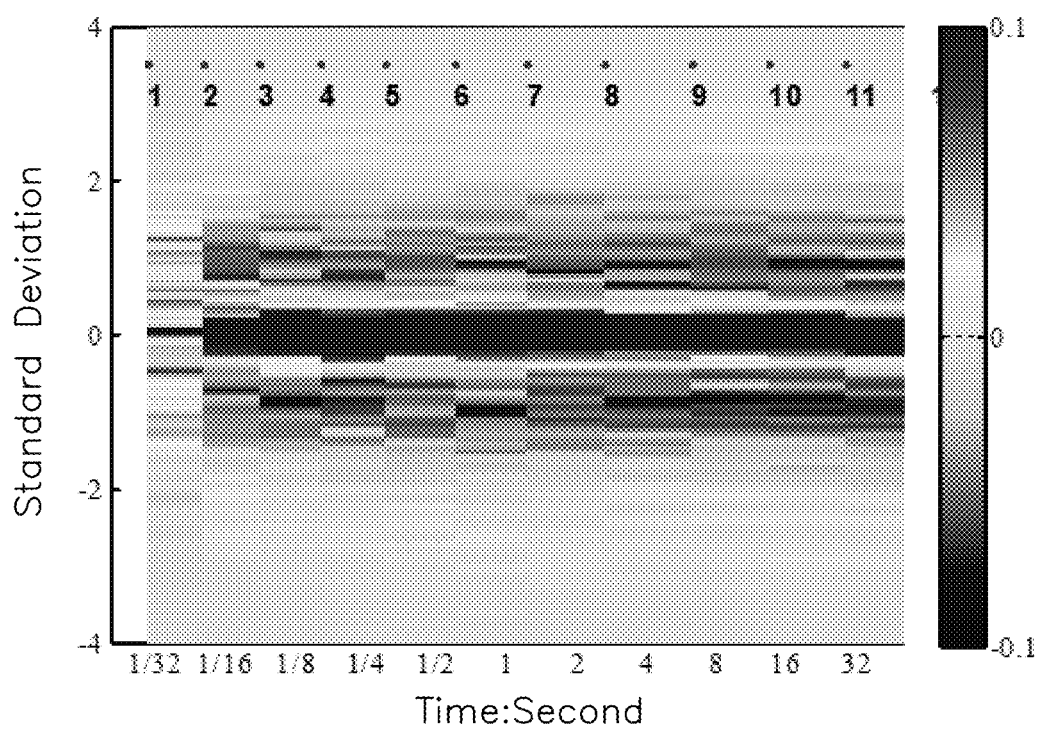

Referring to FIG. 6F, a visual output of the iPDF of the product of the white noise and the deterministic Stokes type wave is presented with IMF components, in accordance with an embodiment of the present disclosure. The iPDF are all highly super-Gaussian through all the time scales. The drastic difference between the additive and the multiplicative processes is clear: linear additive processes is simply superposition without any interactions between the wave and the white noise. The influence of the deterministic wave may show up when the scale reaches the wave period locally. The multiplicative process may influence all the IMF components globally. Also, the multiplicative process may produce a global super-Gaussian distribution.

Figure 7A:
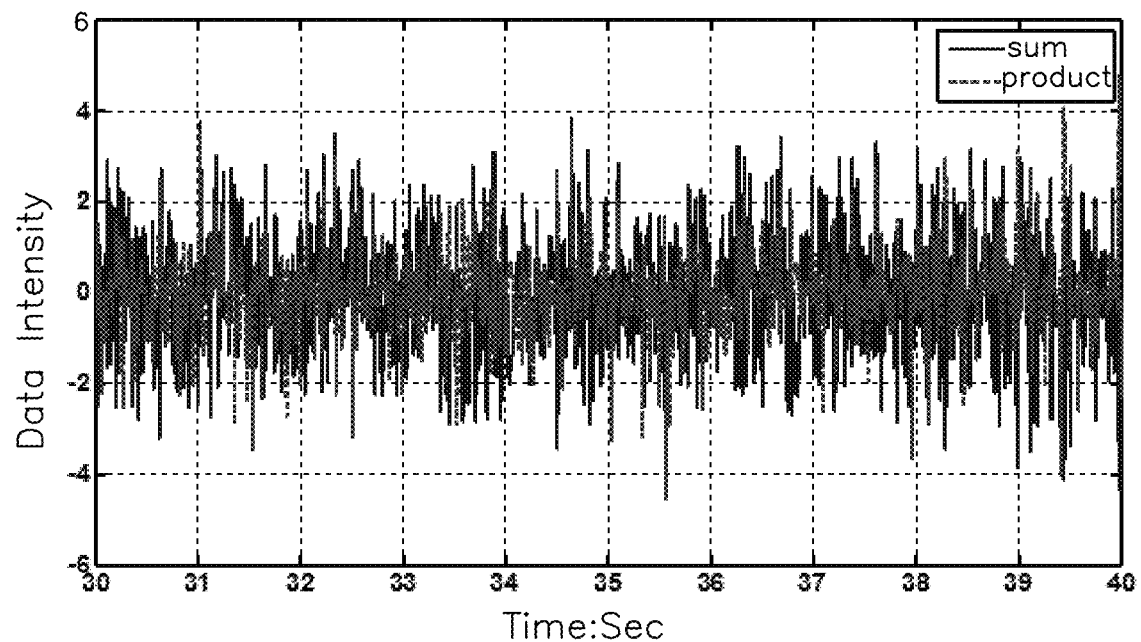
FIG. 7A is a conventional time-intensity chart of additive and multiplicative effects of the product and sum of the white noise.

Referring to FIG. 7A, the additive and multiplicative effects of two Gaussian distributed white noise signals are presented. It is difficult to distinguish between the additive and multiplicative processes by the morphology of the signals presented in time domain.

Figure 7B:
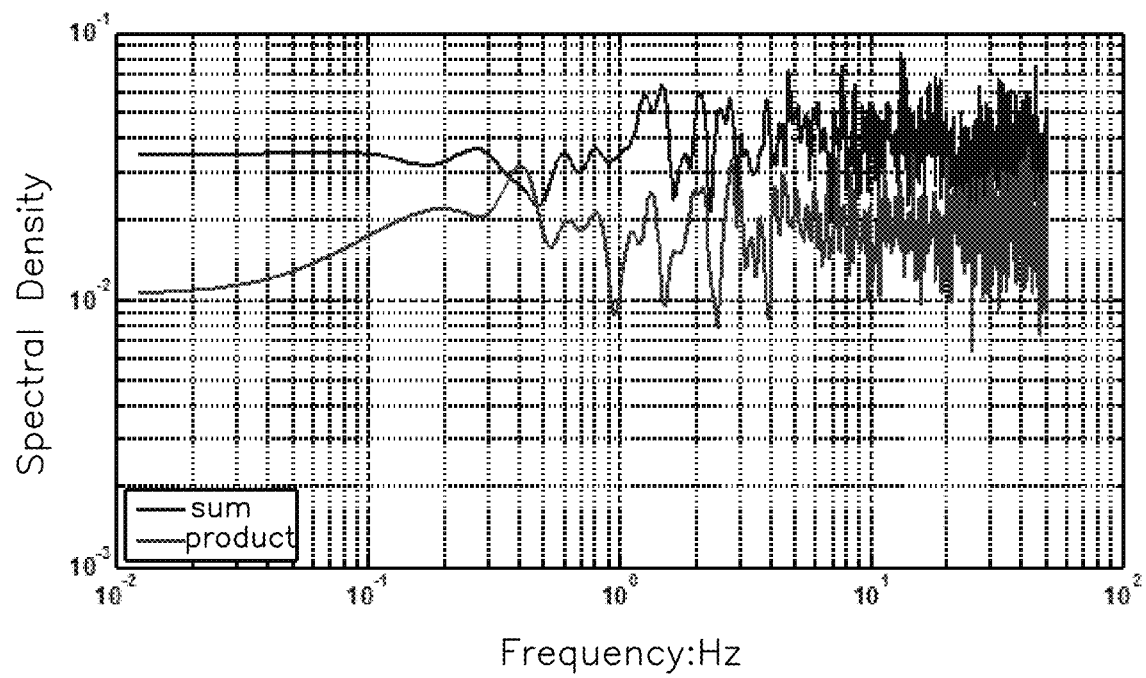
FIG. 7B is a conventional Fourier spectra of additive and multiplicative effects of the product and sum of the white noise.

Referring to FIG. 7B, the Fourier spectra of the additive and multiplicative effects of two Gaussian distributed white noise signals are presented. Both spectra have a white spectral form. Therefore, from the Fourier spectral form, it is difficult to tell the difference between additive and multiplicative processes.

Figure 8A:
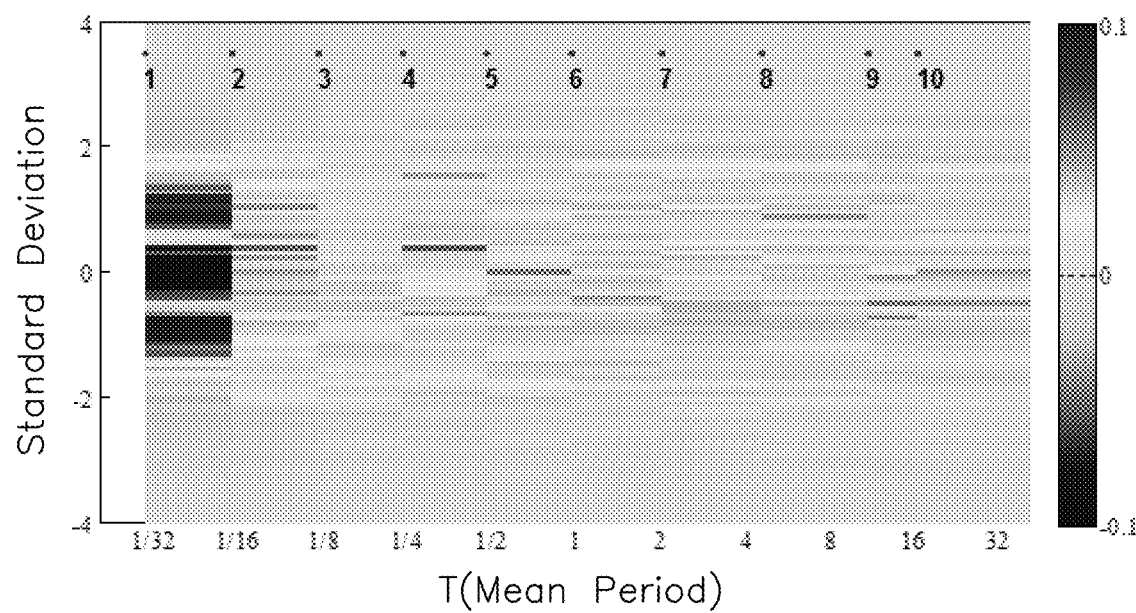
FIGS. 8A-8B are visual outputs of iPDF of the product and sum of the white noise, in accordance with an embodiment of the present disclosure.

Referring to FIG. 8A, a visual output of the iPDF of the additive effects of two Gaussian distributed white noise signals are presented, in accordance with an embodiment of the present disclosure. The distribution is Gaussian except the first IMF.

Figure 8B:
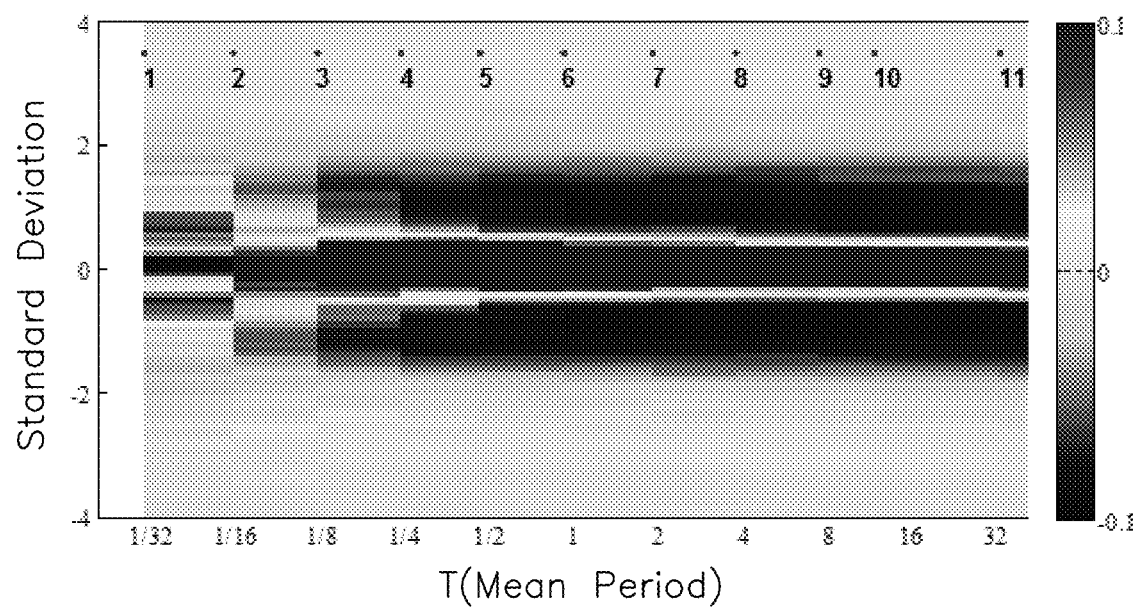

Referring to FIG. 8B, a visual output of the iPDF of the multiplicative effects of two Gaussian distributed white noise signals are presented, in accordance with an embodiment of the present disclosure. The distribution is decisively super-Gaussian.

The calibration in FIGS. 6A-6F and FIGS. 7A-7B shows that even for non-stationary processes, iPDF provides more information on the constituting components and the underlying mechanisms involved in the data generation processes: linear additive or nonlinearly multiplicative.

In the present disclosure, intrinsic multi-scale sample entropy (iMSE) may be applied for measurement of signal complexity. The complexity of each IMFs in different scales is useful for distinguishing among various physiological or disease states. The following examples are illustrated with EEG signals but not limited to what are presented.

Figure 10:
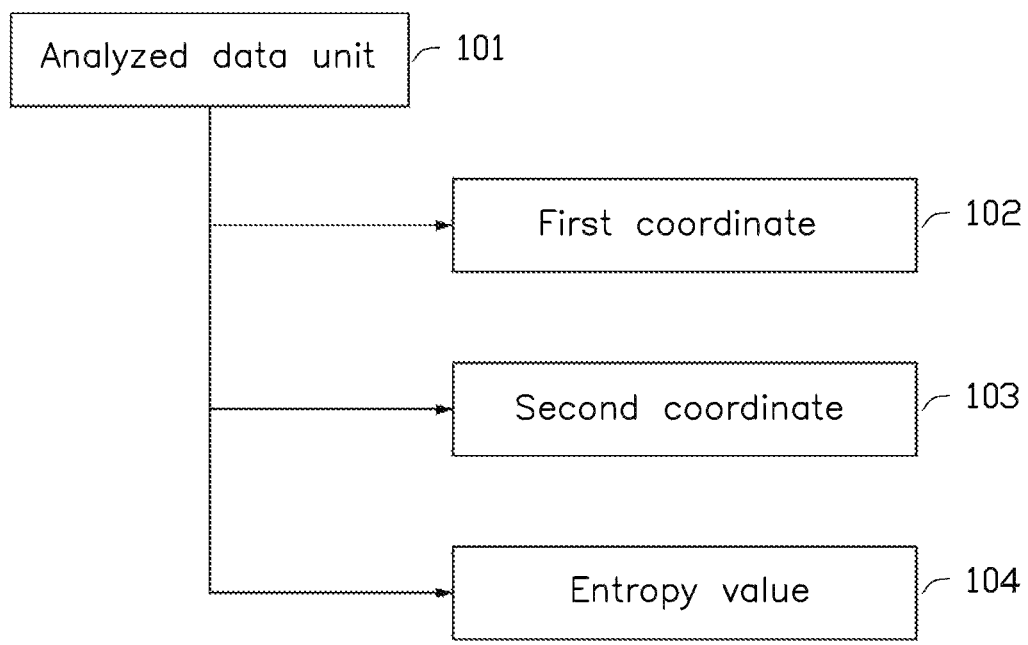
FIG. 10 is another schematic diagram of an analyzed data unit in accordance with an embodiment of the present disclosure.

Referring to FIG. 10, elements of another analyzed data unit are provided in accordance with an embodiment of the present disclosure. In FIG. 10, the analyzed data unit 101 comprises a first coordinate 102, a second coordinate 103, and an entropy value 104. The entropy value 104 may be a sample entropy value or an approximate entropy value. The sample entropy value is calculated according to one subset of the IMFs at a designated scale parameter. In one example, the first coordinate 102 indicates the order number of one subset of the IMFs. The second coordinate 103 indicates the scale parameter. The subset of IMFs may comprise one IMF component or the combination of at least two different IMF components.

The visual output space comprising a first axis, a second axis and a plurality of visual elements. Each visual elements may include multiple analyzed data units within a certain range formed by the subsets of IMFs and the entropy value. The visual output module renders visual output space according to the analyzed data set. A smoothing process may be applied to the visual output space for those visual elements with sparse data units.

Figure 11:
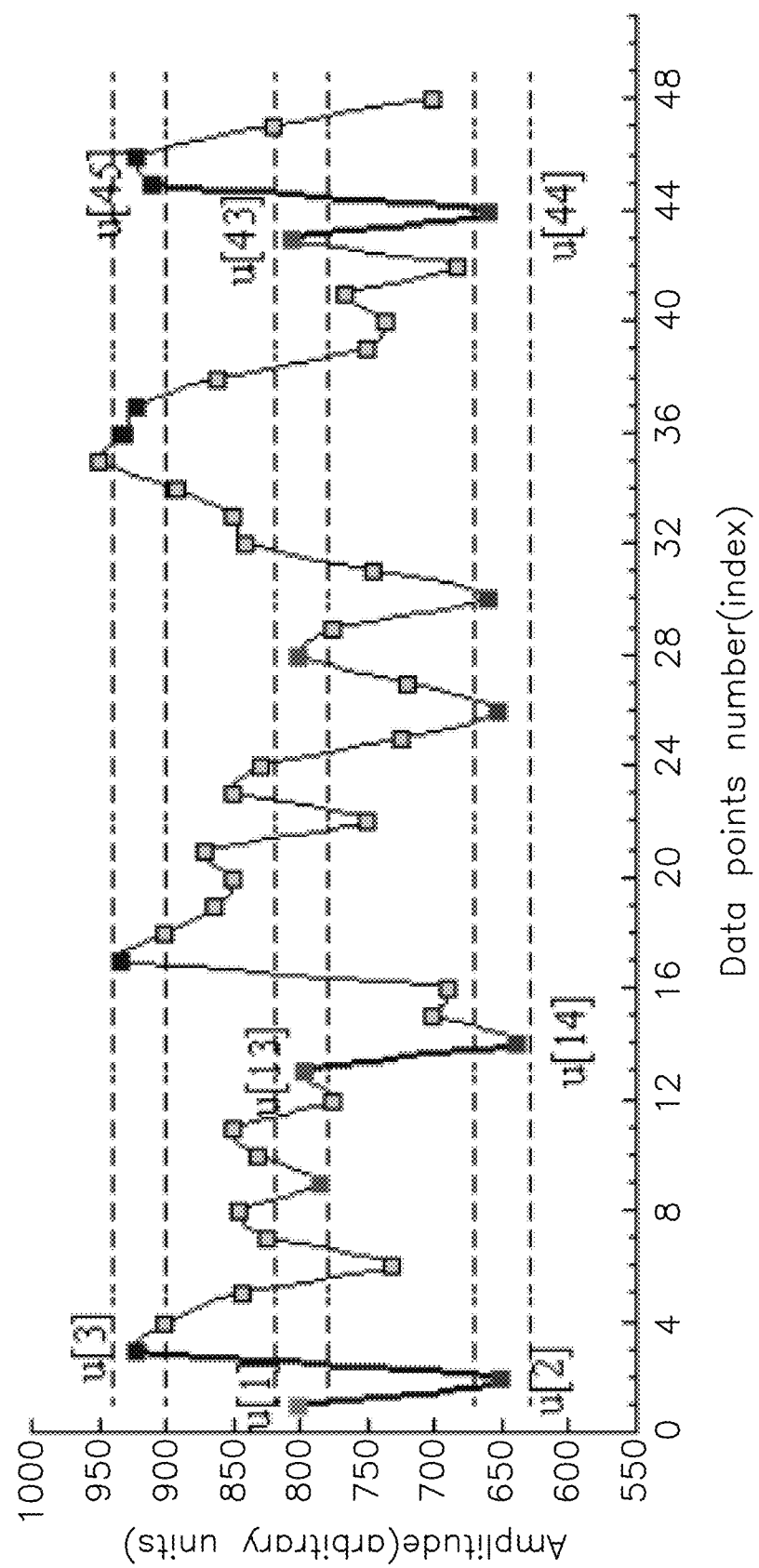
FIG. 11 is a calculation of sample entropy.

In FIG. 11, the sample entropy of a signal may be calculated as: log (patterns of length m)–log (patterns of length m+1). The scale parameters may be adjusted for calculating sample entropy values at different scale parameters.

According to an embodiment of the present disclosure, MSE is based on approximate Entropy of a given data, $X=\{x_i, \text{ for } i=1 \ldots n\}$, defined as $$E(X) = -\sum_{x_i \in \Theta} p(x_i) \log p(x_i), \quad (1)$$

where $p(\cdot)$ is the probability density function of a set of random numbers, $\Theta$. The MSE is defined as the joint entropy for a set of indexed sequence of n random variables, $\{X_i\}=\{X_1, \ldots, X_n\}$, with a set of values $\Theta_1, \ldots, \Theta_n$, respectively:

$$E_n = -\sum_{x_1 \in \Theta_1} \ldots \sum_{x_n \in \Theta_n} p(x_1, \ldots, x_n) \log p(x_1, \ldots, x_n), \quad (2)$$

where $p(x_1, \ldots, x_n)$ is the joint probability of the random variable, $X_1, \ldots X_n$. As the MSE is defined in terms of probability density function, it requires the existence of a mean and a variance of the data. Schematically, the method is illustrated in FIG. 2.1 (Costa et al, 2005). The probabilistic measure requirements limited the application of MSE to stationary data only.

Within the Multi-scale Intrinsic Entropy (iMSE) analysis provided by the present disclosure, the EMD is the tool to remove the trend of various scales systematically, for EMD endowed the resulting IMF's to have this special property. The process is provided by the present disclosure as follows:

When any non-stationary and nonlinear is decomposed in Intrinsic Mode Functions (IMF's) through EMD, there is $$x(t) = \sum_{j=1}^{n} c_j(t), \quad (3)$$

where each $c_j(t)$ is an IMF except the last one, which might be a trend if there is one. By definition, each IMF should be dyadically narrow band, symmetric with respect to zero-axis, and having the same numbers of extrema as the of zero-crossings. Furthermore, by construction, the IMF component $c_{j+1}$ is essentially derived from the trend of $c_j$. Taking advantage of these properties, Yeh et al (2015 and 2016) defined the Kolmogorov-Sinai (KS) type entropy for the specific intrinsic mode function as $$\Delta E_k = E_{k+1} - E_k \text{ where} \quad (4)$$

$E_k$ is defined as the partial sum of $IMF$: $\sum_{j=1}^{k} c_j(t)$.

Though the KS-type entropy is essentially the approximate the entropy of the single IMF component, the above definition is necessary to represent the influence of all other IMF's in the system, for the EMD expansion is nonlinear. Thus, this definition would include some nonlinear summation effects, albeit incompletely. The KS-type entropy has successfully revealed the scale dependent variations and the contribution of each IMF component to the total entropy. However, the result shows no relationship with the properties of the total data as in the original MSE as a measure of the whole system. The original MSE essentially emphasizes the view of the trees rather than the whole forest. Therefore, it is impossible to make comparisons in the spirit of the original MSE. The present disclosure redefines a new Intrinsic MSE with the following steps:

1. Generating a set of IMF by the EMD. The EMD may be any of its variations such as EEMD, CREMD, AEMD, and other decomposition methods. One example is given in Equation (3).
2. Providing the first set of random variables as the ascending partial sums for k=1 . . . to n, $$X_k = \sum_{j=1}^{k} c_j(t). \quad (5)$$

3. Calculating the Approximate Entropy, $E_k$, for each $X_k$, for all k from 1 . . . to n.
4. Providing the second set of random variables as the descending partial sums also for k=1 . . . to n, $$Y_{n-k} = \sum_{j=k}^{n} c_j(t). \quad (6)$$

5. Calculating the Approximate Entropy, $F_k$, for each $Y_{n-k}$, for all k from 1 . . . to n.
6. Generating a two-dimensional plot comprising $E_k$ and $F_k$ in a sequential order. This final result is the new Intrinsic Multi-scale Entropy (iMSE).
7. Generating a topographic iMSE. In case data from spatially distributed multi-stations, a Topographic iMSE (TiMSE) can be constructed to represent the spatial and temporal variation of the underlying variation of the complexity condition.

In the form provided by the above steps, the iMSE and TiMSE would contain all the possible partial sums of the data in terms of EMD expansion, which would systematically detrend any data, stationary or non-stationary, and produce the full scale dependent MSE, temporally and spatially.

According to conventional physical science, the entropy is highest when the system represents a white noise. In the MSE analysis, however, only systems with a mixture of both long and short scale correlation would have the most complex entropy, or the highest entropy. Thus, the MSE is useful to quantify complexity in the living systems.

To illustrate the prowess of the new iMSE and TiMSE, simulated data and human physiologic data are used in the following examples.

Referring to FIGS. 12A-12I, a plurality of visual outputs for iMSE are provided in accordance with an embodiment of the present disclosure. In FIGS. 12A-12I, the horizontal axis is a scale of iMSE, and the vertical axis represents cumulative IMFs. The cumulative IMFs 1-1, 1-7, 1-13, 7-13, and 13 on the vertical axis in FIGS. 12A-12I use bi-directional methods to represent diverse characteristics of the cumulation processes: cumulation processes from high-frequency band or cumulation processes from low-frequency bands. The Fractional Gaussian noises (fGn) with different $_H$ indices is the signal data for demonstrating the usefulness of iMSE. The Fractional Gaussian noises is defined as a time series, $x_H(n)$, with index $_H$ for n= . . . , -2, -1, 0, 1, 2, . . . if and only if it is a zero-mean, Gaussian stationary process with a correlation given as $$RH(k) = \langle x_H(n) x_H(m+k) \rangle = \frac{\sigma^2}{2}[|k-1|^{2H} - 2|k|^{2H} + |k+1|^{2H}], \quad (7)$$

in which <a> is the expected value of a, and a is the root mean square of the signal. For special case when H=0.5, the correlation would be zero; the series reduces to white noise.

Figure 12A:
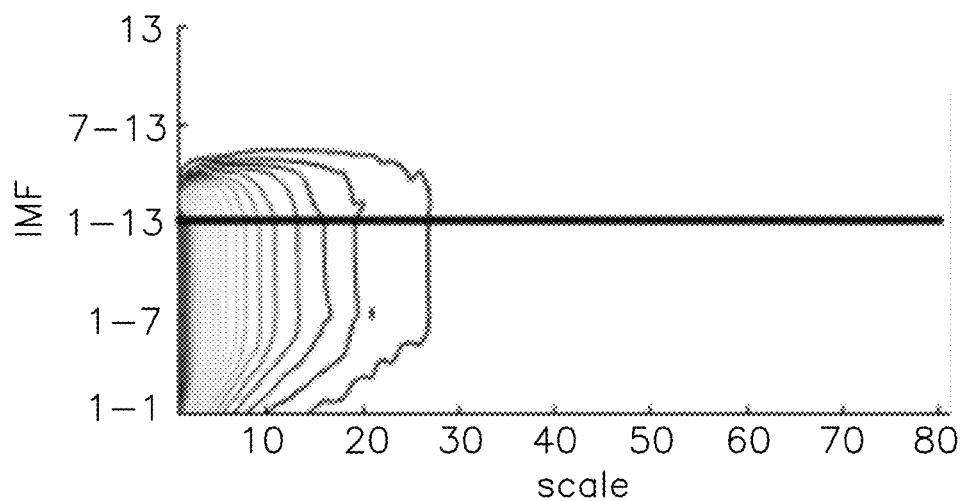
FIGS. 12A-12I are visual outputs of iMSE, in accordance with an embodiment of the present disclosure.
Figure 12B:
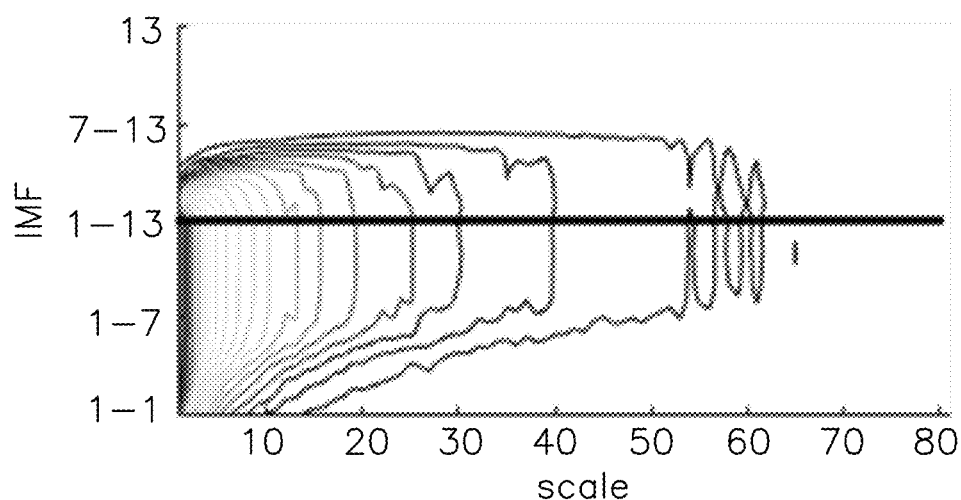
Figure 12C:
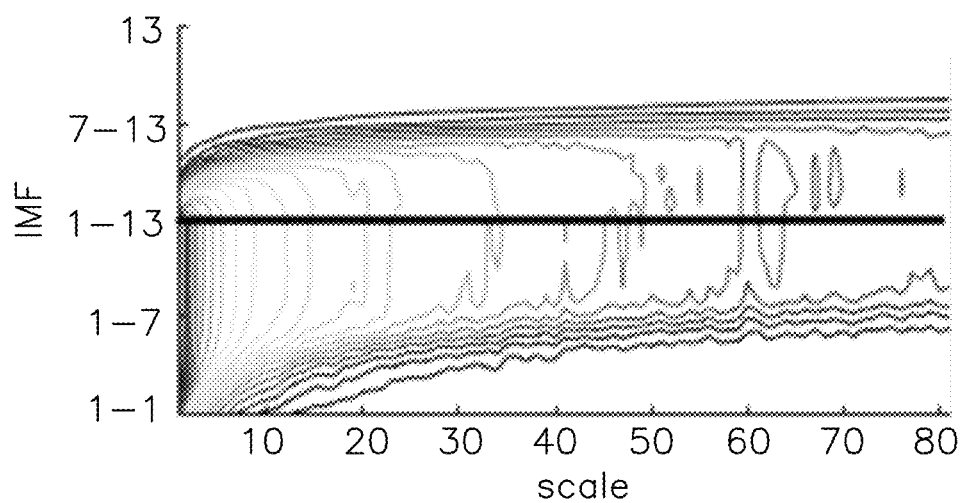
Figure 12D:
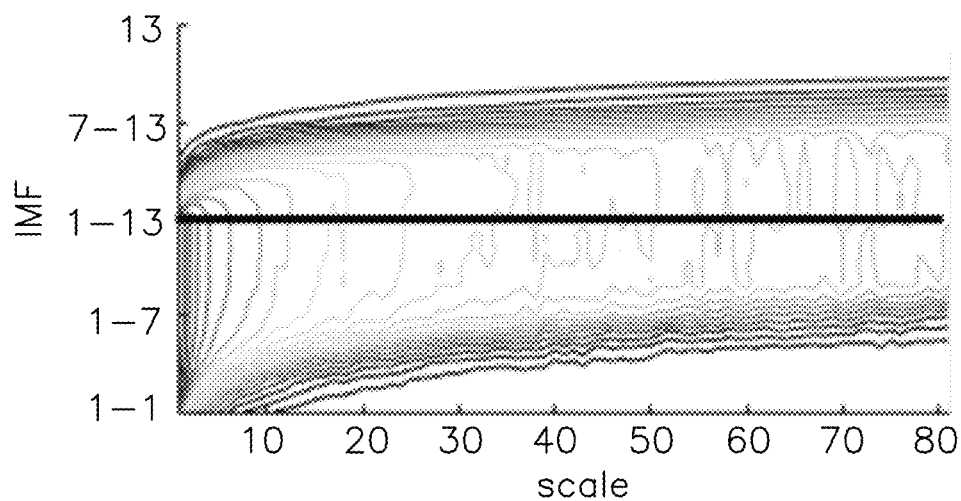
Figure 12E:
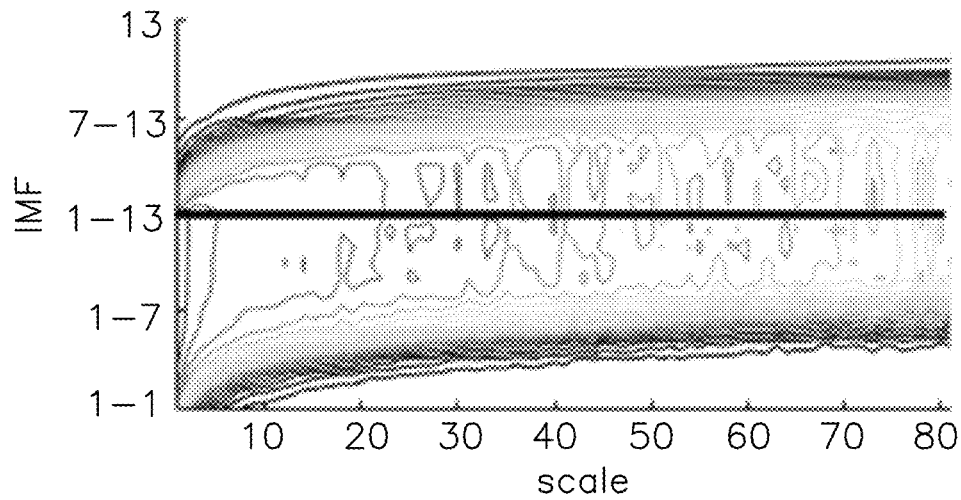
Figure 12F:
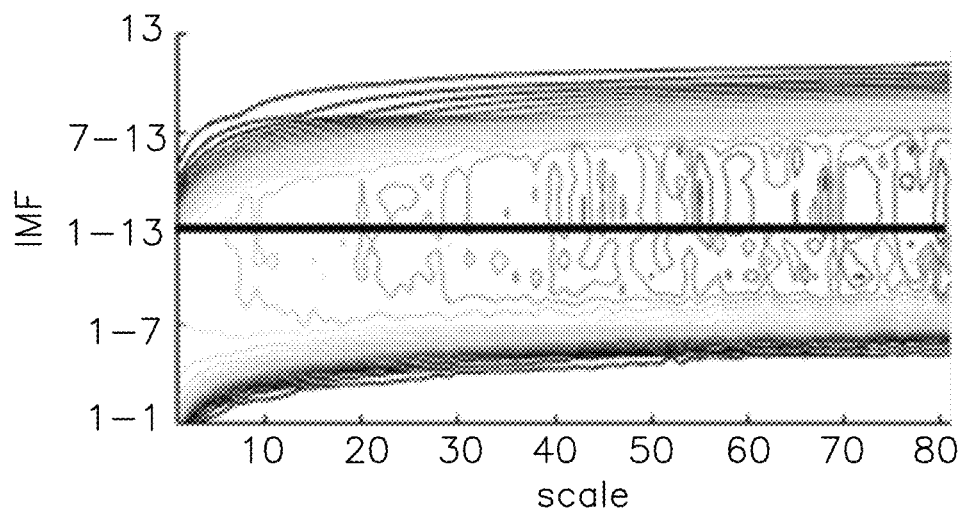
Figure 12G:
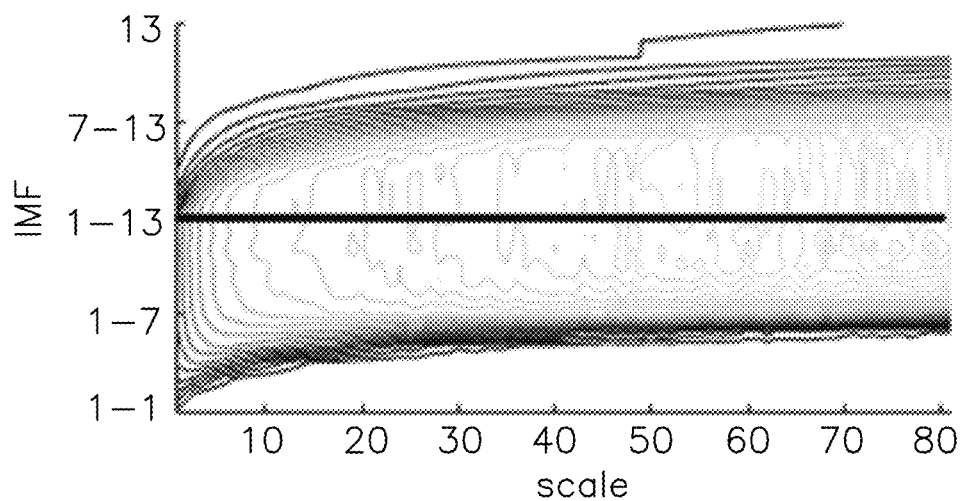
Figure 12H:
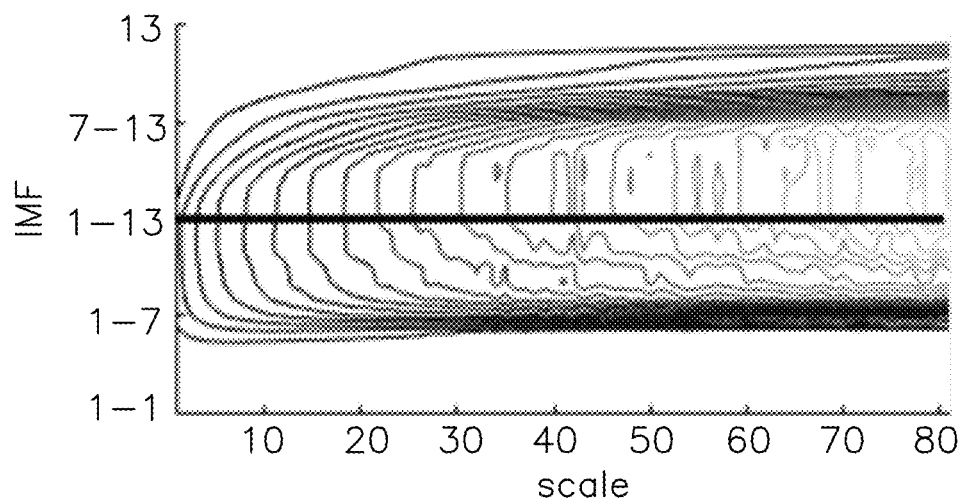
Figure 12I:
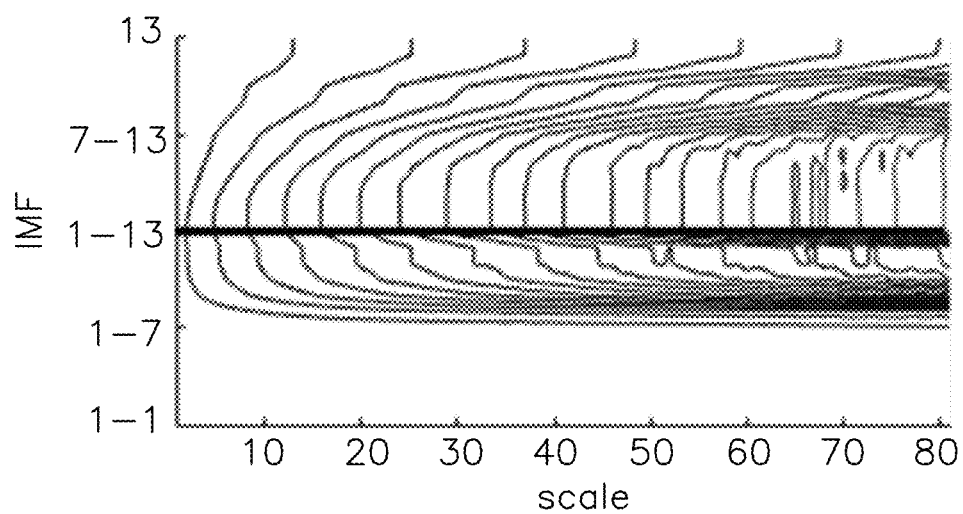

As shown in FIGS. 12A-12C, when 0<H<0.5, negative correlations are presented, representing systems with no long term correlations. As shown in FIGS. 12D-12F, when $0.5<H<1$, long range correlations are presented. Although the original formula of iMSE is valid only for $0<H<1$, it may extend the computation beyond the limit. In the example, the iMSE representations for the data with various H values cover the range of $0<H<1.7$. Note that in these figures, the solid black line divides the domain in two parts: The bottom part gives the ascending sequence of the partial sum from 1 to n, and the top part is for the descending sequence. In the series of figures, it is clearly shown that the energy concentration is migrating to longer scale as the H index values increase as expected: With the increasing value of H, the longer scale becomes increasingly dominant. Thus, we established the principle that iMSE can indeed quantify complexity.

In the present disclosure, iPDF and iMSE may be helpful for diagnosis among various neurophysiological and neuropsychiatric disorders. The visual outputs of the iPDF and iMSE can be used to compare 2 or more states of different groups of people, different individuals, or the same individual. Specific visual output patterns of one or more neurophysiological or neuropsychiatric disorders can be identified. The specific visual output patterns may comprise a disease state, a healthy state, a good prognosis state, or other patterns relevant to diagnosis, prognosis, clinical evaluation, or staging of the disease. The comparison between the specific visual output patterns may be used to identify the difference between two groups of people with different neurophysiological or neuropsychiatric disorders, two groups of people with different disease stage, two groups of people with different prognosis of disease, two individuals with different neurophysiological or neuropsychiatric disorders, two individuals with different disease stage, two individuals with different prognosis of disease, or two different time intervals of the same individual. The comparison on specific patterns may lead to establish a model for the clinical evaluation, diagnosis, staging, or prognosis of the neurophysiological or neuropsychiatric disorder.

A healthy state could be defined as a subject or a group of subjects without being diagnosed with particular disease(s) of interest. A disease state could be defined as a subject or a group of subject being diagnosed with particular disease(s) of interest. The healthy state and the disease state may be presented on the same subject on different time intervals or be presented on different subjects.

The present disclosure will now be described more specifically with reference to the following exemplary embodiments, which are provided for the purpose of demonstration rather than limitation.

J. Application of iPDF in Alzheimer's Disease

Figure 9A:
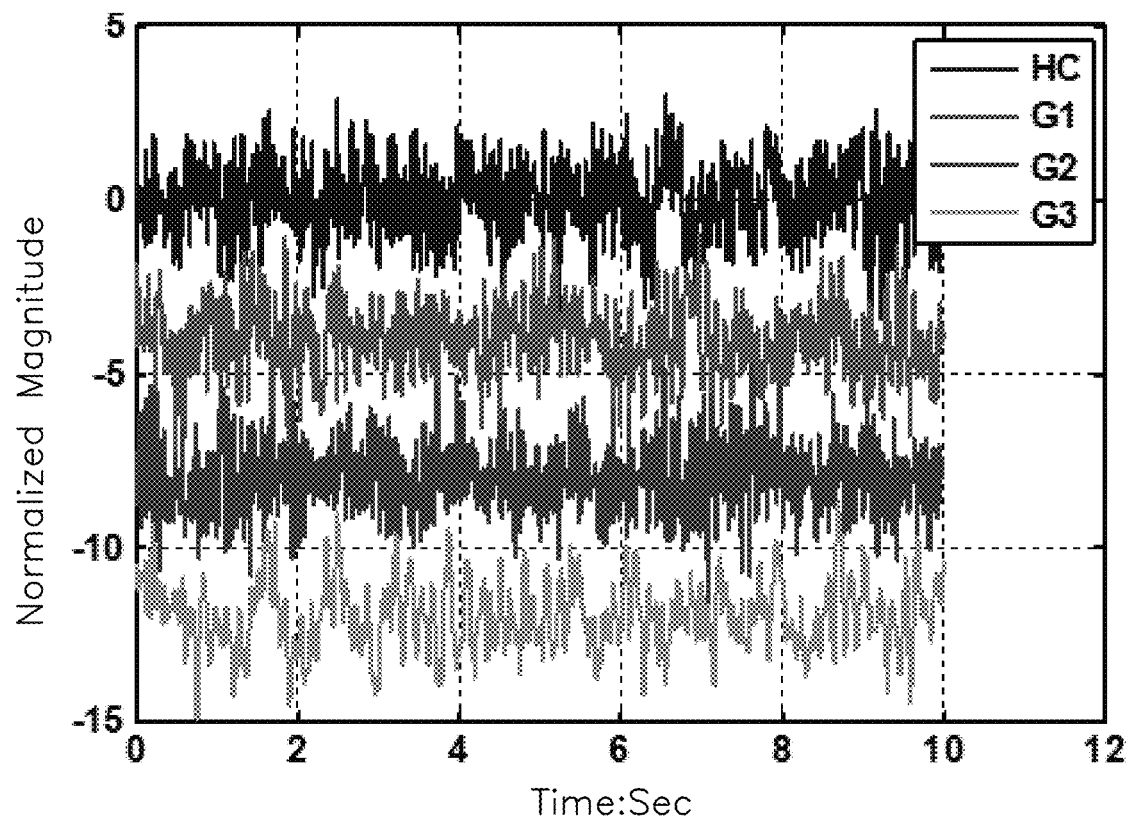
FIG. 9A is a conventional EEG data graph of healthy control subjects and Alzheimer's Disease patients.

In FIG. 9A, a set of conventional EEG data obtained from a healthy control group and Alzheimer's Disease patients at various stages of progress are presented. "HC" indicates EEG data from health control, and "G1", "G2", and "G3" indicate EEG data from Alzheimer Disease patients of various stages. Given the quantity and complexity of EEG data, FIG. 9A provides very little information regarding EEG data distinctions between healthy control group and Alzheimer Disease patients. Even if EEG data in FIG. 9A were further analyzed by Fourier analysis, the non-linear and non-stationary nature of EEG may result in intertwined spectral lines, thus no useful information could be retrieved.

Figure 9B:
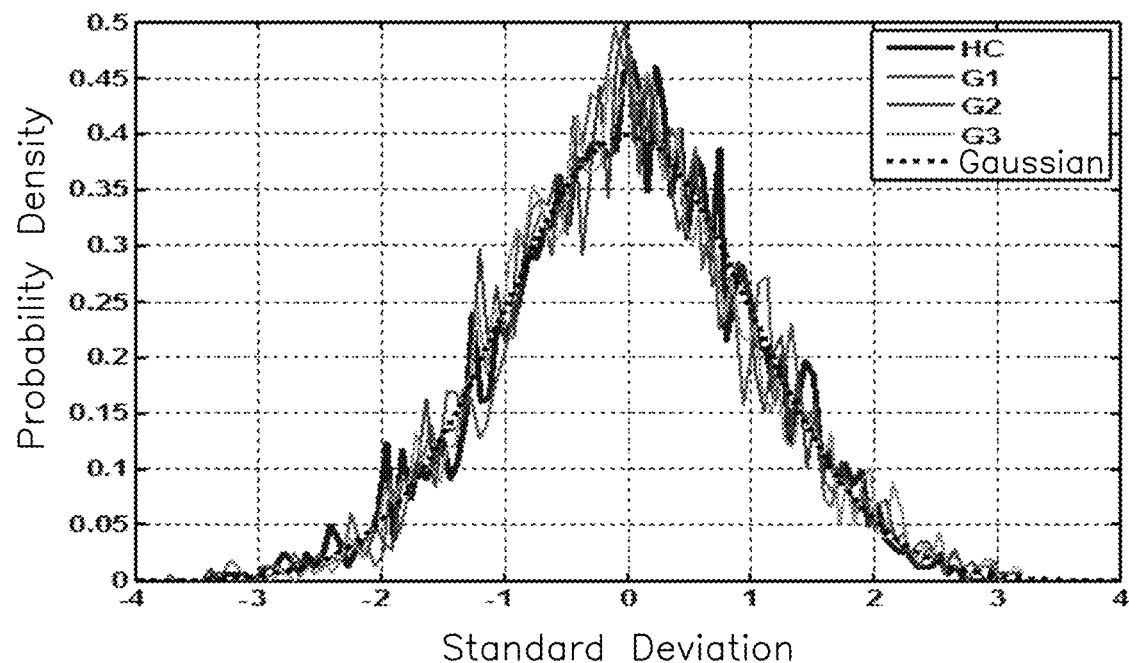
FIG. 9B is a conventional global PDFs from EEG data in FIG. 9A.

In FIG. 9B, the conventional global PDFs of EEG data from healthly control group and Alzheimer's Disease patients at various stages of progress is presented. In conventional global PDF representations, the data from different disease stages or even healthy subjects are all Gaussian. Therefore, FIG. 9B is uninformative, for it could not discriminate one condition from another.

Figure 13A:
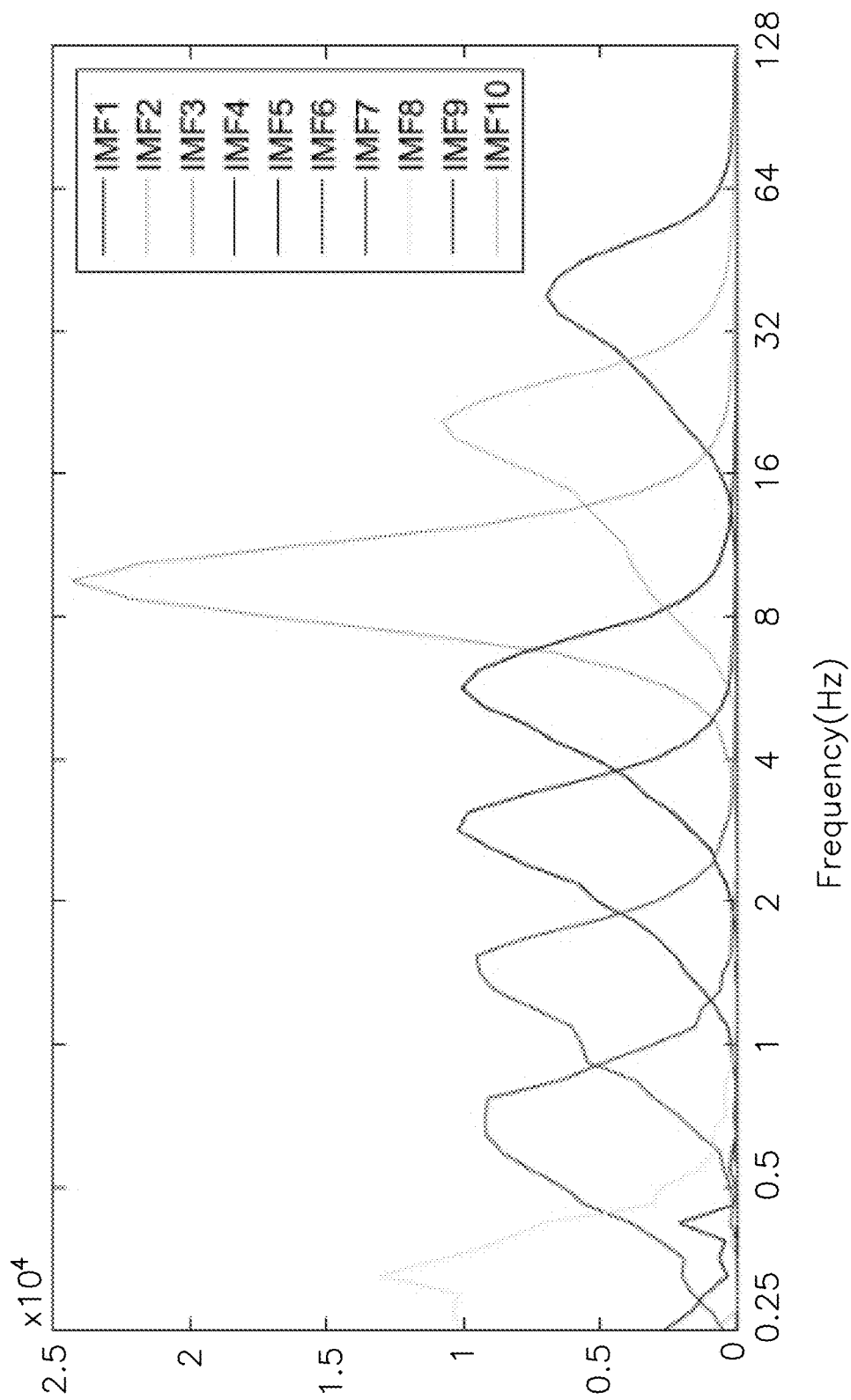
FIGS. 13A and 13B are IMFs at specific instantaneous frequencies of EEG signals.
Figure 13B:
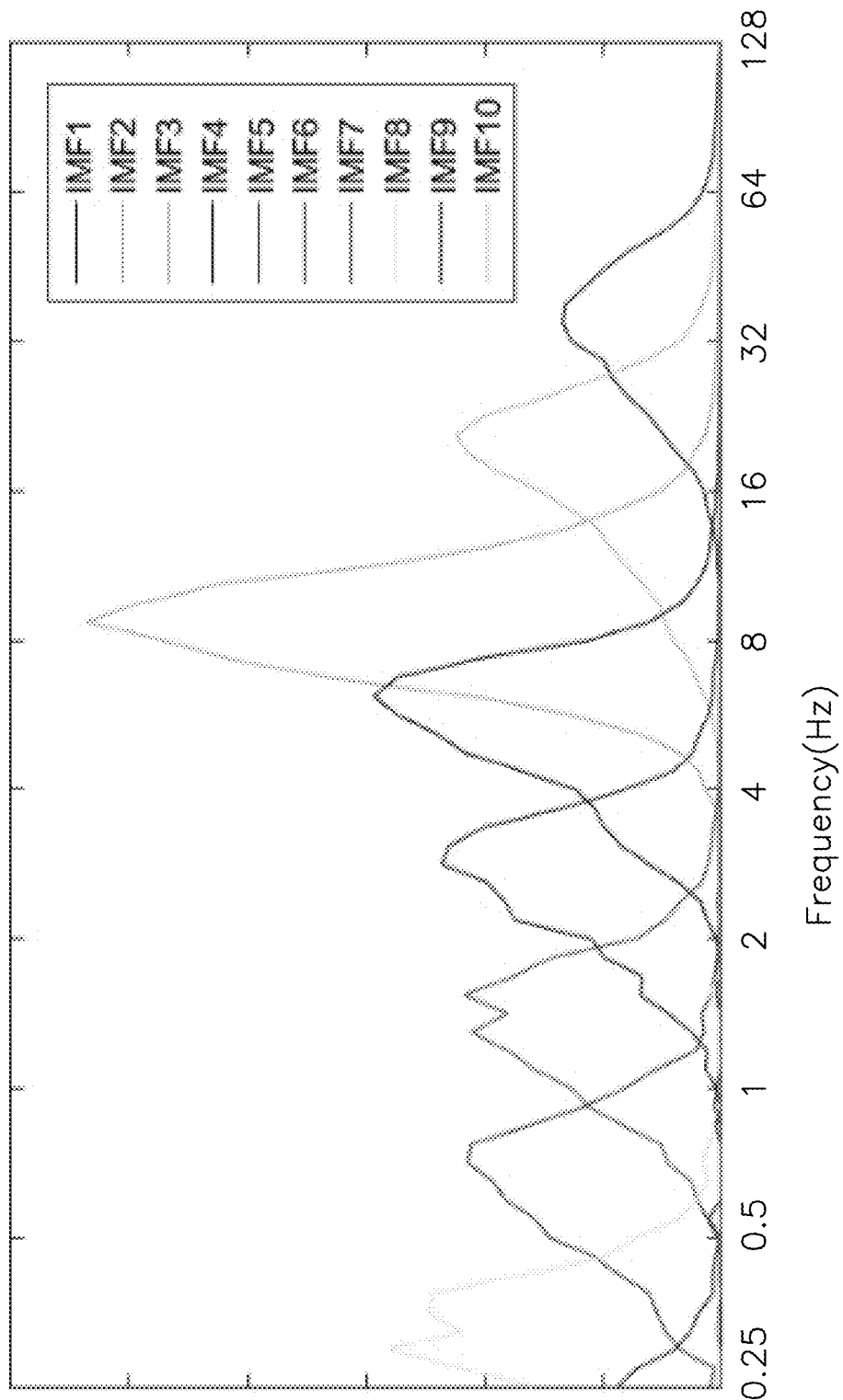

Referring to FIG. 13A, the PDFs of each IMF at a specific instantaneous frequency of EEG signal of a healthy subject are provided, in accordance with an embodiment of the present disclosure. Referring to FIG. 13B, the PDFs of each IMF at a specific instantaneous frequency of EEG signal of a dementia patient (clinical dementia rating 1, CDR1) are provided, in accordance with an embodiment of the present disclosure. In FIGS. 13A and 13B, each curve is an amplitude weighted distribution of instantaneous frequencies for a IMF.

Figure 14A:
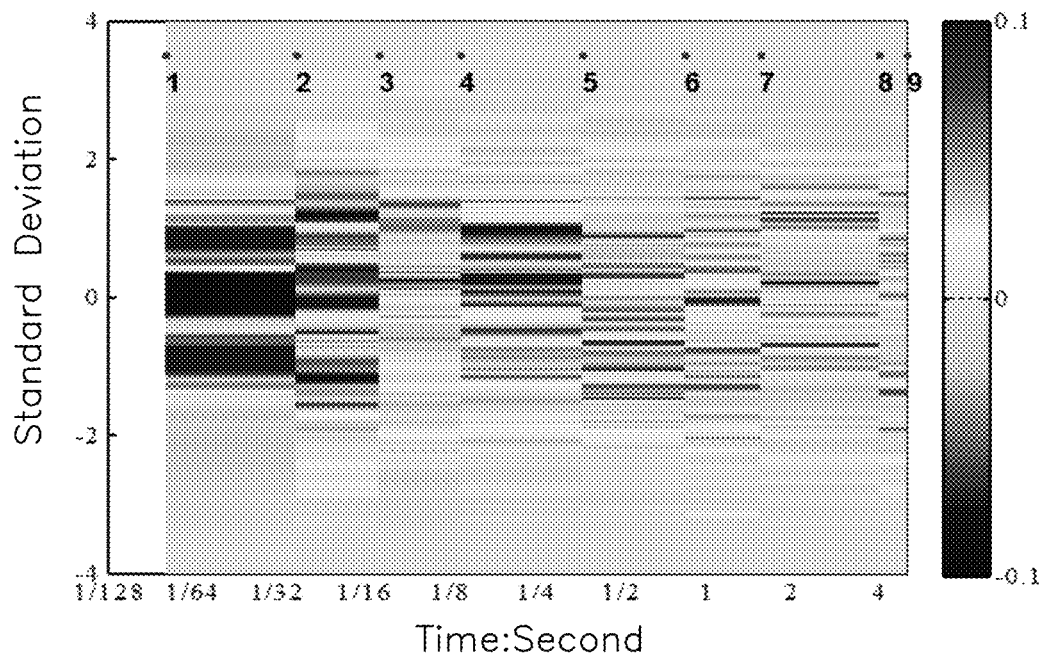
FIGS. 14A-14D are visual outputs of iPDFs of various stages of the Alzheimer's disease, in accordance with an embodiment of the present disclosure.
Figure 14B:
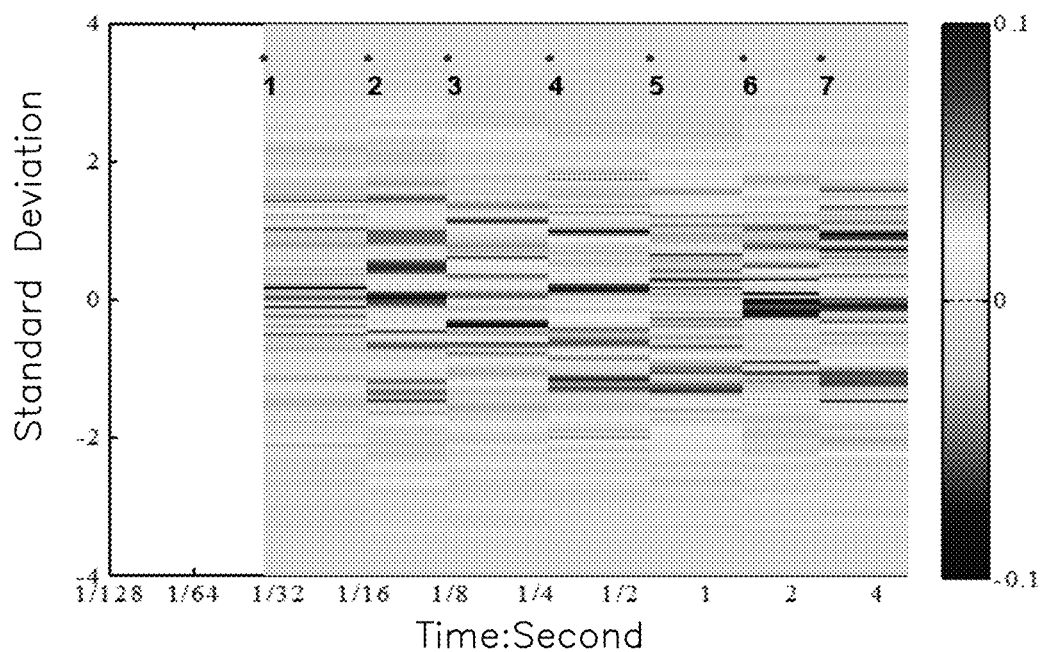
Figure 14C:
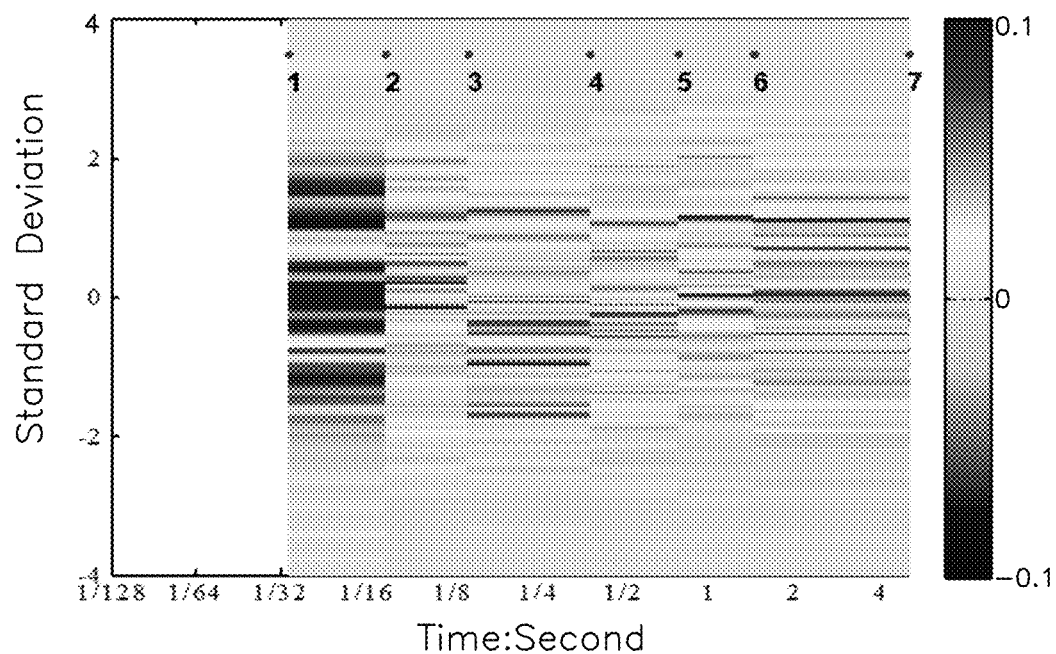
Figure 14D:
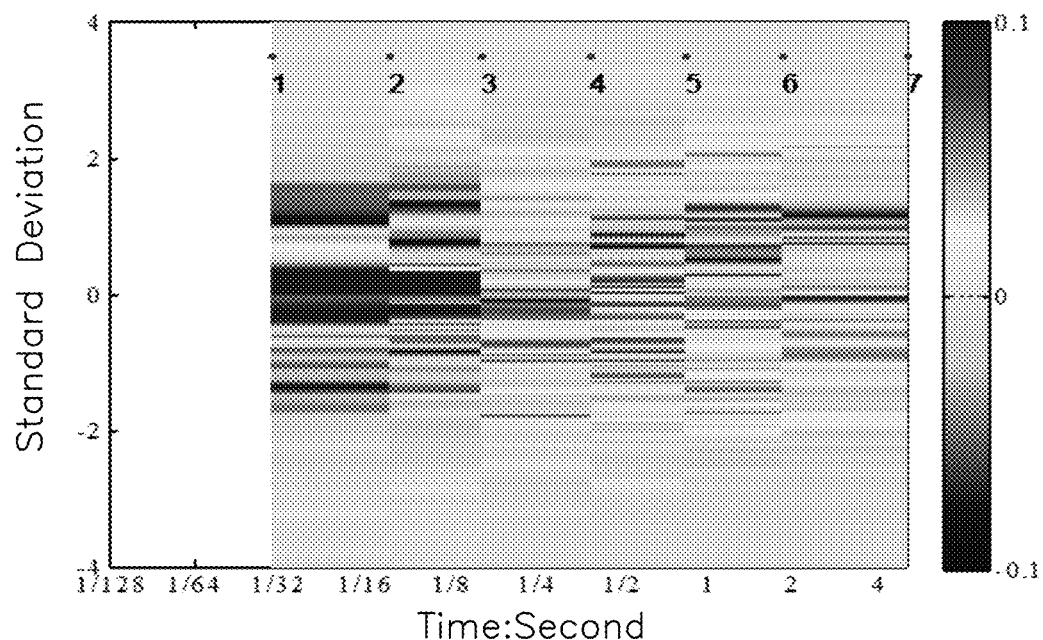

Referring to FIGS. 14A-14D, visual outputs of iPDF of various stages of the Alzheimer's disease is presented with the partial sums, in accordance with an embodiment of the present disclosure. FIG. 14A is the iPDF generated from a healthy subject, FIG. 14B from CDR1 patient, FIG. 14C from CDR2 patient and FIG. 14D from CDR3 patient. When more advanced in staging, the iPDF becomes increasingly super-Gaussian. The super-Gaussian iPDF indicates the lack of variation of the brain responses to any stimuli or the rigid and non-responsive mental state. Of interest is the difference between the iPDF of the healthy subject in FIG. 14A and the initial AD case in FIG. 14B. The highest frequency component for the health control patient is bimodal, indicating that there is a rich signal at the highest frequency range fluctuating with 3-point waves with values either at maxima or minima.

Figure 15A:
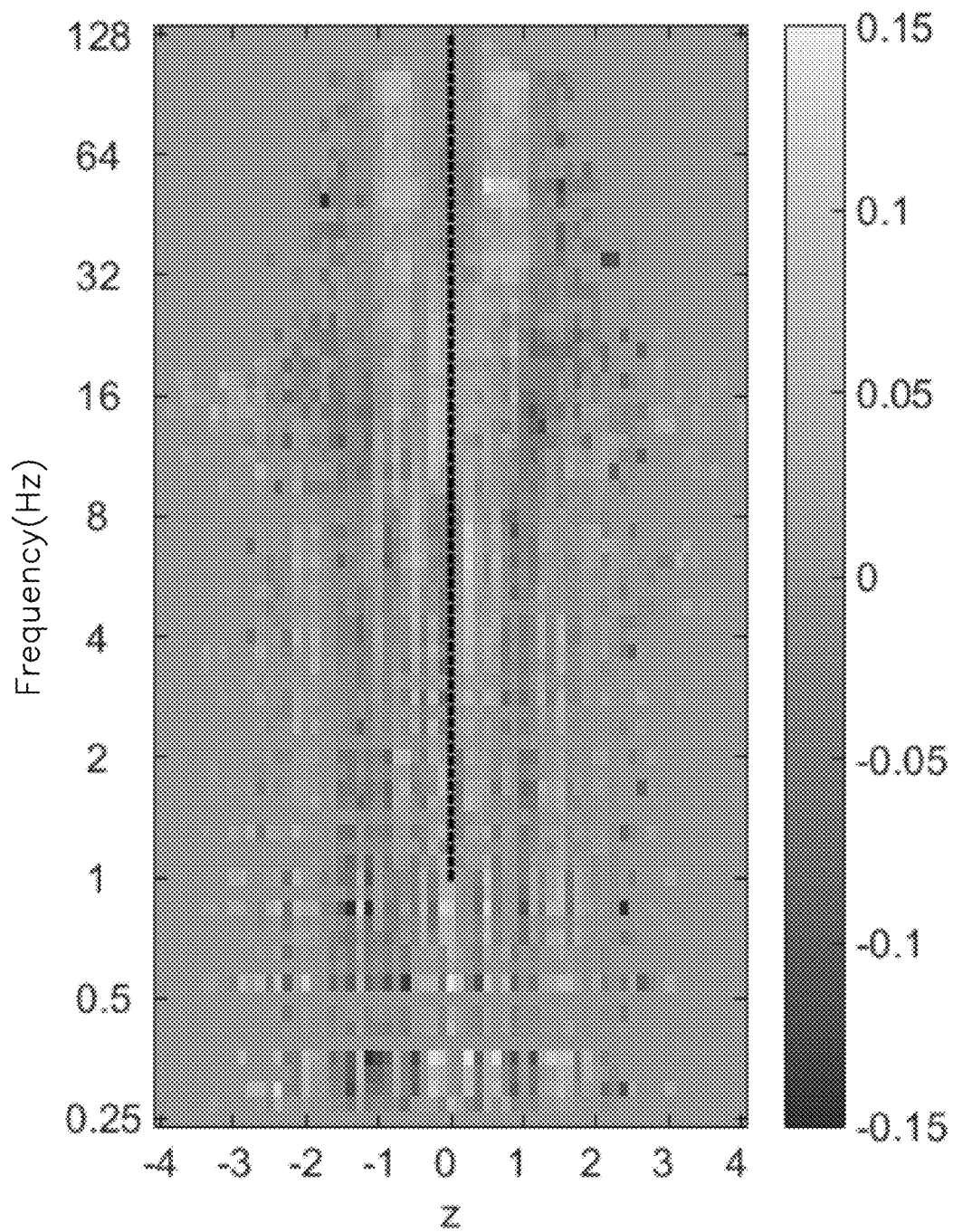
FIGS. 15A-15D are another visual outputs of iPDFs of various stages of the Alzheimer's disease, in accordance with an embodiment of the present disclosure.
Figure 15B:
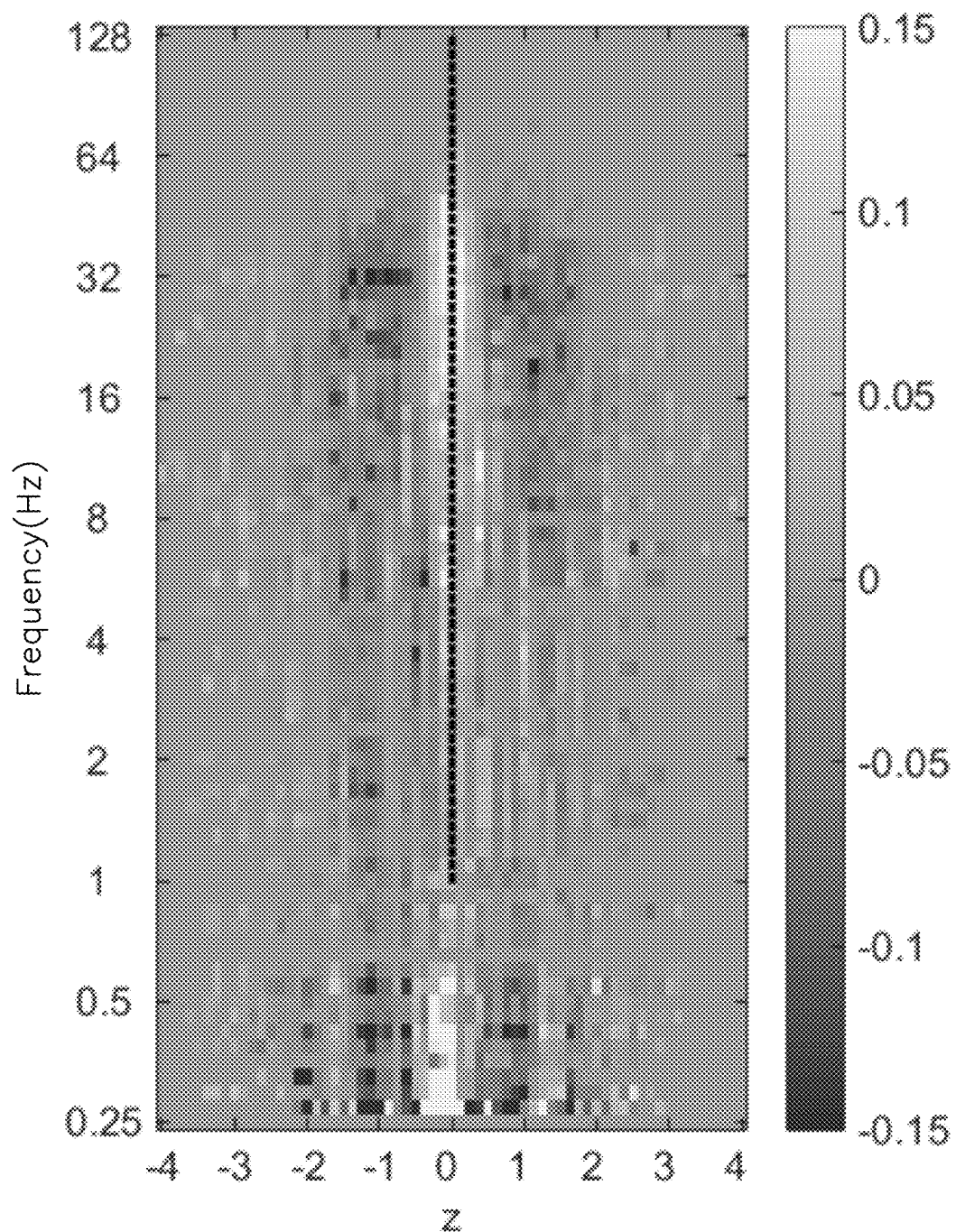
Figure 15C:
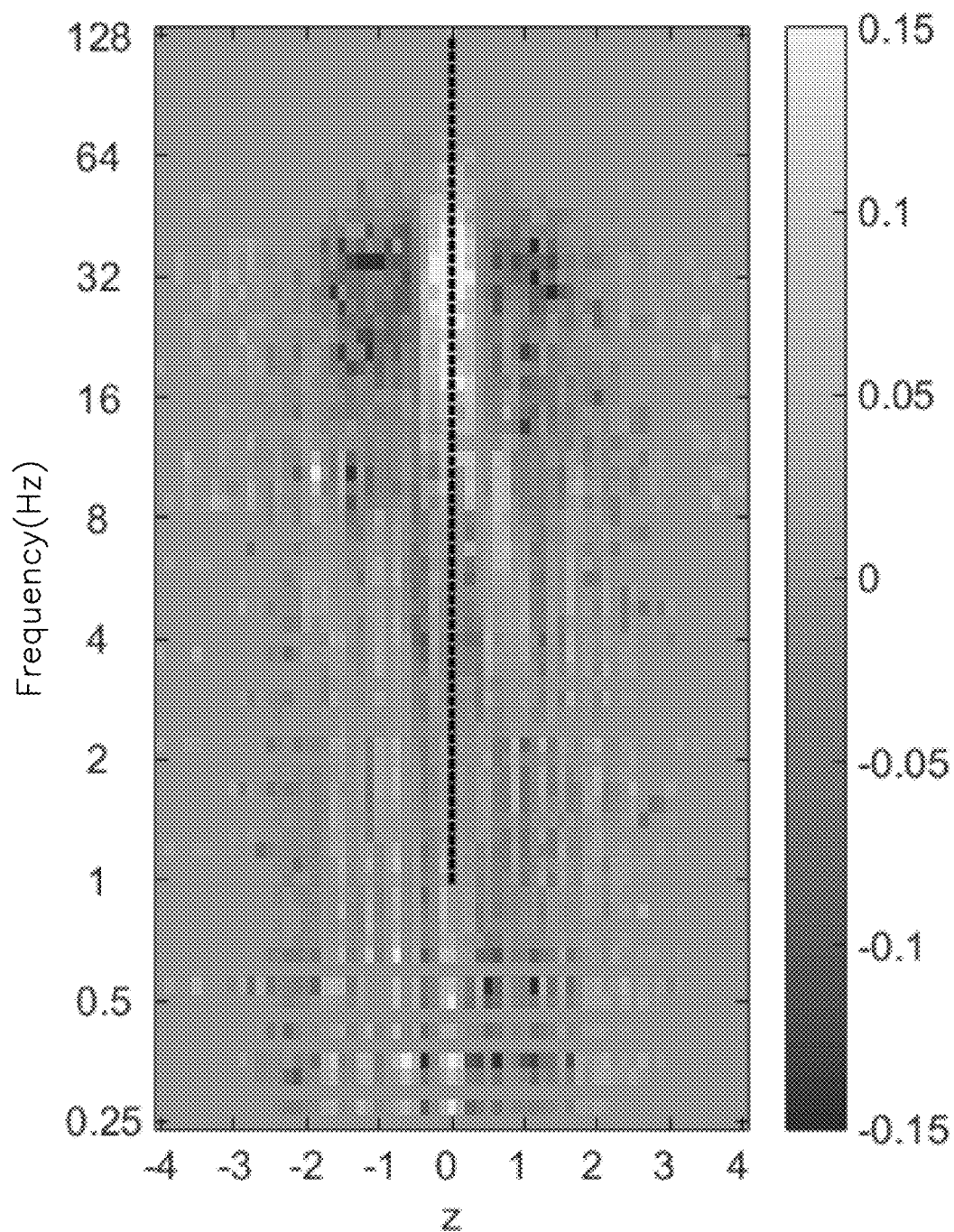
Figure 15D:
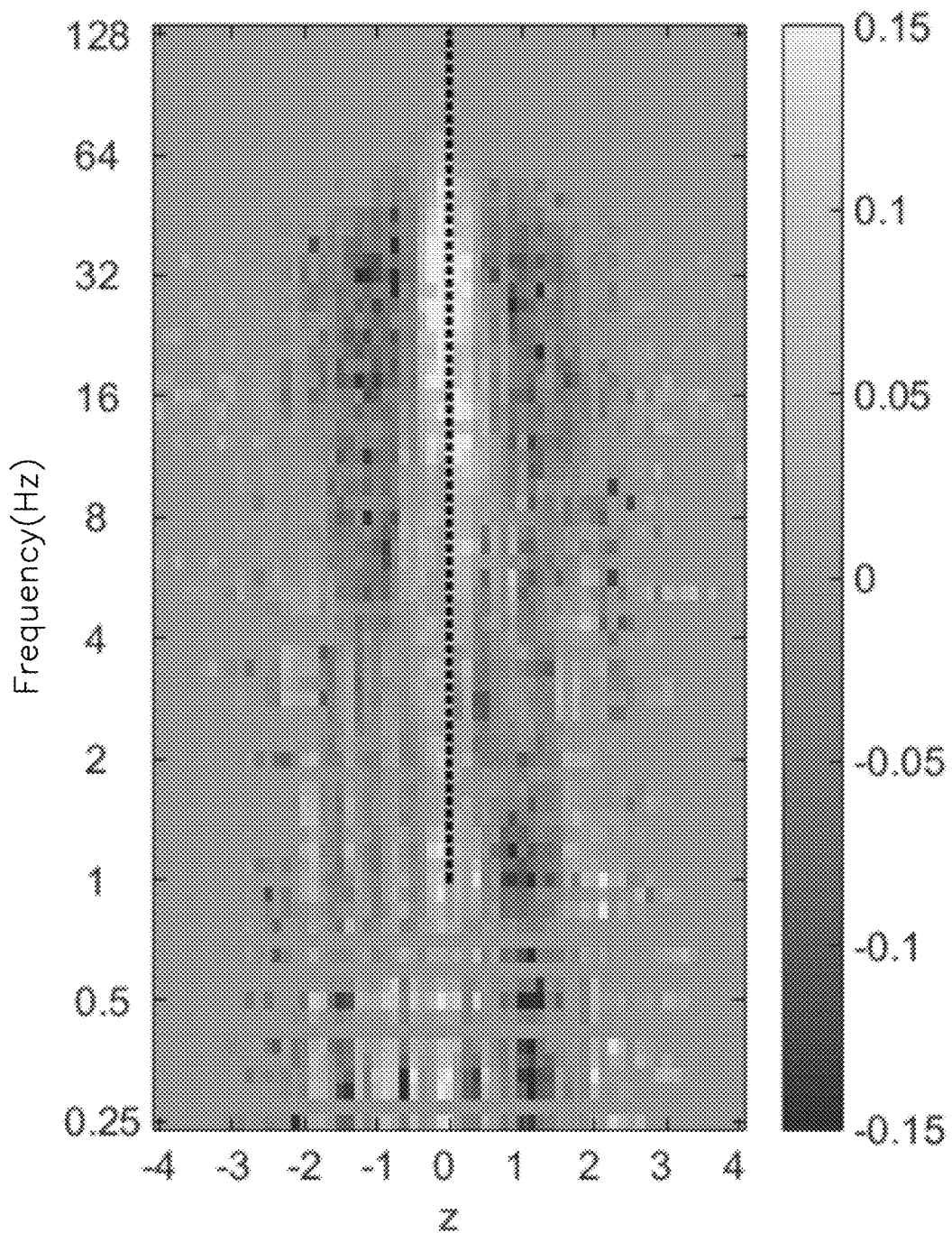

Referring to FIGS. 15A-15D, the iPDFs of various stages of the Alzheimer's Disease progress are presented with continuous time scale, in accordance with an embodiment of the present disclosure. An iPDF is a two-dimensional matrix with the bins defined by the horizontal axis representing the standard deviation of the PDF and the vertical axis representing the time scale (or the instantaneous frequency, for example the inverse of the time scale) of the iPDF. FIG. 15A is the iPDF generated from a healthy subject, FIG. 15B from CDR1 patient, FIG. 15C from CDR2 patient, and FIG. 15D from CDR3 patient. As the disease progresses, the bimodal distribution immediately disappears in the highest frequency component. It is similar to the deterministic wave modulating the white noise in the abovementioned. In the rest of components following the highest frequency component, the distribution again becomes increasingly super-Gaussian. Therefore, the iPDF provide high discriminating power.

In the present disclosure, the iPDF may be presented in a form of contrast between the analyzed data set and a reference data set. For example, the contrast may be generated from two different electrodes. For example, the reference data set may be the health control data set or the data set of the same patient in the past.

Figure 16A:
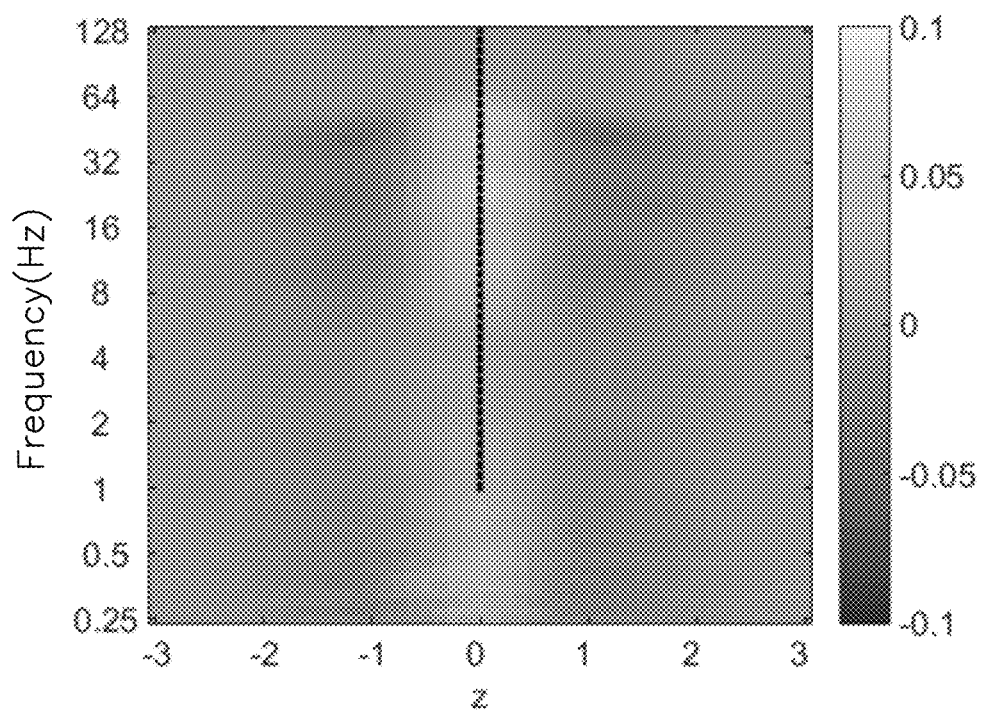
FIGS. 16A-16E are visual outputs of iPDFs of various stages of the Alzheimer's disease with EEG electrode FP1 and T3, in accordance with an embodiment of the present disclosure.
Figure 16B:
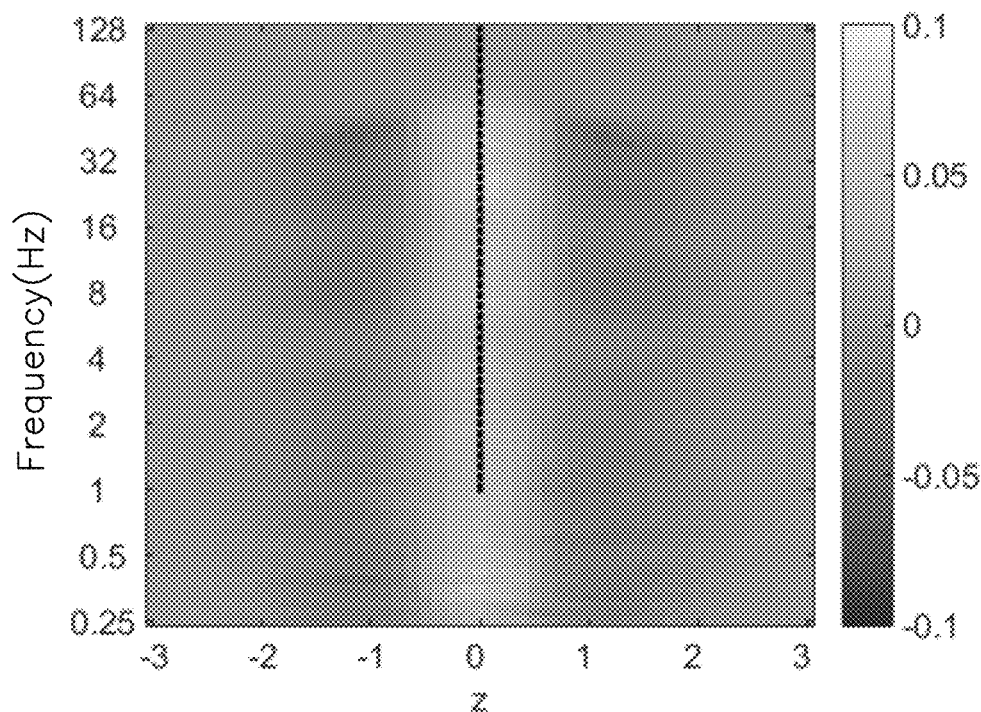
Figure 16C:
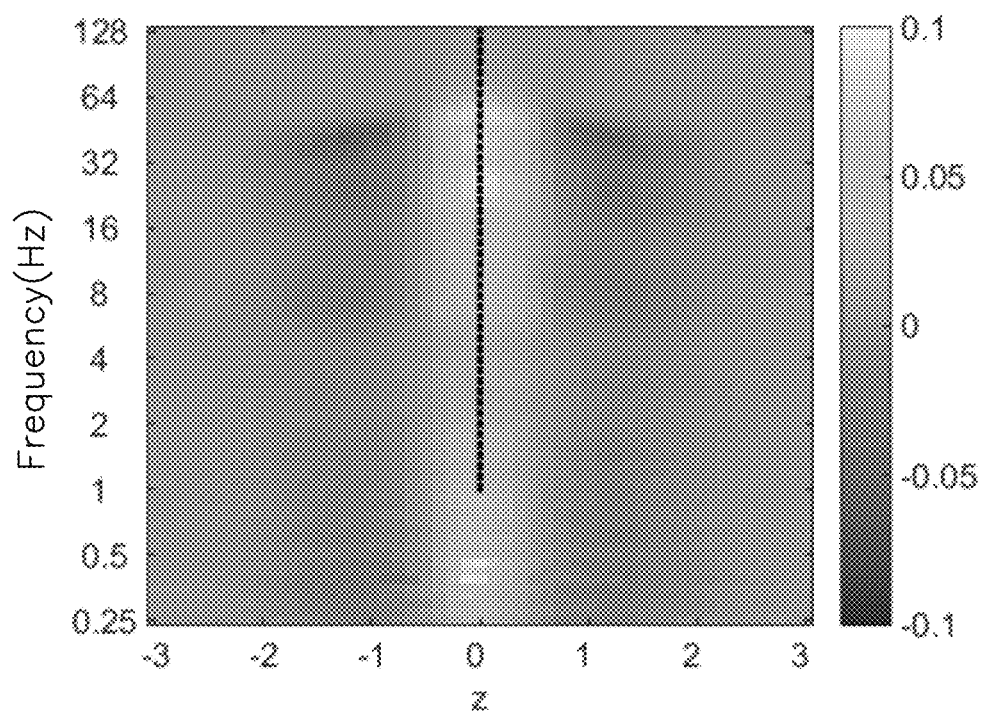
Figure 16D:
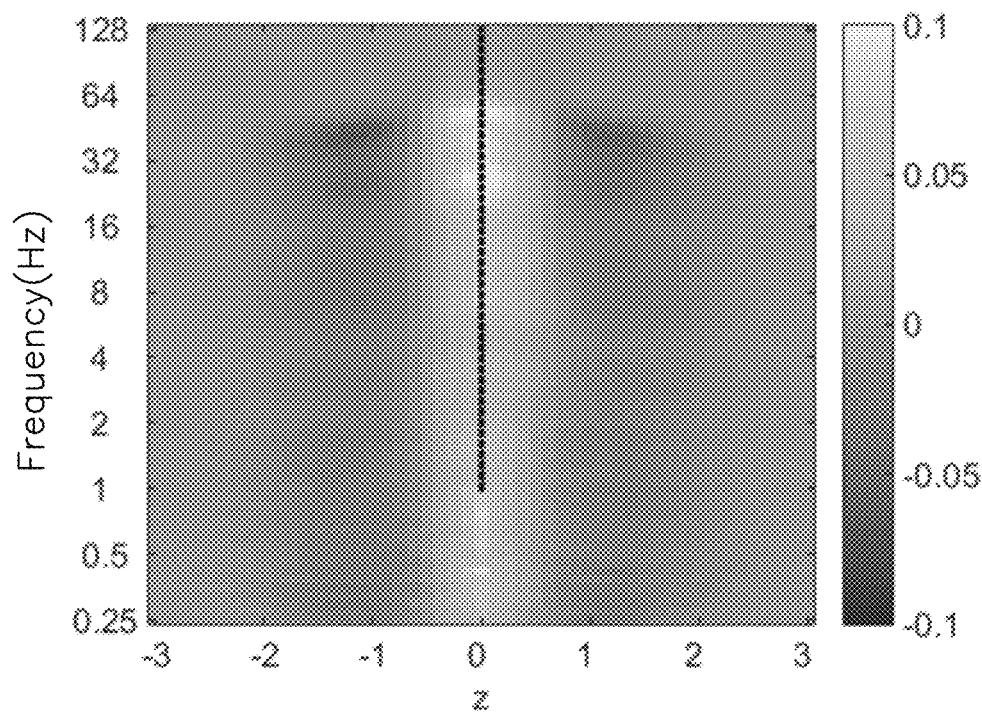
Figure 16E:
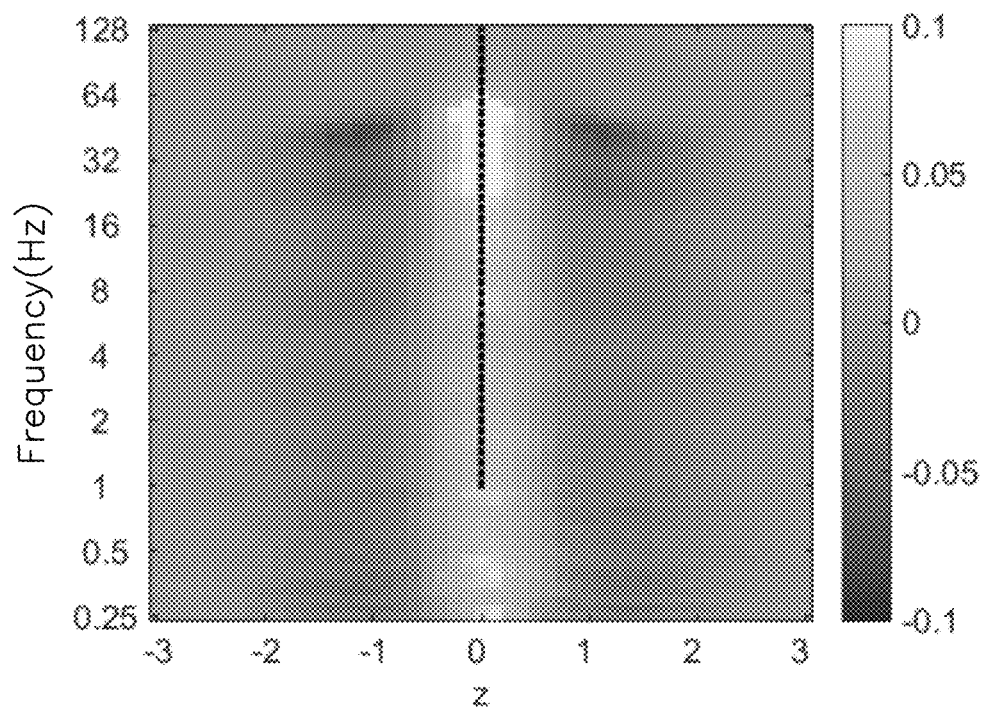

Referring to FIGS. 16A-16E, visual outputs of iPDFs of various stages of the disease progress are presented with EEG electrode FP1 and T3, in accordance with an embodiment of the present disclosure. The iPDFs are generated from EEG electrodes FP1 and T3 on left frontal brain region. FIG. 16A is the iPDF generated from a healthy subject, FIG. 16B from MCI patient, FIG. 16C from CDR1 patient, FIG. 16D from CDR2 patient, and FIG. 16E from CDR3 patient. The probability density value is presented by grayscale.

Figure 17A:
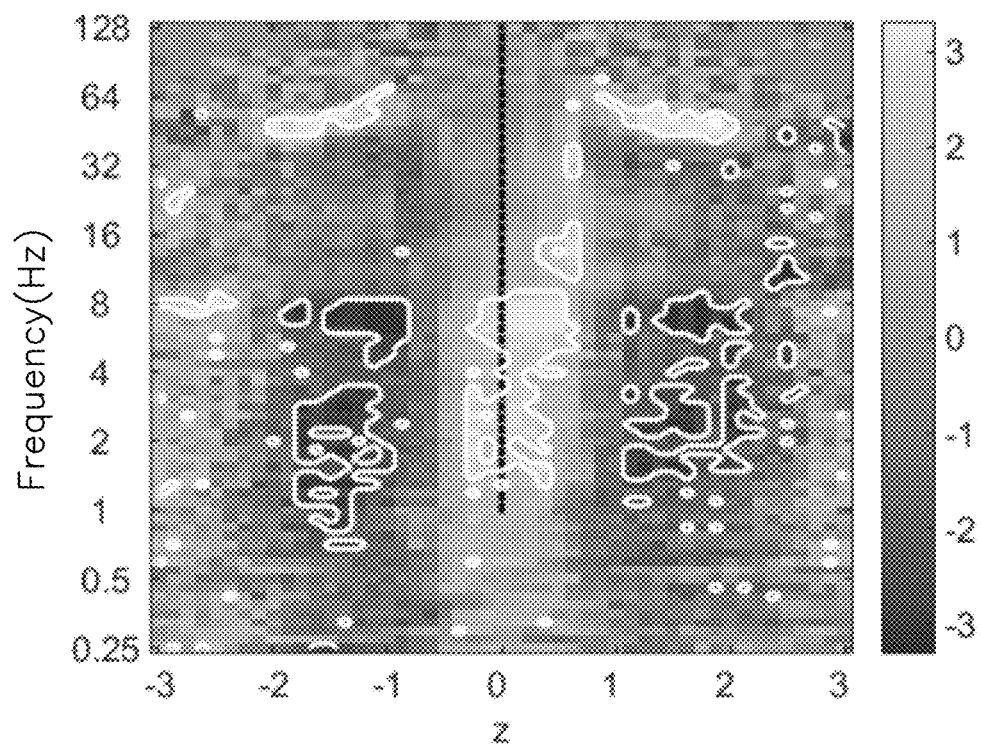
FIGS. 17A-17D are visual outputs of iPDFs representing contrasts between patients and healthy subjects, in accordance with an embodiment of the present disclosure.
Figure 17B:
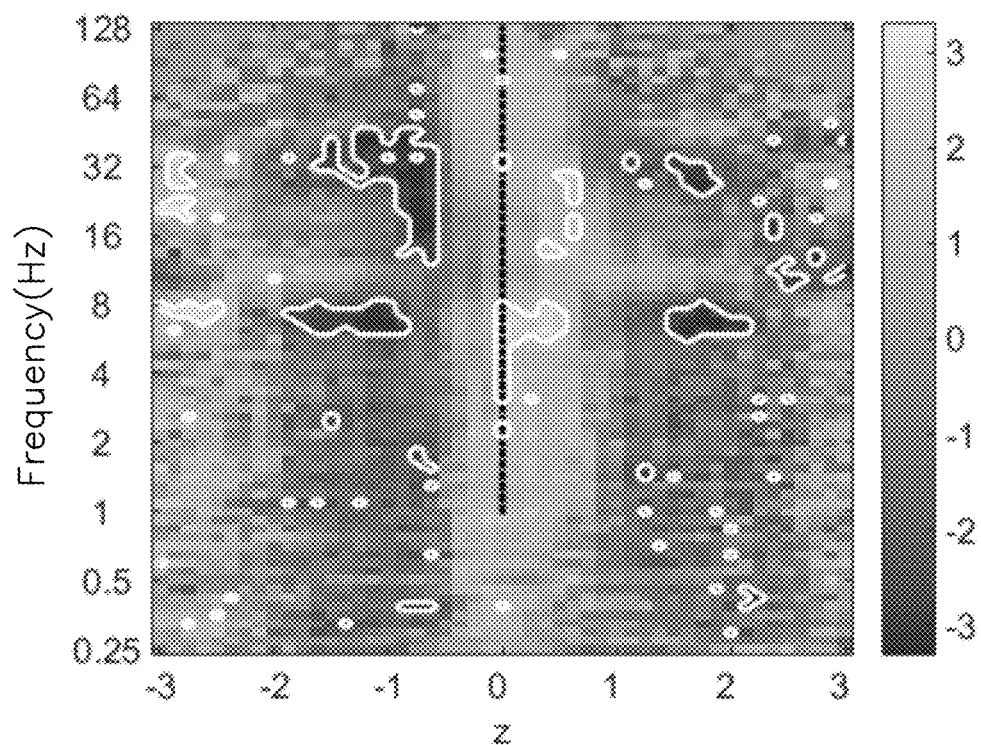
Figure 17C:
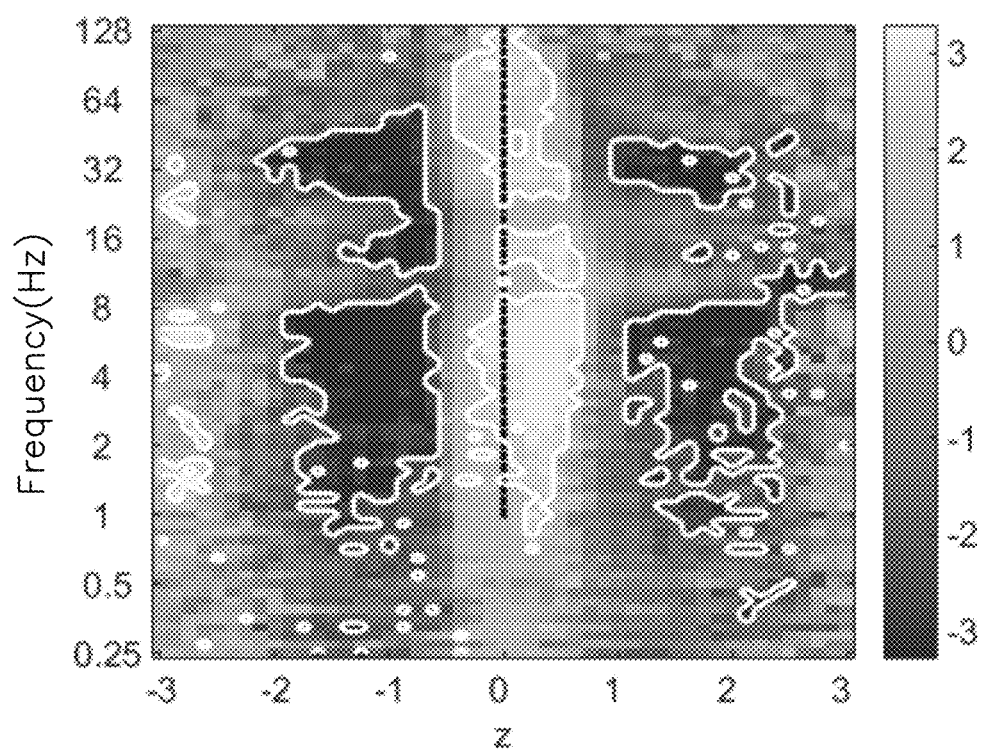
Figure 17D:
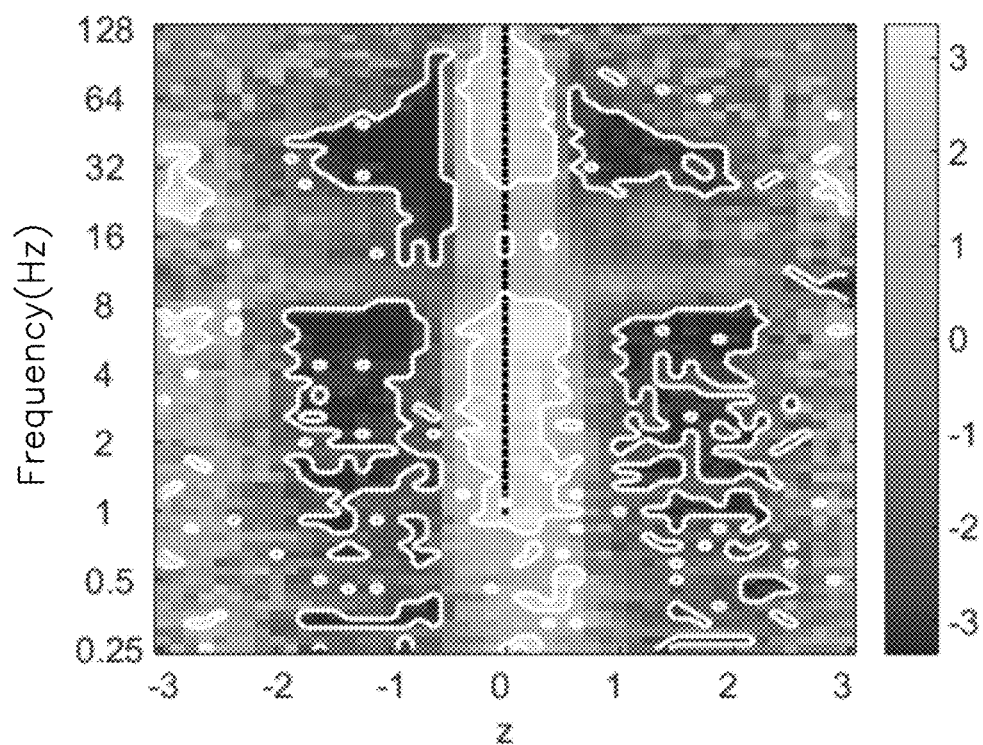

Referring to FIGS. 17A-17D, visual outputs of the iPDFs of various stages of the disease progress are presented with the contrast between a patient and a healthy subject, in accordance with an embodiment of the present disclosure. The iPDFs in FIGS. 17A-17D are generated from EEG electrode FP1 and T3. FIG. 17A is the iPDF generated from a comparison between a MCI patient and a healthy subject, FIG. 17B is the iPDF from a comparison between a CDR1 patient and the healthy subject, FIG. 17C is the iPDF from a comparison between a CDR2 patient and the healthy subject, and FIG. 17D is the iPDF from a comparison between a CDR3 patient and the healthy subject. The iPDFs are presented with the white contours marking regions with statistical significance (in the example, p value less than 0.01). The differences shown in FIGS. 17A-17D clearly indicates contrasts between the disease state patients and the healthy subject.

1.1 Application of iPDF Topography in Alzheimer's Disease

Figure 18:
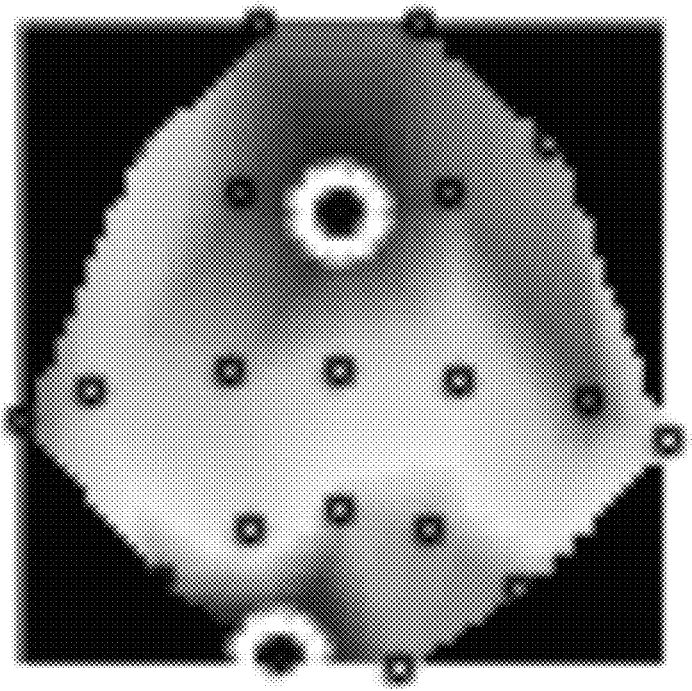
FIG. 18 is a visual output of a functional iPDF (fiPDF) topography in accordance with an embodiment of the present disclosure.

In FIG. 18, a functional iPDF topography is presented in accordance with an embodiment of the present disclosure. The iPDF topography is generated from the iPDFs acquired from the multiple EEG electrodes representing different locations on the scalp. A boundary of the topography defines an anatomical graph of the brain in FIG. 18. Each of the EEG electrodes is a detection unit in the boundary. The electrode is indicated with a circle, and the probability density value of each of the corresponding electrodes is also marked. The probability density value is represented by grayscale. In one example, the method of generation of iPDF topography comprises the following steps. Generating the data set of the iPDFs from each electrode; converting the instantaneous time scale to instantaneous frequency scale (by the inverse of the time scale); establishing a two dimensional bin matrix and each bin comprising a first bin value defined for desired standard deviation values and a second bin value determined by the instantaneous frequency scale (as inverse of the instantaneous time scale). In some example, the iPDF topography may be further contoured according to the probability density values in each bin based on the respective probability density value from each electrode. In some examples, modeled probability density values are generated for intermediate areas between the electrode in the iPDF topography. The modeling process may be an interpolation between one probability density value of one electrode and another probability density value of another electrode. The modeled probability density value can be a transitional probability density value between two adjacent electrodes.

The advantage of the frequency scale is that an oscillation within the frequency scale may be indicative to the brain functions. The collective of all the bins would be the iPDF topography. Furthermore, to accentuate the disorders, the iPDF topography may be presented with the contrast between two iPDF topography. For example, the two iPDF topographs may be the patient group and the control reference group. In this presentation, the bin value may be the probability density value, the contrast between the probability density values or the statistical significance values. The statistical significance value may be generated according to the standard T-test to show the statistics between different patient groups. Also, the bin value may be rendered to a color code.

The iPDF links specific range of brain wave frequency with the distribution of the signal over the scalp; thus, the iPDF topography can be a tool for evaluating, diagnosing, or staging neurophysiological and neuropsychiatric disorders.

In one example of the iPDF topography, the detection module is a 10-20 system comprising twenty-one detection unit. Within a small range of amplitude modulation frequency and frequency modulation frequency, each one of the detection units on the corresponding location of the anatomical graph has a signal strength value. The modeling process determines the signal strength values for the visual elements of the intermediate areas between the detection units. The modeling process may be achieved by interpolation.

Figure 19A:
FIGS. 19A-19D are visual outputs of fiPDFs of various stages of Alzheimer's disease, in accordance with an embodiment of the present disclosure.
Figure 19B:
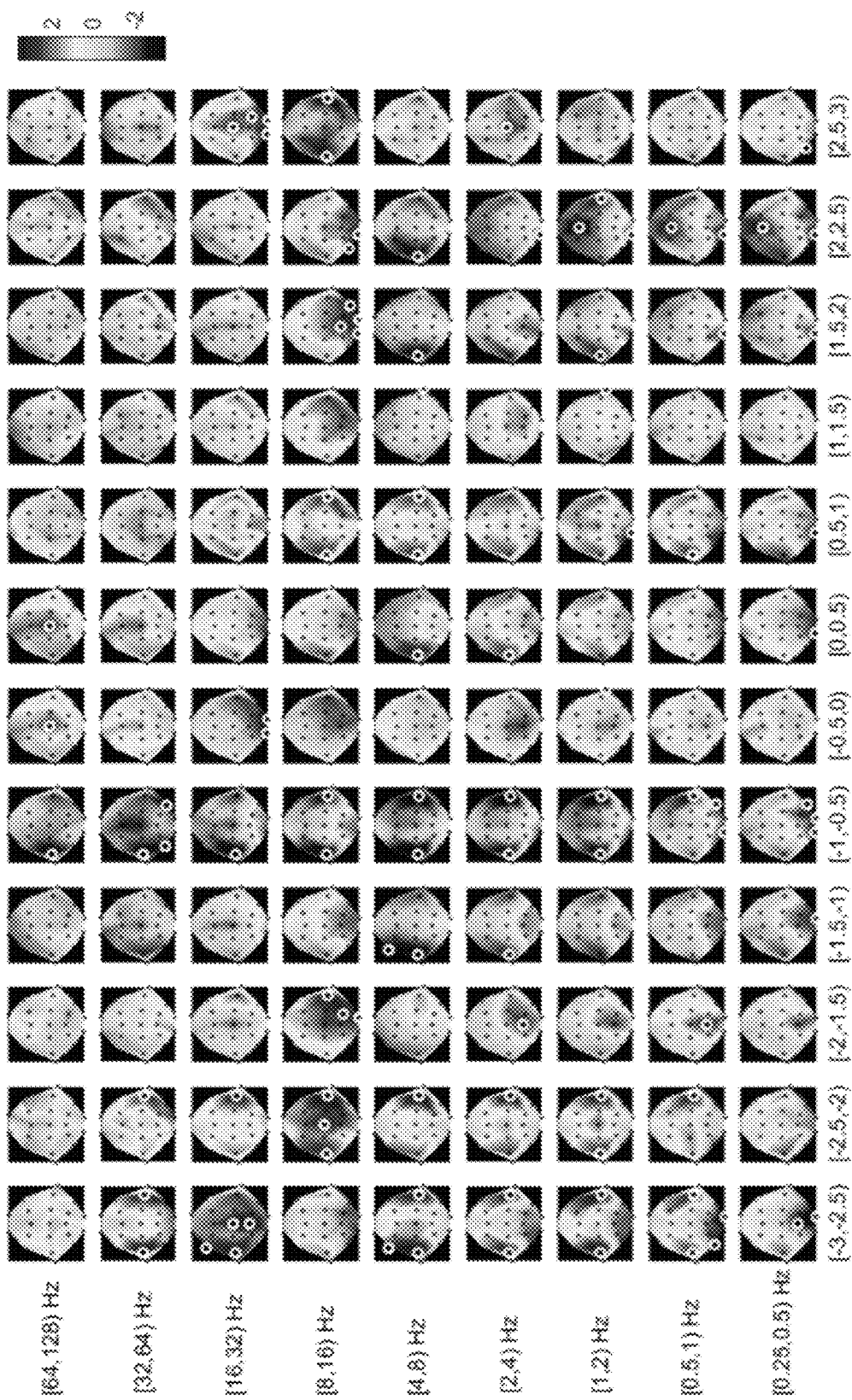
Figure 19C:
Figure 19D:

Referring to FIGS. 19A-19D, fiPDFs (functional iPDFs) on various stages of Alzheimer's disease are presented with the contrast between a group of patients and a group of healthy subjects, in accordance with an embodiment of the present disclosure. The fiPDFs comprises a matrix of iPDF topographies. Each iPDF topography is generated according to a specific range of frequency modulation and amplitude modulation. In FIGS. 19A-19D, the horizontal axis is a time interval and the vertical axis is an instantaneous frequency of the PDFs, wherein the PDFs are generated from the IMFs. Each of the iPDF topographies are defined by a boundary representing an anatomical graph of the brain, and each of the iPDF topographies comprises a plurality of detection unit and intermediate areas between the detection units, wherein each of the detection units has a probability density value. The intermediate area has a modeled probability density value that is modeled from probability density values of the surrounding detection units. FIG. 19A is the fiPDF generated from a group of MCI patients with contrast to the group of healthy subjects, FIG. 19B is the fiPDF generated from a group of CDR1 patients with contrast to the group of healthy subjects, FIG. 19C is the fiPDF generated from a group of CDR2 patients with contrast to the group of healthy subjects, and FIG. 19D is the fiPDF generated from a group of CDR3 patient with contrast to the group of healthy subjects. The fiPDFs are presented with the white contours marking the region with statistically significant (in the example, p value less than 0.01). As the severity of the disease advances, the difference in the fiPDFs becomes increasingly clear between the patient group and the healthy subject group.

Figure 20A:
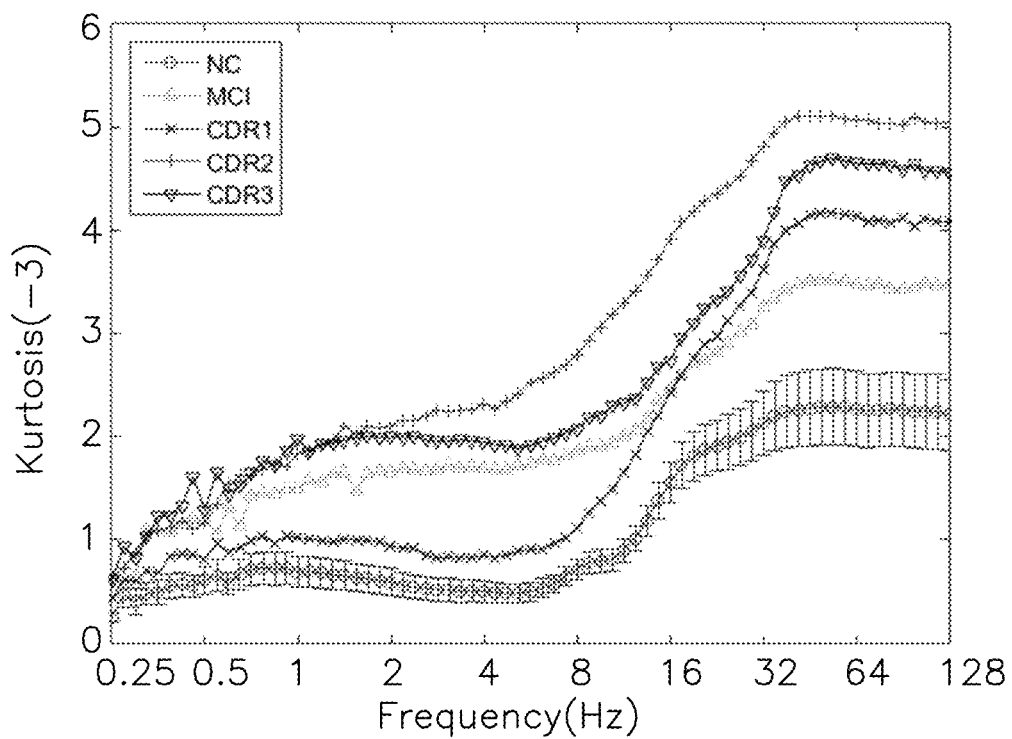
FIG. 20A is a mean kurtosis value graph from patient groups and a healthy subject group, in accordance with an embodiment of the present disclosure.

Referring to FIG. 20A, a plurality of mean kurtosis values from patient groups and a healthy subject group are graphed, in accordance with an embodiment of the present disclosure. In FIG. 20A, the mean kurtosis values from different groups of patients or healthy subjects are shown along with different frequencies. Also, deviations with one sigma scattering are marked in FIG. 20A. In one example, the signals are acquired from two electrodes: FP1 and T3 on left frontal brain region. The different patient groups of various stages of the disease progress are clearly separable especially at the high frequency range of 32 Hz and frequency ranges above 32 Hz.

Figure 20B:
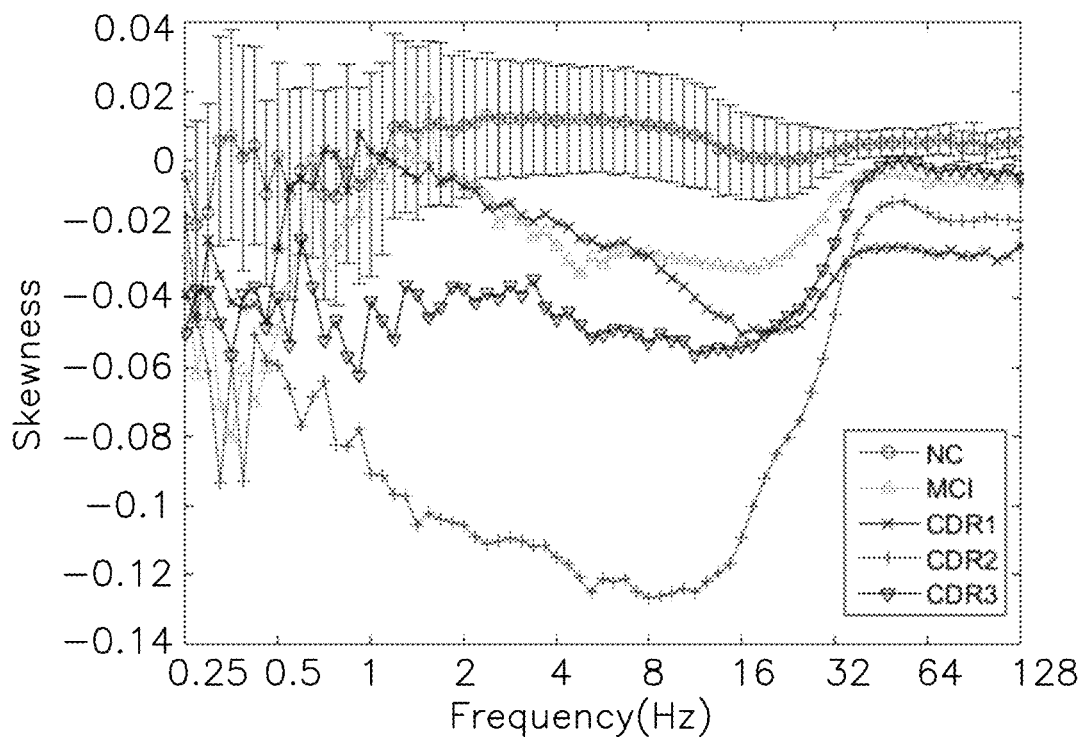
FIG. 20B is a mean skewness value graph from patient groups and a healthy subject group, in accordance with an embodiment of the present disclosure.

Referring to FIG. 20B, a plurality of mean skewness values from patient groups and a healthy subject group are graphed, in accordance with an embodiment of the present disclosure. In FIG. 20B, the mean skewness from different groups of patients or healthy subjects are shown along with different frequencies. Also, deviations with one sigma scattering are marked in FIG. 20B. In one example, the signals are acquired from two electrodes: FP1 and T3 on left frontal brain region. In FIG. 20B, the skewness of the patient groups are clearly distinguished from the skewness of the healthy subject group.

Figure 21A:
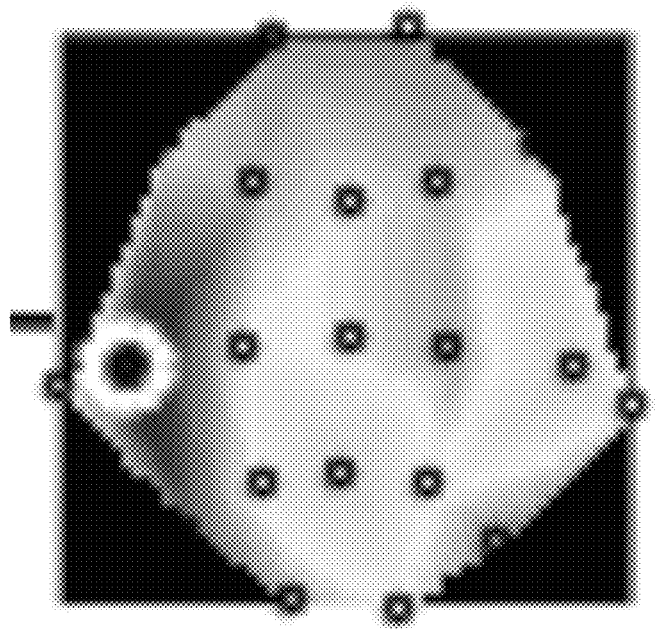
FIG. 21A is a visual output of an iPDF kurtosis topography, in accordance with an embodiment of the present disclosure.
Figure 21B:
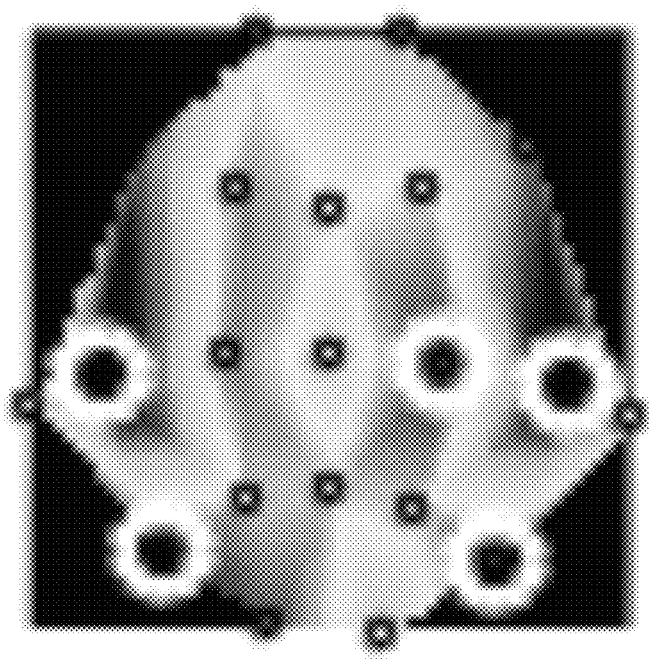
FIG. 21B is a visual output of an iPDF skewness topography, in accordance with an embodiment of the present disclosure.

Referring to FIG. 21A, an iPDF kurtosis topography is presented in accordance with an embodiment of the present disclosure. The iPDF kurtosis topography is generated from the kurtosis values of the iPDFs acquired from the multiple electrodes. Referring to FIG. 21B, an iPDF skewness topography is presented in accordance with an embodiment of the present disclosure. The iPDF skewness topography is generated from the skewness values of iPDFs acquired from multiple electrodes. Within each bin, the probability density value of the corresponding electrode is also marked and represented by the grayscale. In one example, the method of generation of iPDF topography comprises the following steps: generating the data set of the iPDFs from each electrode; converting the instantaneous time scale to instantaneous frequency scale (by the inverse of the time scale); establishing a two dimensional bin matrix and each bin comprising a first bin value defined for desired standard deviation values and a second bin value determined by the instantaneous frequency scale (as inverse of the instantaneous time scale). In some example, the iPDF topography may be further contoured according to the probability density values in each bin based on the respective probability density value from each electrode. Furthermore, the probability density value may be generated from a subject with reference to the reference dataset. The visual elements may be the contrast between an analyzed data set and the reference data set. The contrast may be processed by a normalization process to align with a linear scale or a distribution model, such as normal distribution. The reference data units in the reference data set may be directed from a standard data set or a longitudinal data set. The standard data set is generated from the average of the analyzed data sets from a specific group of subjects. For example, the specific group of subjects may be healthy subjects or people diagnosed with certain disease status. To eliminate individual variations, a normalization of the individual data can be used. The longitudinal data set may be generated from a series of previously analyzed data sets of the same subject. In some examples, z-score can be calculated according to the reference data set. Based on locations of the electrodes on the sculp, a device may further generate a graph to demonstrate that the location of the analyzed data set in a distribution model.

Figure 22A:
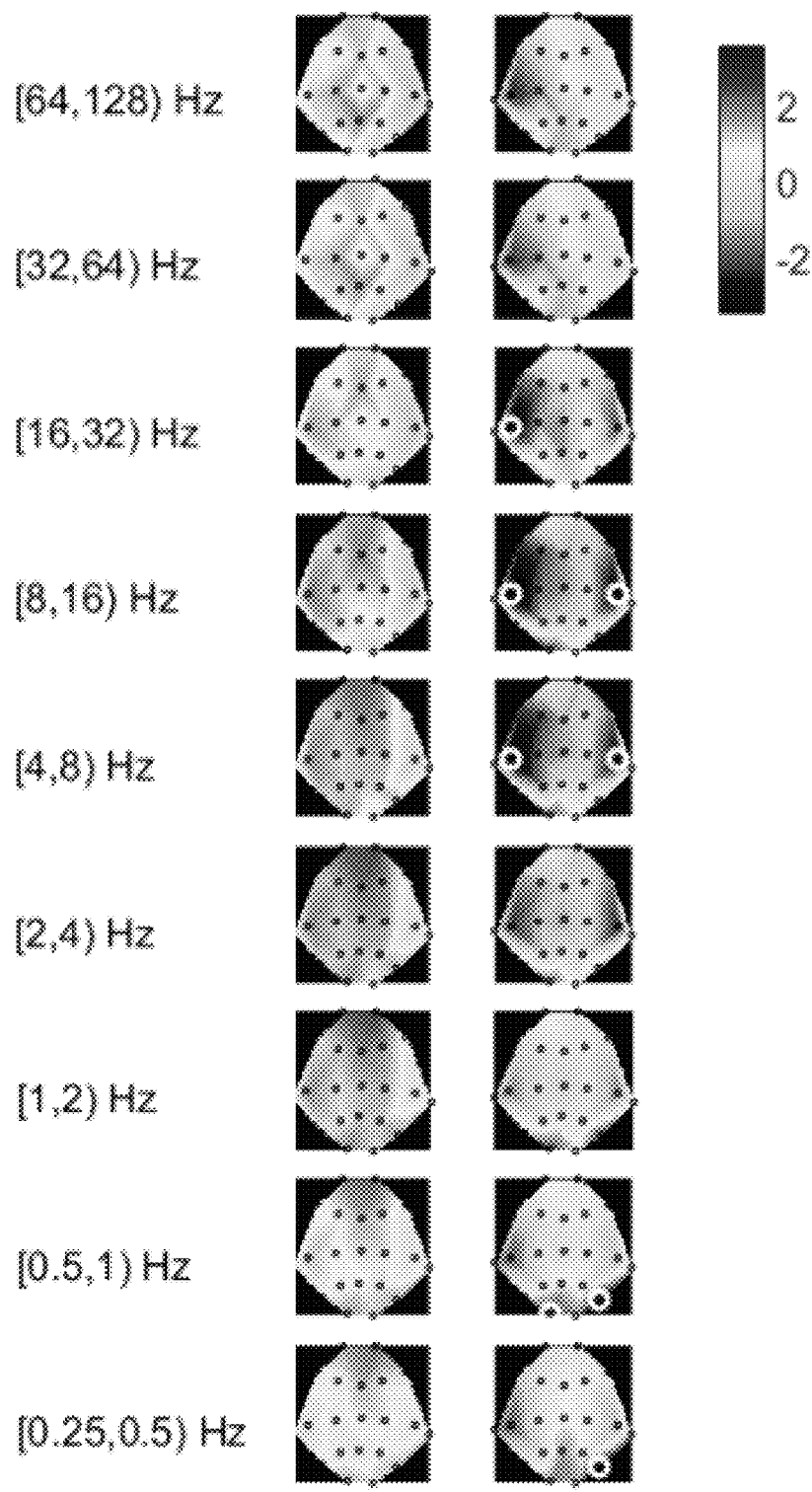
FIGS. 22A-22D are visual outputs of a plurality of comparisons between iPDF kurtosis topographies and iPDF skewness topographies, in accordance with an embodiment of the present disclosure.
Figure 22B:
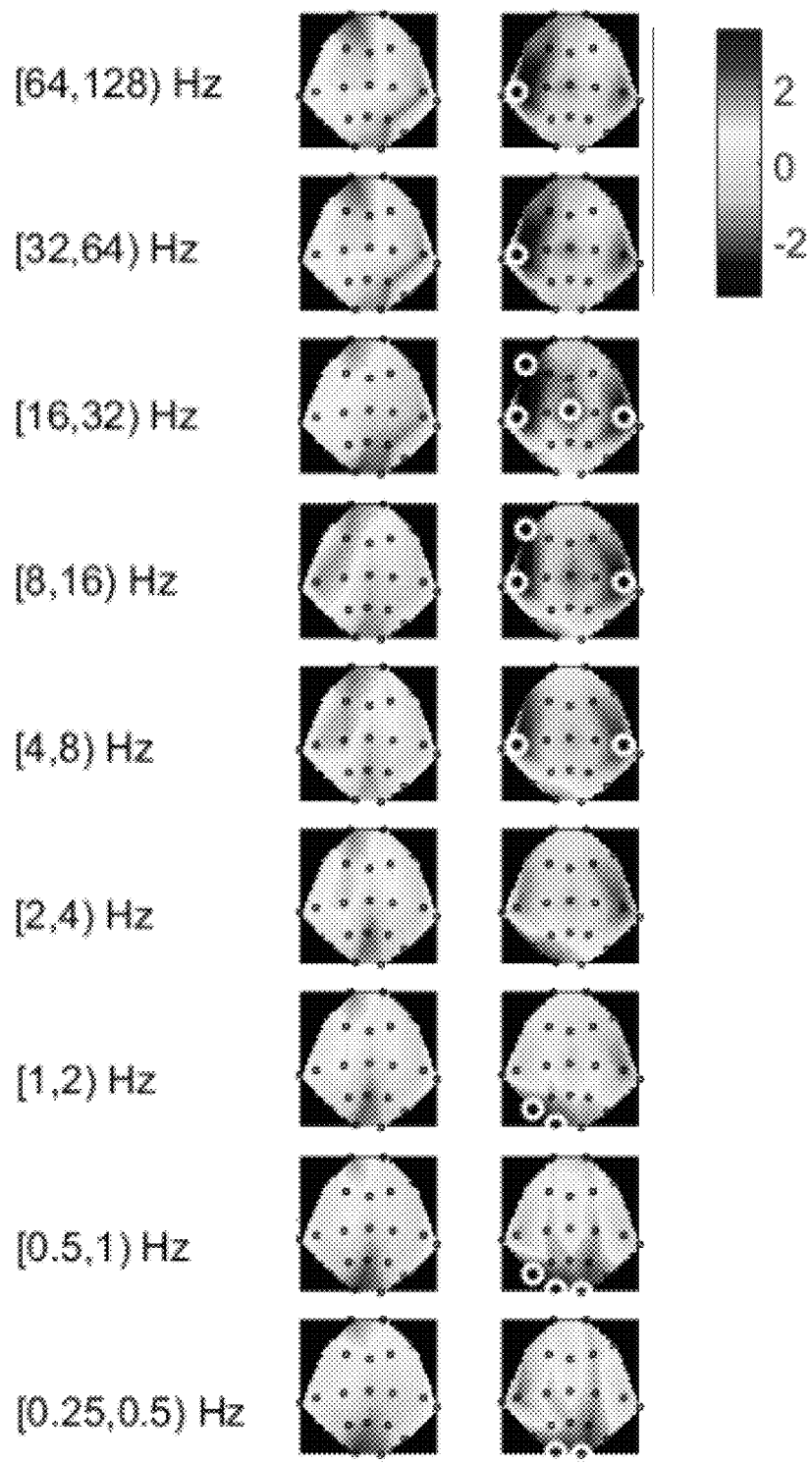
Figure 22C:
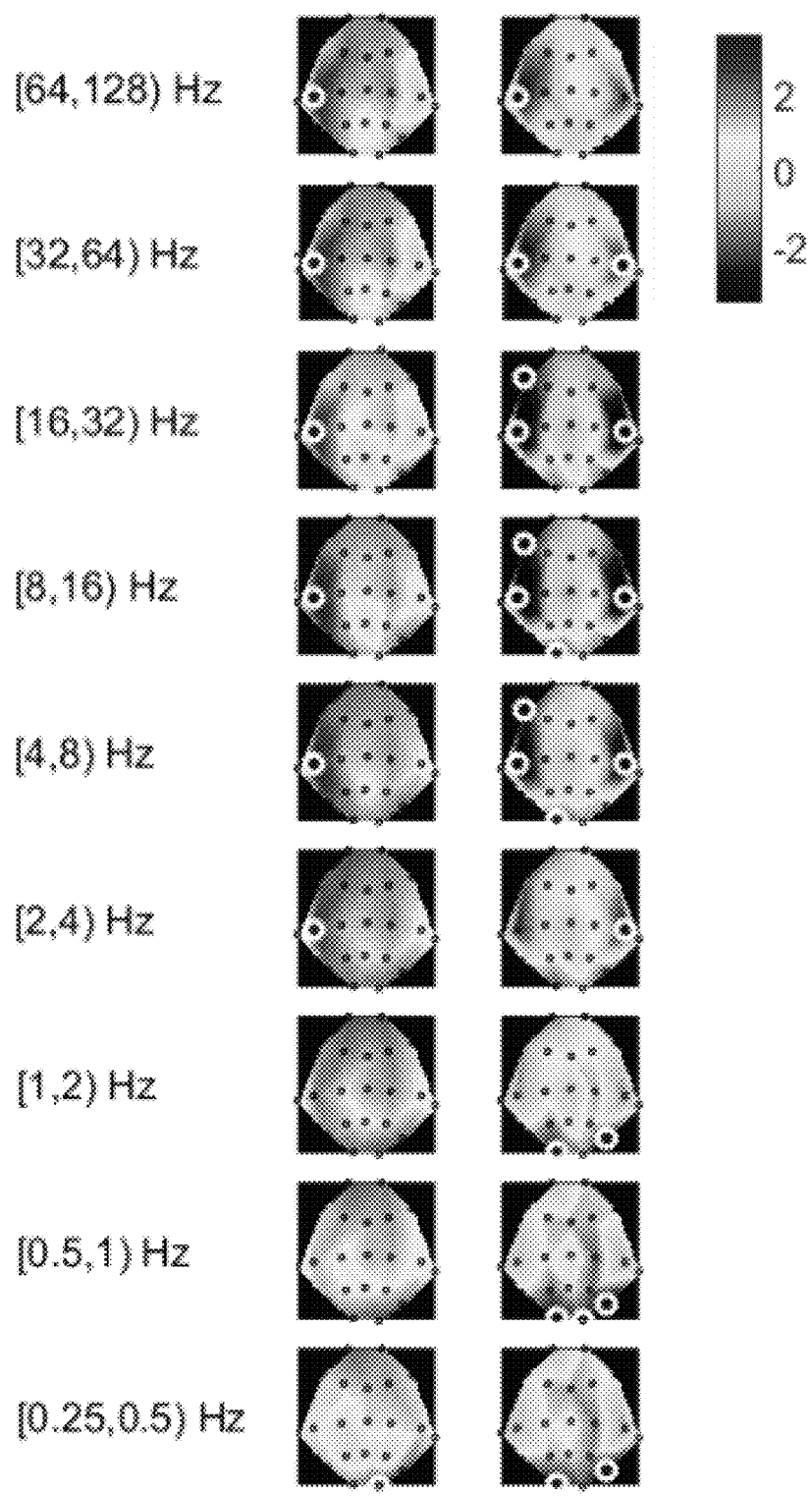
Figure 22D:
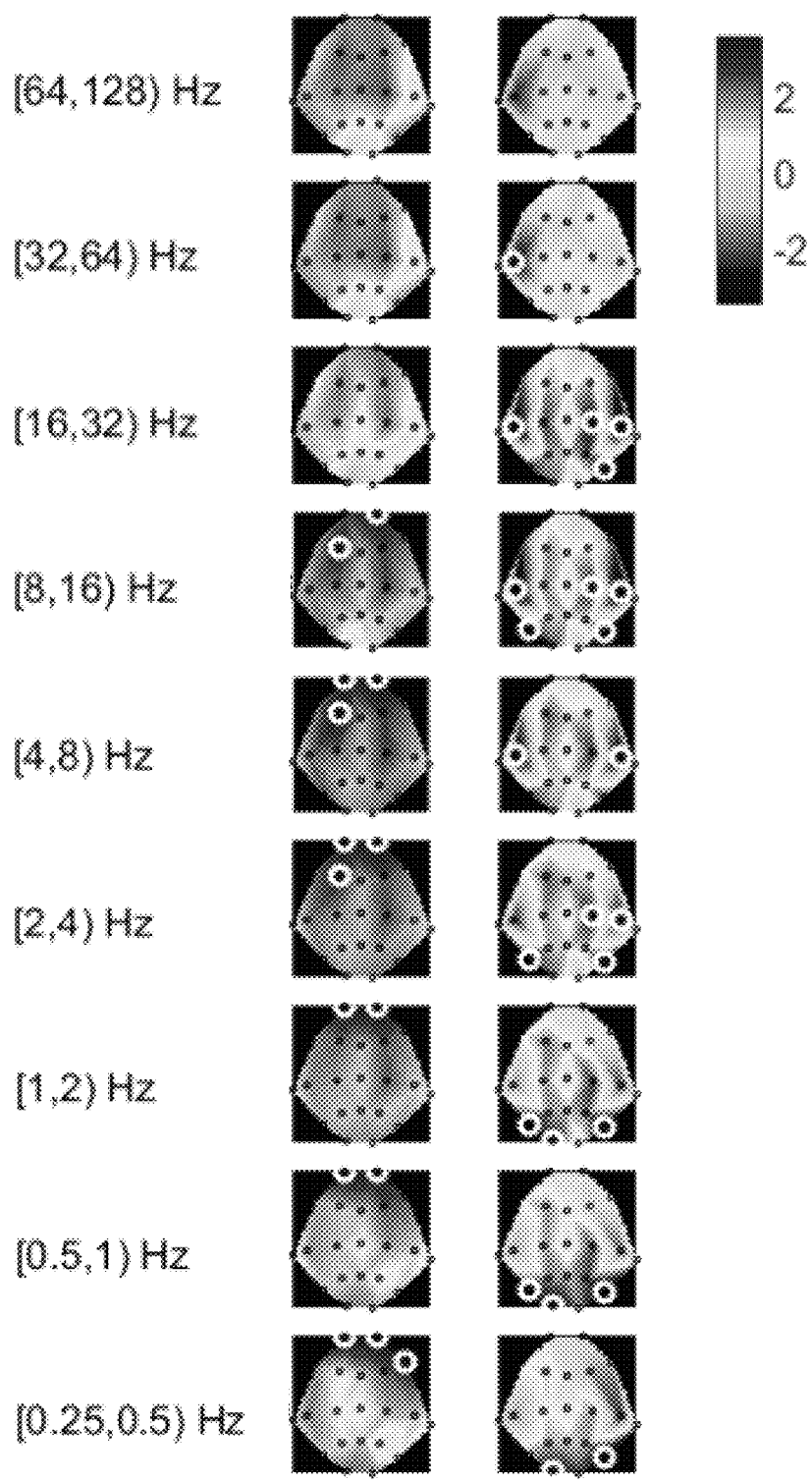

In FIGS. 22A-22D, iPDF kurtosis topographies and iPDF skewness topographies are presented with different subsets of IMFs, in accordance with an embodiment of the present disclosure. In FIG. 22A, the iPDF kurtosis topography and the iPDF skewness topography are shown representing a contrast between MCI patient group and a healthy subject group. In FIG. 22B, the iPDF kurtosis topography and the iPDF skewness topography are shown representing a contrast between CDR1 patient group and the healthy subject group. In FIG. 22C, the iPDF kurtosis topography and the iPDF skewness topography are shown representing a contrast between CDR2 patient group and the healthy subject group. In FIG. 22D, the iPDF kurtosis topography and the iPDF skewness topography are shown representing a contrast between CDR3 patient group and the healthy subject group.

2. Application of iMSE in Alzheimer's Disease

In the following examples, the intrinsic multi-scale sample entropy (iMSE) is used to analyze mild cognitive impairment (MCI) and the Alzheimer's disease. The data used here consists of 108 subjects with the following clinical profile: young healthy subject, N=25; MCI, N=23; Alzheimer's disease clinical dementia rating 1 (CDR), N=22; Alzheimer's disease CDR 2, N=24; and Alzheimer's disease CDR 3, N=14. The data are collected with the standard 21 electrodes montage over a 20 second period, and sampled at a rate of 200 Hz.

Figure 23:
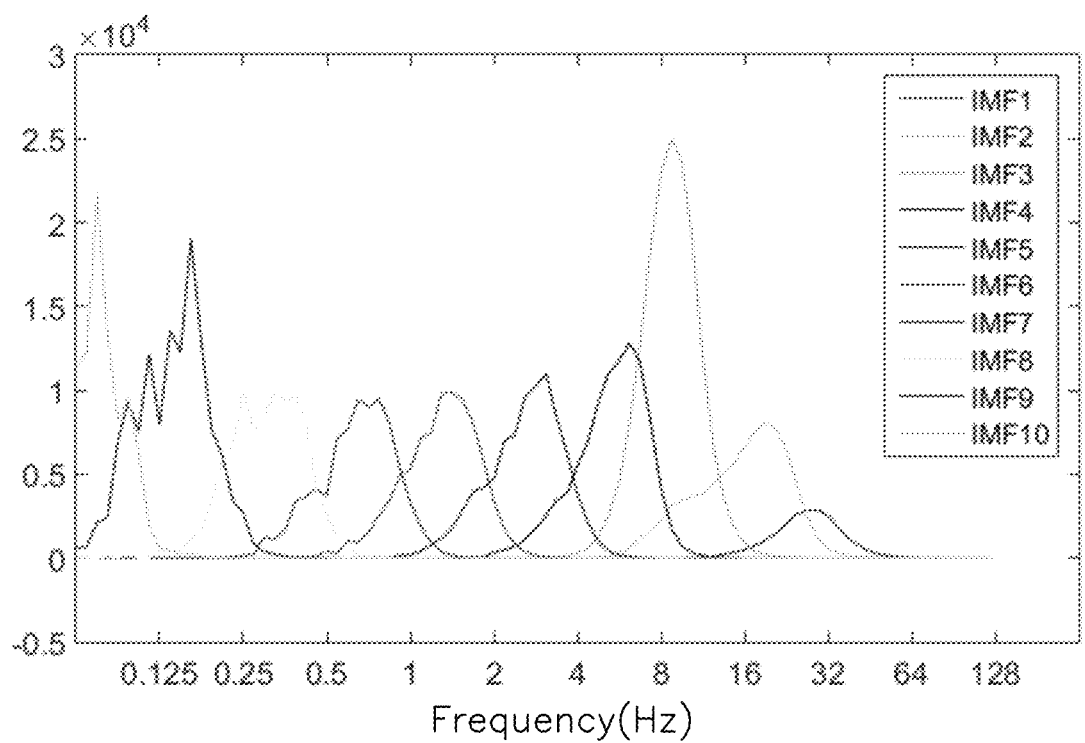
FIG. 23 is a plurality of IMFs from EEG data measured by a P3 channel of an EEG electrode system, in accordance with an embodiment of the present disclosure.

The EEG data from each of the electrodes is first decomposed by the Adaptive Ensemble Empirical Mode Decomposition (A EEMD). All data yield 10 Intrinsic Mode Function (IMF) components. The typical frequency distribution for the individual component at P3 channel of the EEG electrode is given in FIG. 23. From the distribution of frequencies in FIG. 23, IMF 9 and 10 is shown to have a central frequency of 0.125 Hz (8 second period).

Figure 24A:
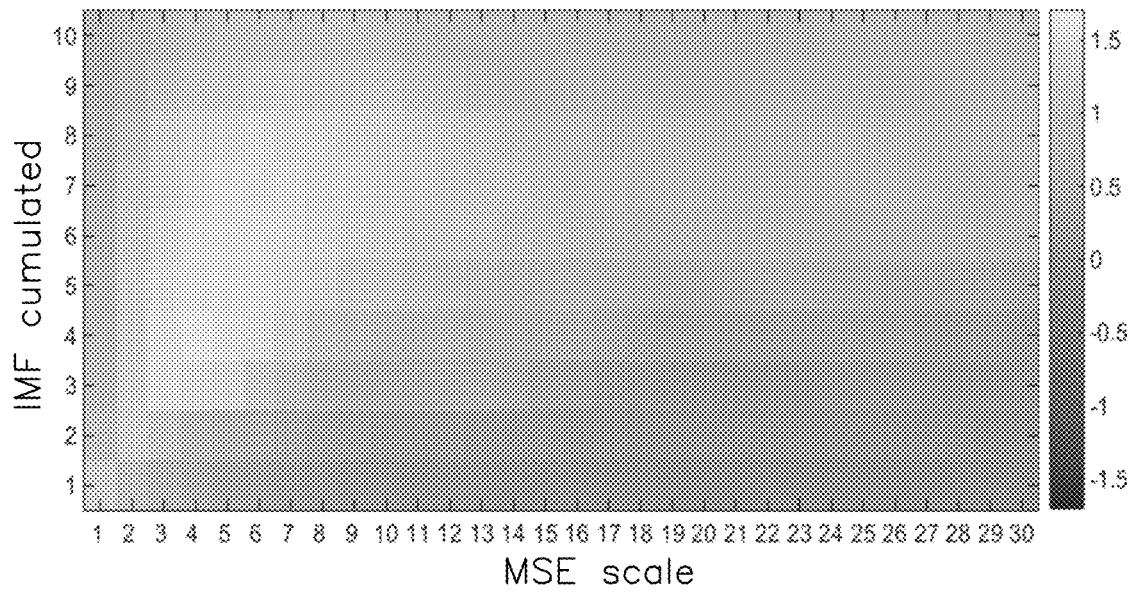
FIGS. 24A-24E are visual outputs of iMSEs for different patient groups of Alzheimer's disease and a healthy subject group, in accordance with an embodiment of the present disclosure.
Figure 24B:
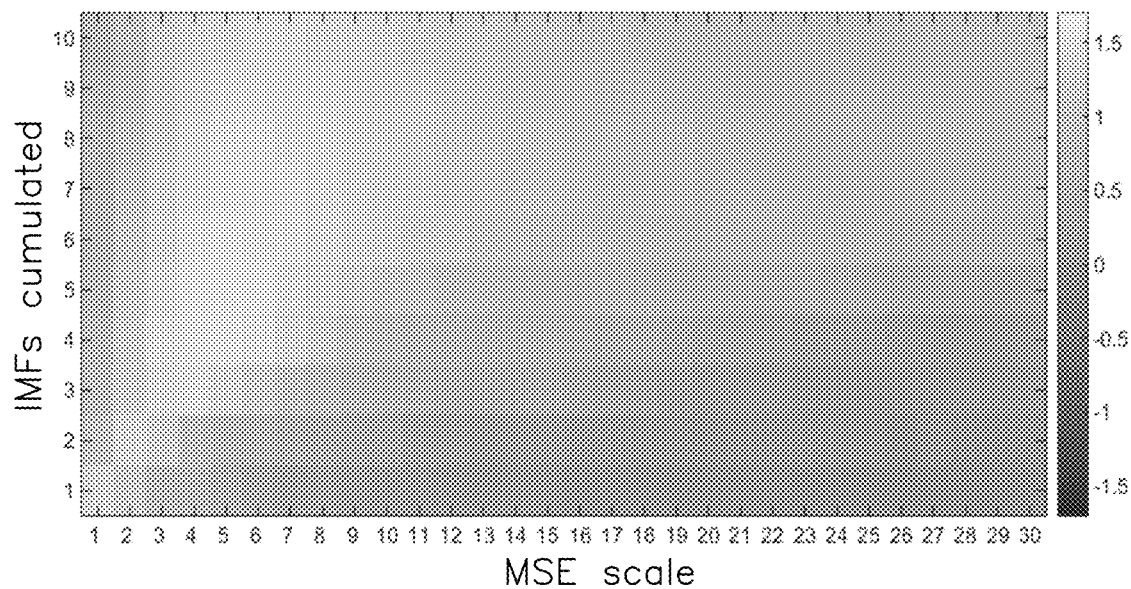
Figure 24C:
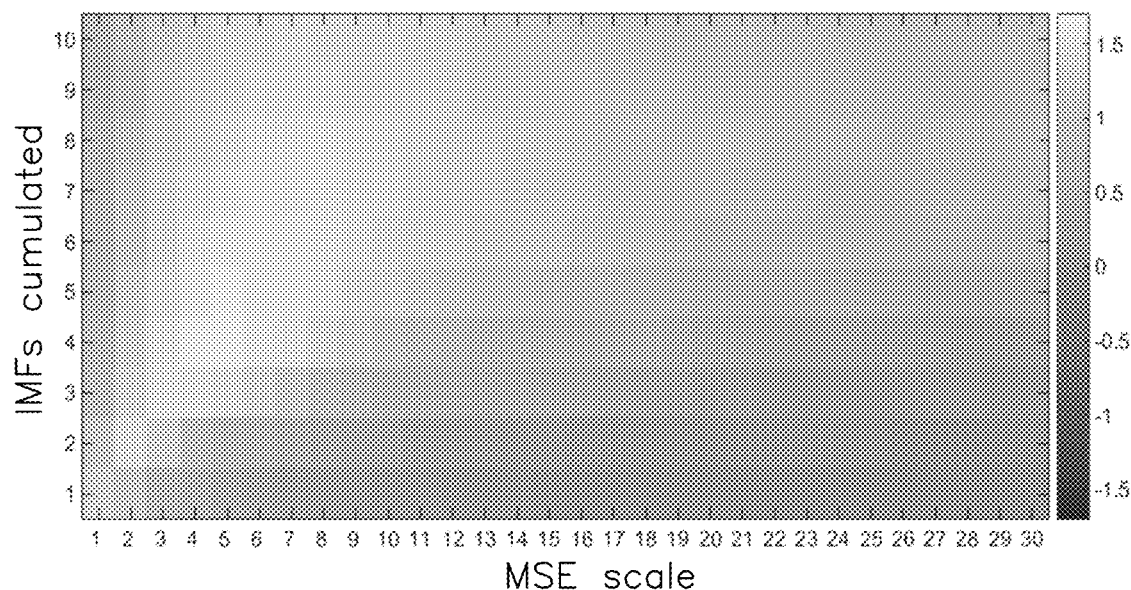
Figure 24D:
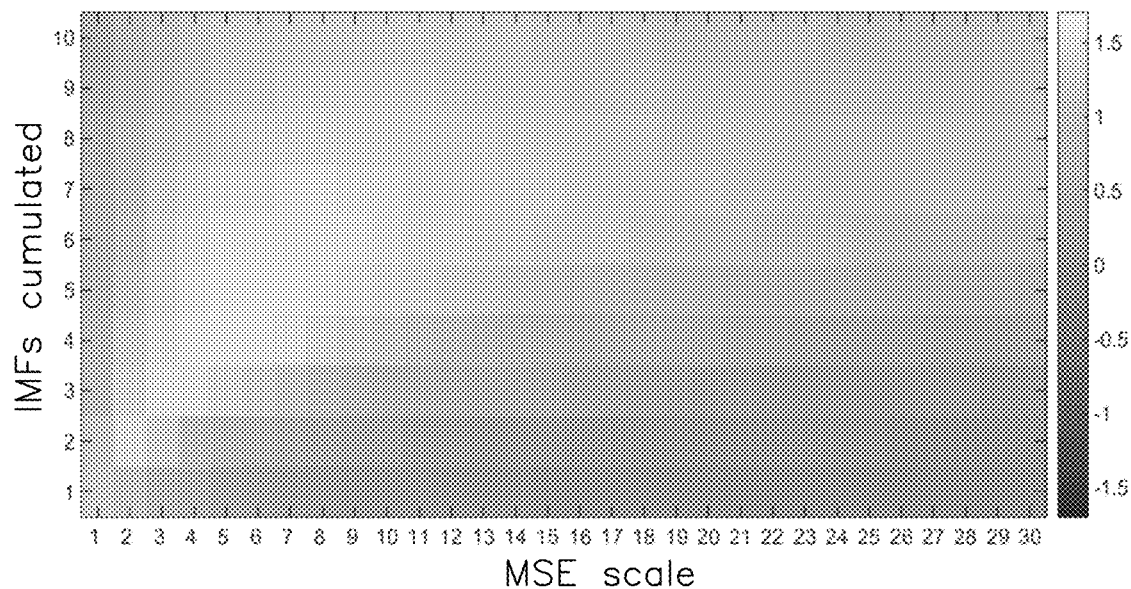
Figure 24E:
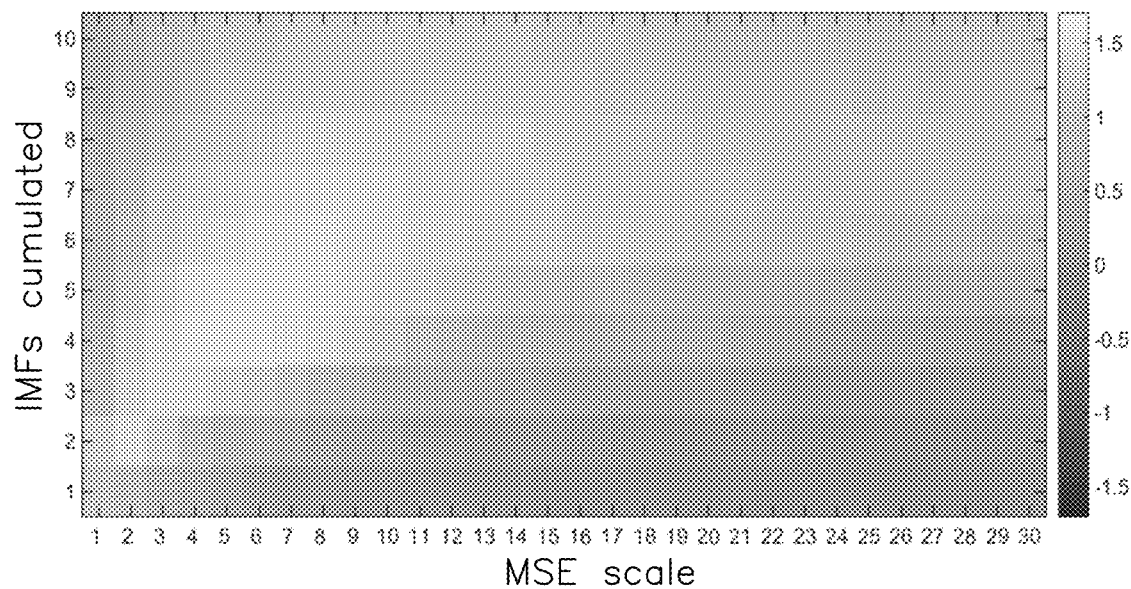

Referring to FIGS. 24A-24E, results of the ascending iMSEs of a mean iMSE's for each group at P3 channel are presented, in accordance with an embodiment of the present disclosure. In FIGS. 24A-24E, the horizontal axis is a scale of iMSE, and the vertical axis represents cumulative IMFs. Each of the visual elements, namely the blocks in FIGS. 24A-24E is defined by the horizontal axis and the vertical axis, and each of the block comprises an analyzed data unit collected over a time interval. The analyzed data unit has a first coordinate of the horizontal axis, a second coordinate of the vertical axis, and an iMSE value. FIG. 24A is the iMSE of the group of healthy subjects, FIG. 24B is the iMSE of the MCI group, FIG. 24C is the iMSE of the CDR 1 group, FIG. 24D is the iMSE of the CDR 2 group, and FIG. 24E is the iMSE of the CDR 3 group. FIGS. 24A-24E demonstrate a similar pattern: the complexity increases when more and more IMFs are involved. There is a subtle trend of the maximum concentration of the complexity matrixes gradually shifting to the coarser graining scales.

Figure 25A:
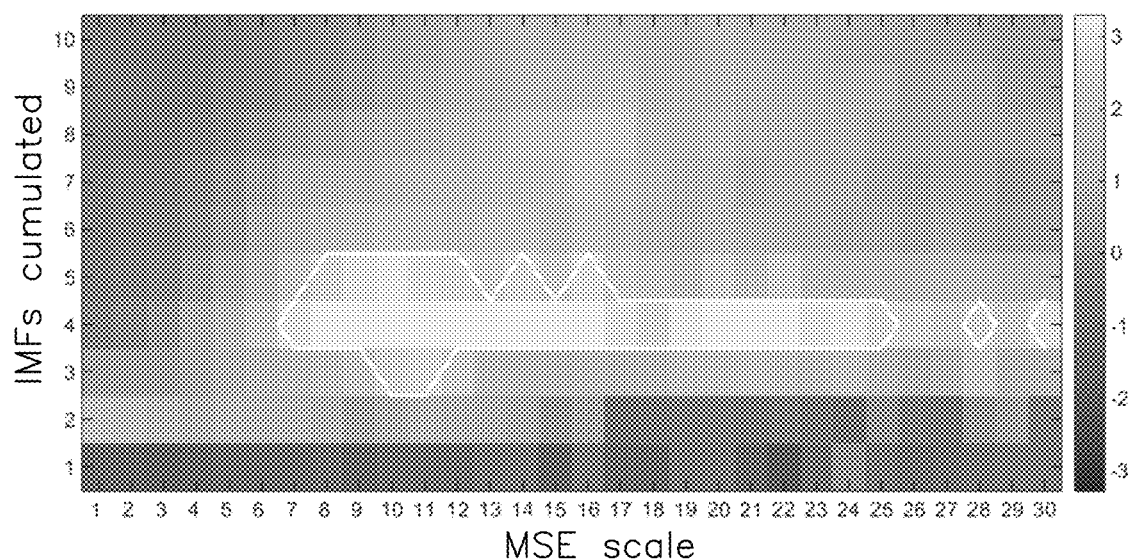
FIGS. 25A-25D are visual outputs of iMSEs for pairwise comparisons between the different groups of Alzheimer's disease patients, in accordance with an embodiment of the present disclosure.
Figure 25B:
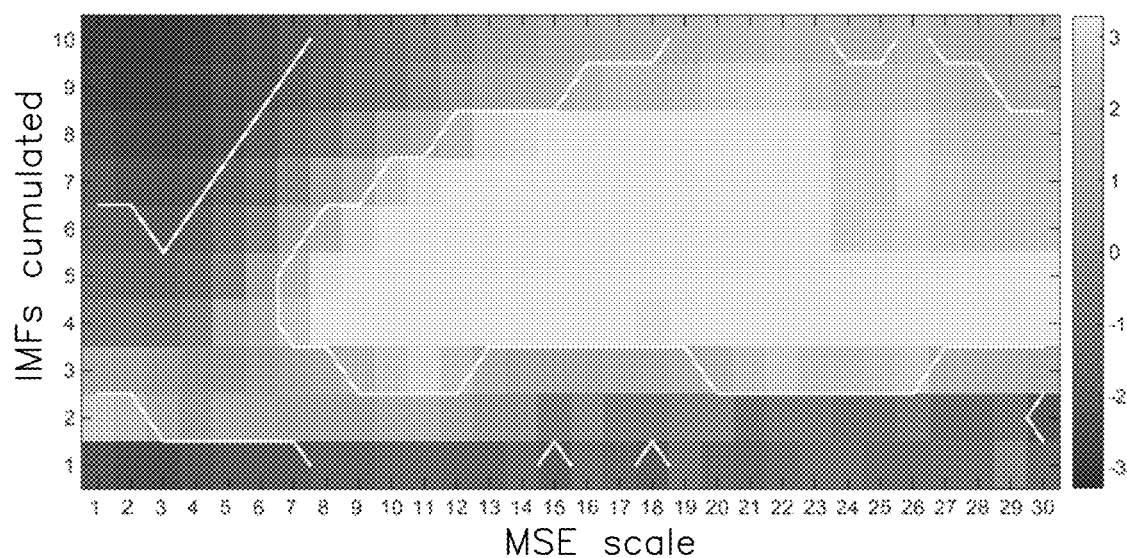
Figure 25C:
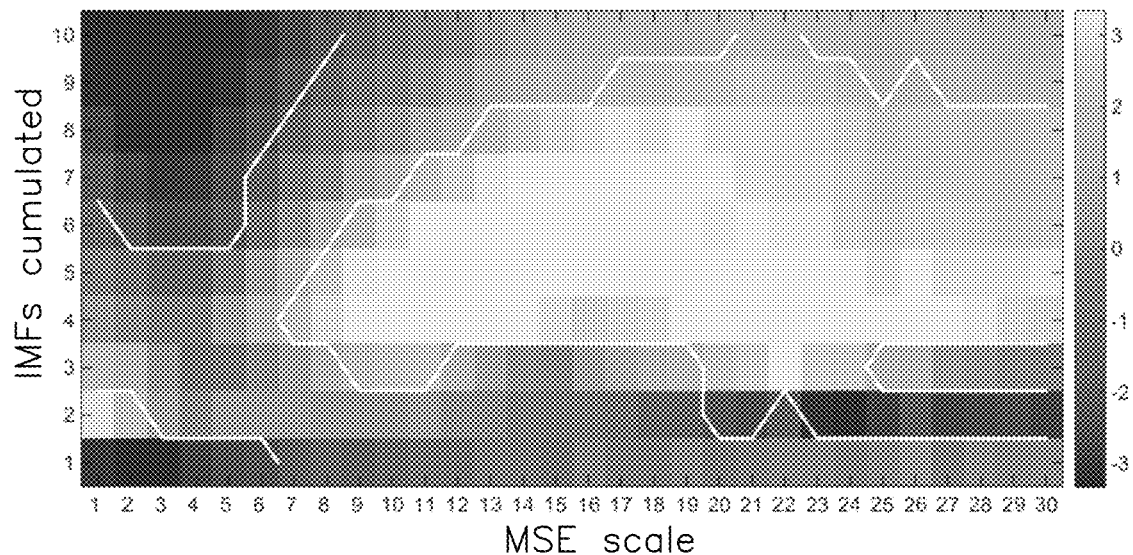
Figure 25D:
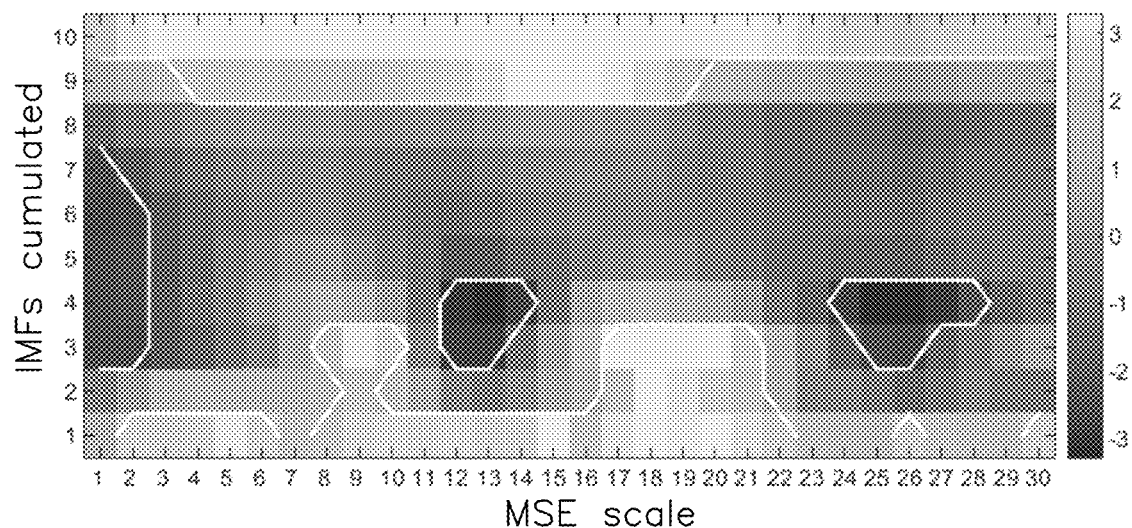

Referring to FIGS. 25A-25D, pairwise differences between the different groups are represented by the iMSE, in accordance with an embodiment of the present disclosure. In FIGS. 25A-25D, the vertical axis represents cumulative IMFs, and the horizontal axis is a scale of iMSE. FIG. 25A shows differences between the CDR 1 group and the MCI group by the iMSE, FIG. 25B shows differences between the CDR 2 group and the MCI group, FIG. 25C shows differences between the CDR 3 group and the MCI group, and FIG. 25D shows differences between the CDR 2 group and the MCI group. In FIGS. 25A-25D, the groups of patients are of the same age group, and the healthy subject group consist primarily of young college students.

In FIG. 25A, areas with statistically significant difference, with a p value less than 0.05, are marked by white contour lines. The general pattern in FIG. 25A is the loss of complexity at fine scale, but with an increase of complexity in the long coarse graining scale. However, for the differences between the MCI group and CDR 2 and 3 group, even the decreases in the fine graining scale become statistically significant, as shown in FIG. 25B and FIG. 25C.

The difference between the health control and MCI groups is shown in FIG. 25D, the difference pattern is clear if the contributions for IMF's 10, 9 and 1 are ignored. The pattern is consistent with the overall premise: diseases will cause a decrease of complexity. Here the statistically significant areas are the fine graining scales and two isolated regions. The significance of the fine graining scale is clear. Here, the iMSE show clear difference amongst the CDR cases; therefore, it offers another measure that would complement the fEEG studies.

Figure 26A:
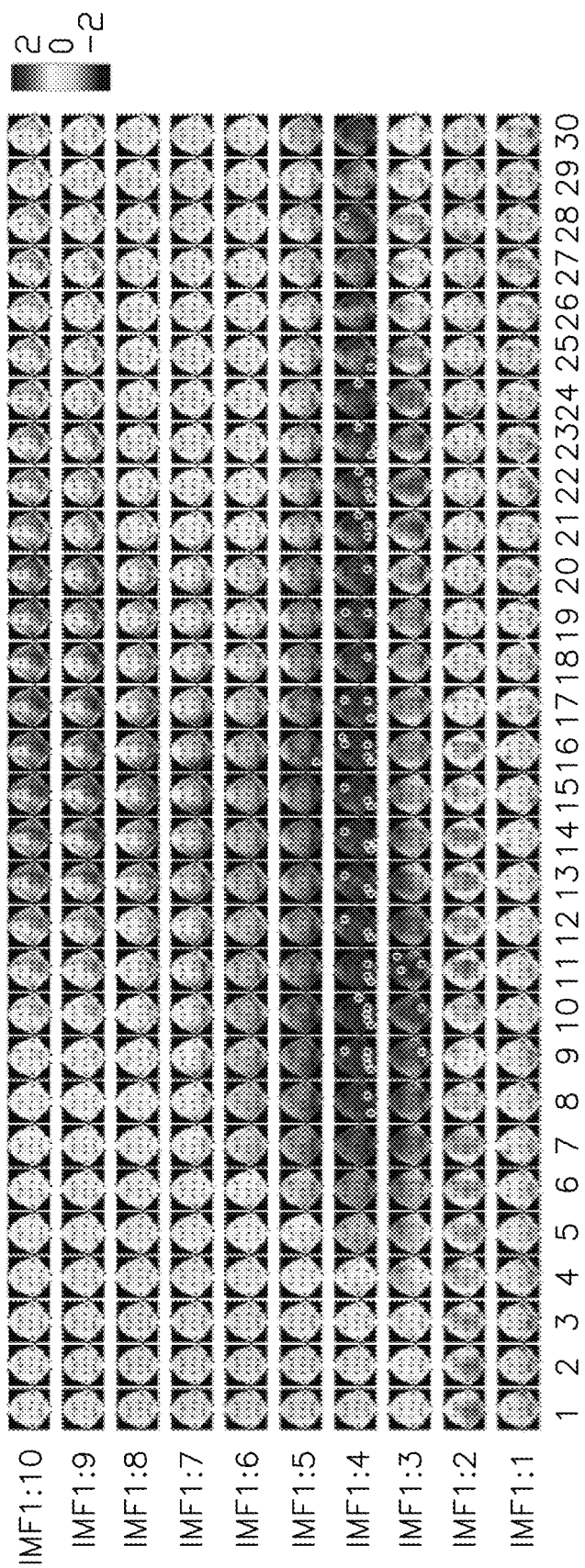
FIGS. 26A-26D are visual outputs of topographic iMSEs (TiMSEs) for pairwise comparisons between the different groups of Alzheimer's disease patients, in accordance with an embodiment of the present disclosure.
Figure 26B:
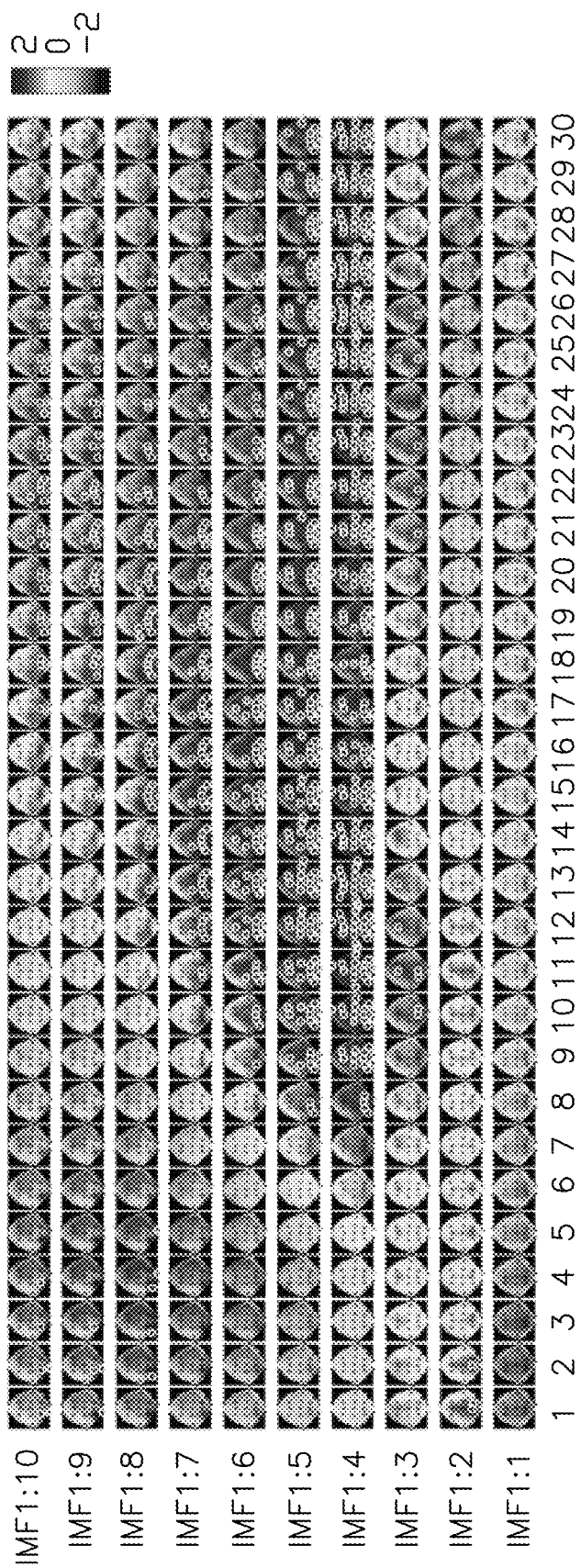
Figure 26C:
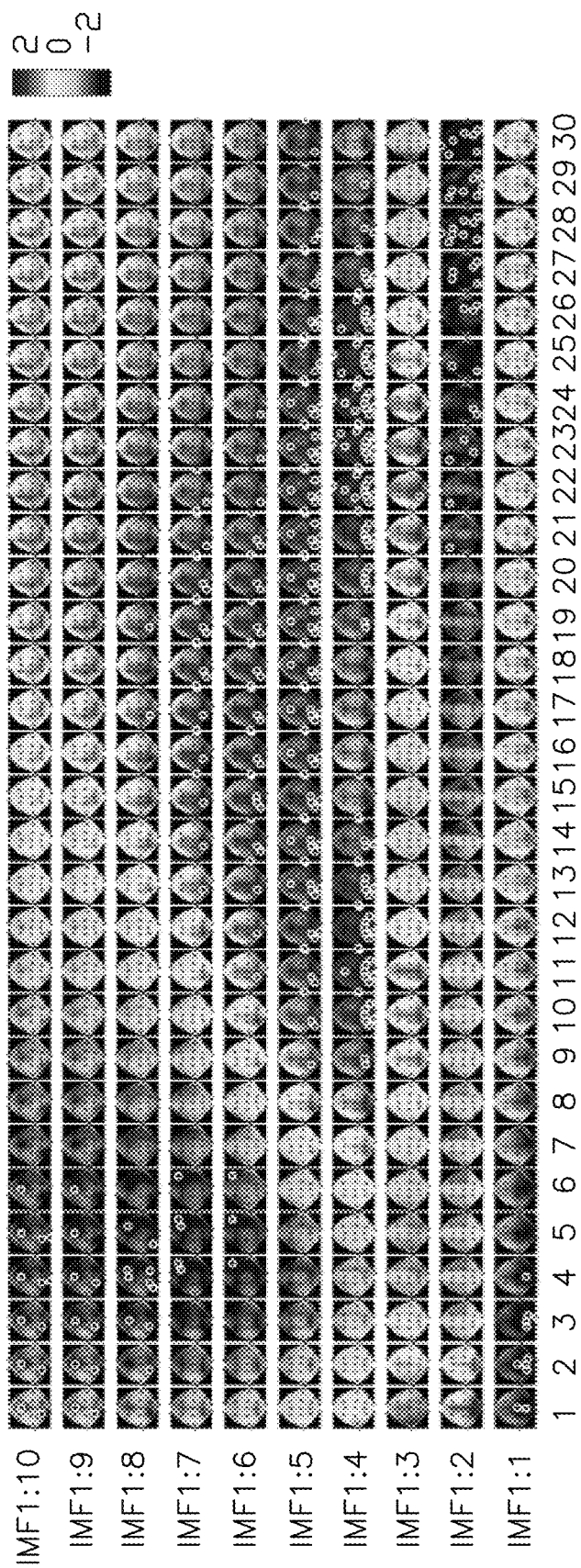
Figure 26D:
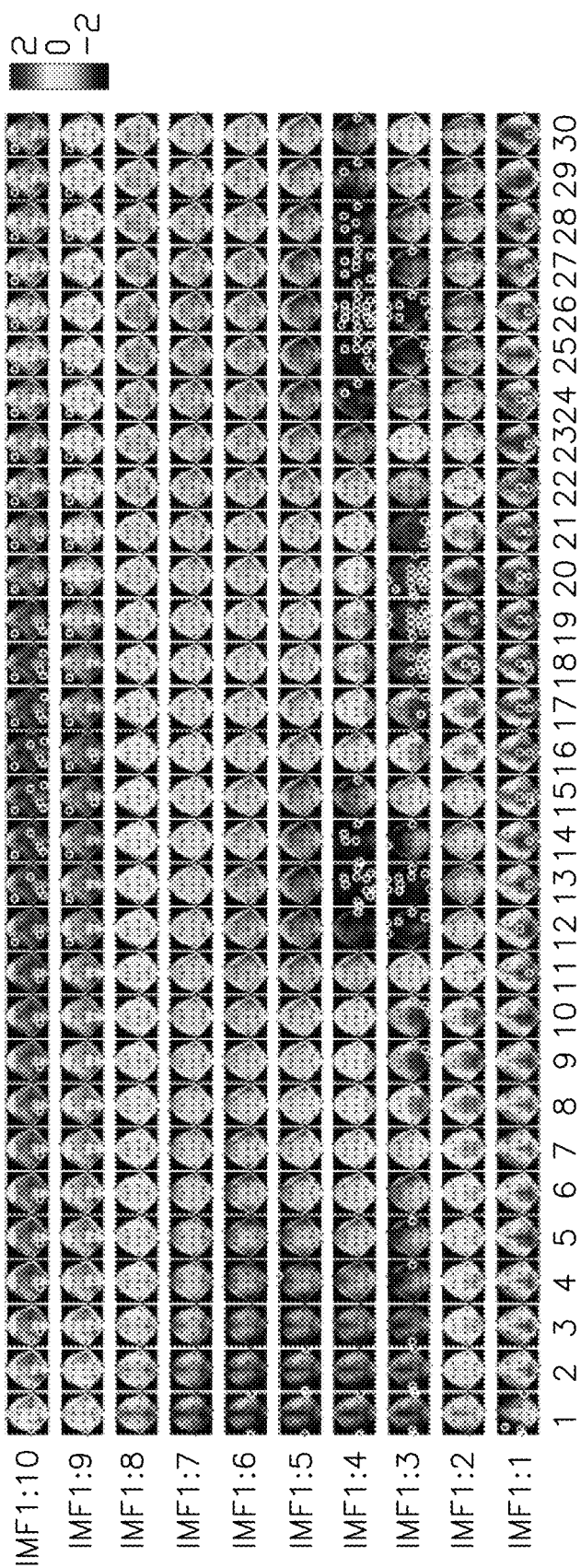

The iMSEs collected from a plurality of the detection module may be organized in the topographic form designated as Topographic iMSE (TiMSE). This new presentation gives both spatial and temporal representation of the underlying complexity variation condition. Referring to FIGS. 26A-26D, pairwise differences between different groups of patients are presented by the TiMSE, in accordance with an embodiment of the present disclosure. In FIGS. 26A-26D, the horizontal axis is a scale of iMSE, and the vertical axis represents cumulative IMFs. On the vertical axis, IMF 1:10 is a cumulation of IMF1 to IMF10, IMF 1:9 is a cumulation of IMF1 to IMF9, and so the cumulations of IMF1 to different IMFs are presented. A plurality of iMSE topographies are the visual elements of FIGS. 26A-26D, and each of the iMSE topographies comprises a boundary defining an anatomical graph of the brain, a plurality of detection units, and a plurality of intermediate areas between the detection units, similar to the iPDF topographies in FIG. 18 and FIGS. 19A-19D. Each of the detection units comprises a iMSE value, and each of the intermediate areas has a modeled iMSE value that is generated from the surrounding detection units. FIG. 26A shows differences between the CDR 1 group and the MCI group by the TiMSE, FIG. 26B shows differences between the CDR 2 group and the MCRI group, FIG. 26C shows differences between the CDR 3 group and the MCI group, and FIG. 26D shows differences between the CDR 4 group and the MCI group. The general patterns in FIGS. 26A-26D are similar to the patterns shown in FIGS. 25A-25D: a general decreasing in complexity and migration of the maximum region of complexity to the coarse graining scales in tandem with the progress of dementia. Even the statistically significant region is also similar between the FIGS. 26A-26D and the FIGS. 25A-25D.

The above results indicate that there are coherent patterns of iMSE change in tandem with the progress of dementia for the whole brain. The statistical results also indicate the present method could be used clinically for quantification of the progress in dementia, a neuro-degenerative disorder. There is also a parallelism between the iMSE and the results from fEEG (functional electroencephalography) and fEEToPG (functional electroencephalotopography) and fEEToMG (functional electroencephalotomography). High degree of complexity necessarily requires highly nonlinear modulation in the fEEG and fEEToPG and fEEToMG. Therefore, it is expected that iMSE should be equally applicable to all the cases studies with fEEG, fEEToPG, and fEEToMG, including but not limited to: Alzheimer's early detection, depression detection (anxiety and post-traumatic stress syndrome), ADHD detection, Migraine headache management, anesthesia depth, Parkinson's disease, Huntington's disease, sleep stage classifications, or drug addiction.

The embodiments shown and described above are only examples. Many details are often found in the art such as the other features of a circuit board assembly. Therefore, many such details are neither shown nor described. Even though numerous characteristics and advantages of the present technology have been set forth in the foregoing description, together with details of the structure and function of the present disclosure, the disclosure is illustrative only, and changes may be made in the detail, including in matters of shape, size and arrangement of the parts within the principles of the present disclosure up to, and including the full extent established by the broad general meaning of the terms used in the claims. It will therefore be appreciated that the embodiments described above may be modified within the scope of the claims.

What is claimed is:

1. A non-transitory computer program product embodied in a computer-readable medium and, when executed by a processor, providing a visual output for diagnosis of neurological disorders, comprising:
a first axis representing subsets of intrinsic mode functions (IMFs), wherein the IMFs are generated from a plurality of electrical activity signals of a brain;
a second axis representing a function of signal strength in a time interval; and
a plurality of visual elements, each of the plurality of visual elements defined by the first axis and the second axis, and each of the plurality of visual elements comprising a plurality of analyzed data units collected over the time interval,
wherein each of the plurality of analyzed data units comprises a first coordinate, a second coordinate, and a probability density value generated from an intrinsic probability density function of one of the subsets of IMFs, the first coordinate is one of the subsets of IMFs, and the second coordinate is an argument of the function of signal strength.

2. The non-transitory computer program product of claim 1, wherein the second axis is a standard deviation or a z-value of the signal strength in the time interval.

3. The non-transitory computer program product of claim 1, wherein the probability density value is generated from a subset of primary IMFs or a subset of secondary IMFs, each of the primary IMFs is generated from an empirical mode decomposition (EMD) of the plurality of electrical activity signals, and each of the secondary IMFs is generated from an EMD of the primary IMF.

4. A system for diagnosis of neurological disorders, comprising:
a transducer configured to detect electrical activities of a brain to generate a plurality of electrical activity signals;
a processor coupled to the transducer and configured to generate a plurality of analyzed data sets from the plurality of electrical activity signals, each of the plurality of analyzed data sets comprising a plurality of analyzed data units; and
at least one of a projector, a monitor, and a printer configured to render a visual output space according to the plurality of analyzed data sets generated by the processor, and display a visual output,
wherein the visual output comprises a first axis representing subsets of intrinsic mode functions (IMFs), a second axis representing a function of signal strength in a time interval, and a plurality of visual elements defined by the first axis and the second axis, wherein the IMFs are generated from the plurality of electrical activity signals by the processor, each of the plurality of visual elements comprises a plurality of analyzed data units collected over the time interval, and each of the plurality of analyzed data units comprises a first coordinate, a second coordinate, and a probability density value generated by an intrinsic probability density function of one of the subsets of IMFs, the first coordinate is one of the subsets of IMFs, and the second coordinate is an argument of the function of signal strength.

5. The system of claim 4, wherein the second axis is a standard deviation or a z-value of the signal strength in the time interval.

6. The system of claim 4, wherein the probability density value is generated from a subset of primary IMFs or a subset of secondary IMFs, each of the primary IMFs is generated from an empirical mode decomposition (EMD) of the plurality of electrical activity signals, and each of the secondary IMFs is generated from an EMD of the primary IMF.

* * * * *